United States Patent
Fearnot et al.

(10) Patent No.: US 12,186,175 B2
(45) Date of Patent: Jan. 7, 2025

(54) STORAGE DEVICES, LOADING DEVICES, DELIVERY SYSTEMS, KITS, AND ASSOCIATED METHODS

(71) Applicants: Cook Medical Technologies LLC, Bloomington, IN (US); Muffin Incorporated, West Lafayette, IN (US)

(72) Inventors: Neal Fearnot, West Lafayette, IN (US); Sarah Robbins, Lafayette, IN (US); Marc C. Buhrmester, Dayton, IN (US); Joshua Krieger, Topsfield, MA (US)

(73) Assignees: Cook Medical Technologies LLC, Bloomington, IN (US); Muffin Incorporated, West Lafayette, IN (US)

( * ) Notice: Subject to any disclaimer, the term of this patent is extended or adjusted under 35 U.S.C. 154(b) by 1033 days.

(21) Appl. No.: 17/261,053

(22) PCT Filed: Jul. 5, 2019

(86) PCT No.: PCT/US2019/040666
§ 371 (c)(1),
(2) Date: Jan. 18, 2021

(87) PCT Pub. No.: WO2020/010292
PCT Pub. Date: Jan. 9, 2020

(65) Prior Publication Data
US 2021/0259836 A1    Aug. 26, 2021

Related U.S. Application Data

(60) Provisional application No. 62/694,660, filed on Jul. 6, 2018.

(51) Int. Cl.
*A61F 2/00*     (2006.01)
*A61B 50/30*    (2016.01)
(Continued)

(52) U.S. Cl.
CPC ............ *A61F 2/0095* (2013.01); *A61B 50/30* (2016.02); *A61F 2/2412* (2013.01);
(Continued)

(58) Field of Classification Search
CPC ........ A61F 2/0095; A61F 2/46; A61F 2/9522; A61F 2/9525; A61F 2/2412;
(Continued)

(56) References Cited

U.S. PATENT DOCUMENTS 2,305,261 A    12/1942    Kinley
3,052,246 A     9/1962    Beard
(Continued)

FOREIGN PATENT DOCUMENTS

AU    2014311739 B2    8/2017
CA    2863888          3/2015
(Continued)

OTHER PUBLICATIONS

Office Action (Notice of Allowance and Fees Due (PTOL-85)) dated Mar. 8, 2022 for U.S. Appl. No. 16/503,675 (pp. 1-8).
(Continued)

*Primary Examiner* — Jerrah Edwards
*Assistant Examiner* — Jose H. Trevino, III
(74) *Attorney, Agent, or Firm* — MacMillan, Sobanski & Todd, LLC

(57) ABSTRACT

Storage devices, loading devices, delivery systems, kits, and associated methods for implantable medical devices are described. An example embodiment of a storage device includes a storage member, a first cap, and a second cap. The storage member has a first end, a second end, and a main body that defines a first opening, a second opening, a passageway, a separating wall, and a plurality of holes. The passageway has a first portion and a second portion. The first portion extends from the first end of the storage member to
(Continued)

the separating wall and the second portion extends from the second end of the storage member to the separating wall. Each hole of the plurality of holes extends through the separating wall and provides access between the first portion and the second portion. Each of the first and second caps is releasably attached to the storage member.

23 Claims, 44 Drawing Sheets

(51) Int. Cl.
*A61F 2/24* (2006.01)
*A61F 2/46* (2006.01)
*A61F 2/95* (2013.01)

(52) U.S. Cl.
CPC .............. *A61F 2/2436* (2013.01); *A61F 2/24* (2013.01); *A61F 2/46* (2013.01); *A61F 2/9526* (2020.05); *A61L 2300/404* (2013.01)

(58) Field of Classification Search
CPC ........ A61F 2/2436; A61F 2/24; A61F 2/9526; A61F 2/2427; A61B 50/30; A61L 2300/404
See application file for complete search history.

(56) References Cited

U.S. PATENT DOCUMENTS

| | | | |
|---|---|---|---|
| 3,070,105 | A | 12/1962 | Brown |
| 4,014,333 | A | 3/1977 | McIntyre |
| 4,372,743 | A | 2/1983 | Lane |
| 4,602,763 | A | 7/1986 | Gaylin |
| 4,635,989 | A | 1/1987 | Tremblay |
| 4,869,299 | A | 9/1989 | Handke |
| 4,891,239 | A | 1/1990 | Dudley |
| 5,068,086 | A | 11/1991 | Sklenak |
| 5,376,110 | A | 12/1994 | Tu |
| 5,486,193 | A | 1/1996 | Bourne |
| 5,725,519 | A | 3/1998 | Penner |
| 5,810,873 | A | 9/1998 | Morales |
| 5,824,060 | A | 10/1998 | Christie |
| 5,873,879 | A | 2/1999 | Figueroa |
| 5,911,452 | A | 6/1999 | Yan |
| 5,928,258 | A | 7/1999 | Khan |
| 6,068,635 | A | 5/2000 | Gianotti |
| 6,090,035 | A | 7/2000 | Campbell |
| 6,096,027 | A | 8/2000 | Layne |
| 6,149,680 | A | 11/2000 | Shelso |
| 6,471,718 | B1 | 10/2002 | Staehle |
| 6,640,412 | B2 | 11/2003 | Iancea |
| 6,689,123 | B2 | 2/2004 | Pinchasik |
| 6,702,845 | B1 | 3/2004 | Cully |
| 6,823,576 | B2 | 11/2004 | Austin |
| 6,859,986 | B2 | 3/2005 | Jackson |
| 6,915,560 | B2 | 7/2005 | Austin |
| 6,926,732 | B2 | 8/2005 | Derus |
| 7,104,343 | B2 | 9/2006 | Roberts |
| 7,402,171 | B2 | 7/2008 | Osborne |
| 7,819,388 | B2 | 10/2010 | McCallion |
| 7,837,706 | B2 | 11/2010 | Sogard |
| 7,959,595 | B2 | 6/2011 | Melsheimer |
| 8,262,065 | B2 | 9/2012 | Matsuyama |
| 8,312,825 | B2 | 11/2012 | Holecek |
| 8,359,721 | B2 | 1/2013 | Melsheimer |
| 8,585,019 | B2 | 11/2013 | Melsheimer |
| 8,608,795 | B2 | 12/2013 | Melsheimer |
| 8,663,320 | B2 | 3/2014 | Chambers |
| 8,702,589 | B2 | 4/2014 | Kuyava |
| 8,808,350 | B2 | 8/2014 | Schreck et al. |
| 9,629,704 | B2 | 4/2017 | Melsheimer |
| 9,872,760 | B2 | 1/2018 | Lopez |
| 10,481,051 | B2 | 11/2019 | Tran |
| 2001/0001128 | A1 | 5/2001 | Holman |
| 2002/0177899 | A1 | 11/2002 | Eum |
| 2003/0055492 | A1 | 3/2003 | Shaolian |
| 2003/0083730 | A1 | 5/2003 | Stinson |
| 2003/0114910 | A1 | 6/2003 | Juhani Laakso |
| 2003/0208254 | A1 | 11/2003 | Shortt |
| 2003/0225445 | A1 | 12/2003 | Derus |
| 2004/0117012 | A1 | 6/2004 | Vincent |
| 2006/0064152 | A1 | 3/2006 | Olson |
| 2006/0167468 | A1 | 7/2006 | Gabbay |
| 2006/0183383 | A1 | 8/2006 | Asmus |
| 2006/0230592 | A1 | 10/2006 | Heaney |
| 2006/0247755 | A1 | 11/2006 | Pal |
| 2006/0253114 | A1 | 11/2006 | Saadat |
| 2007/0050006 | A1 | 3/2007 | Lavelle |
| 2007/0056346 | A1 | 3/2007 | Spenser |
| 2007/0061009 | A1 | 3/2007 | Spenser |
| 2007/0162100 | A1 | 7/2007 | Gabbay |
| 2007/0270931 | A1 | 11/2007 | Leanna |
| 2007/0270932 | A1* | 11/2007 | Headley .................. A61F 2/95 623/1.11 |
| 2007/0270937 | A1 | 11/2007 | Leanna |
| 2007/0282370 | A1 | 12/2007 | Brady |
| 2008/0281293 | A1 | 11/2008 | Peh |
| 2009/0054976 | A1 | 2/2009 | Tuval |
| 2009/0076587 | A1 | 3/2009 | Cully |
| 2009/0143852 | A1 | 6/2009 | Chambers |
| 2009/0143857 | A1 | 6/2009 | Melsheimer |
| 2009/0182410 | A1 | 7/2009 | Case |
| 2009/0192496 | A1 | 7/2009 | Suwito |
| 2009/0259287 | A1 | 10/2009 | Valaie |
| 2010/0057185 | A1 | 3/2010 | Melsheimer |
| 2010/0121424 | A1* | 5/2010 | Kubena .................. A61F 2/95 623/1.11 |
| 2011/0046712 | A1* | 2/2011 | Melsheimer .......... A61F 2/9526 623/1.11 |
| 2011/0288558 | A1 | 11/2011 | Nimgaard |
| 2013/0282099 | A1 | 10/2013 | Huynh |
| 2014/0081387 | A1 | 3/2014 | Melsheimer |
| 2014/0121748 | A1 | 5/2014 | Melsheimer |
| 2015/0173764 | A1 | 6/2015 | Kubiak |
| 2016/0074185 | A1 | 3/2016 | Melsheimer |
| 2016/0130042 | A1 | 5/2016 | Gascoine |
| 2017/0042662 | A1 | 2/2017 | Kubiak |
| 2017/0151075 | A9 | 6/2017 | Melsheimer |
| 2017/0239037 | A1 | 8/2017 | Shino |
| 2018/0071074 | A1 | 3/2018 | Ludlow |

FOREIGN PATENT DOCUMENTS

| | | |
|---|---|---|
| CN | 201314886 Y | 9/2009 |
| CN | 106456327 A | 2/2017 |
| CN | 106624575 | 5/2017 |
| CN | 108024864 A | 5/2018 |
| DE | 19851846 | 5/2000 |
| EP | 0657147 | 6/1995 |
| EP | 0938880 | 9/1999 |
| EP | 1362563 | 11/2003 |
| GB | 2113249 | 8/1983 |
| NZ | 333617 | 7/2000 |
| WO | 9959503 | 11/1999 |
| WO | 0040176 | 7/2000 |
| WO | 0249541 | 6/2002 |
| WO | 2007061801 | 5/2007 |
| WO | 2008091409 | 7/2008 |
| WO | 2009073767 | 6/2009 |
| WO | 2015031025 A1 | 3/2015 |

OTHER PUBLICATIONS

Chinese Search Report, Application No. 2019800571954, dated Oct. 25, 2023.
First Chinese Office Action, Application No. 201980057195.4, dated Oct. 28, 2023.
Chinese Second Action, Application No. 201980057195.4, dated Apr. 10, 2024.
Australian Examination Report, Application No. 2022291640, dated Dec. 15, 2023.

(56) References Cited

OTHER PUBLICATIONS

1 Japanese Office Action, Application No. 2021-521943, dated Jun. 13, 2023.
Korean Brief Summary of a Notice of Preliminary Rejection, Application No. 10-2021-7003790, dated Jan. 19, 2024.
PCT International Search Report and Written Opinion, Application No. PCT/US2019/040666, dated Nov. 22, 2019.

\* cited by examiner

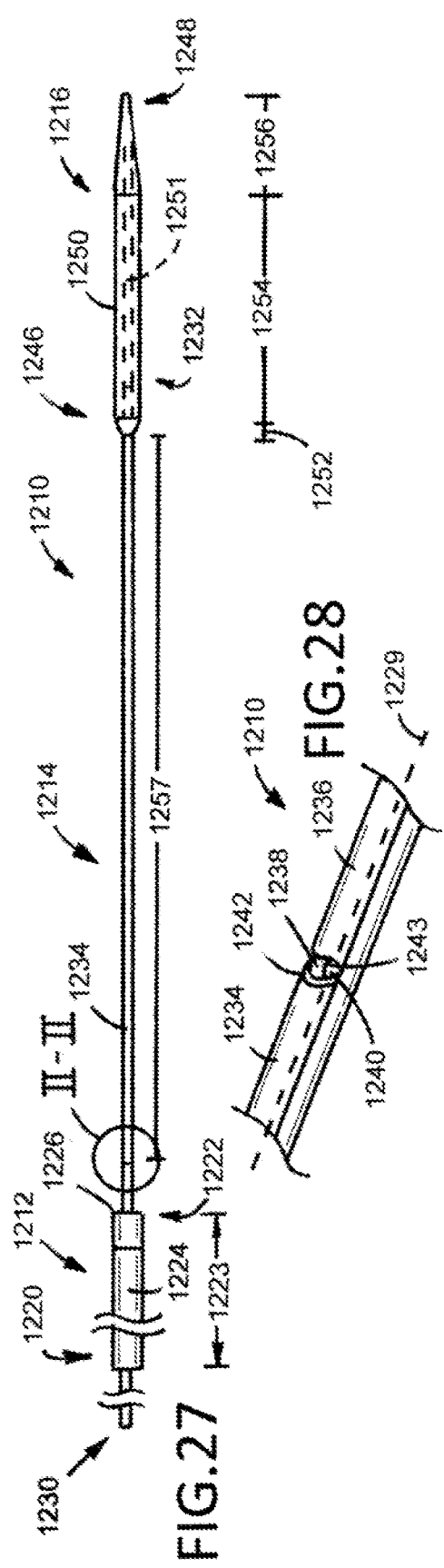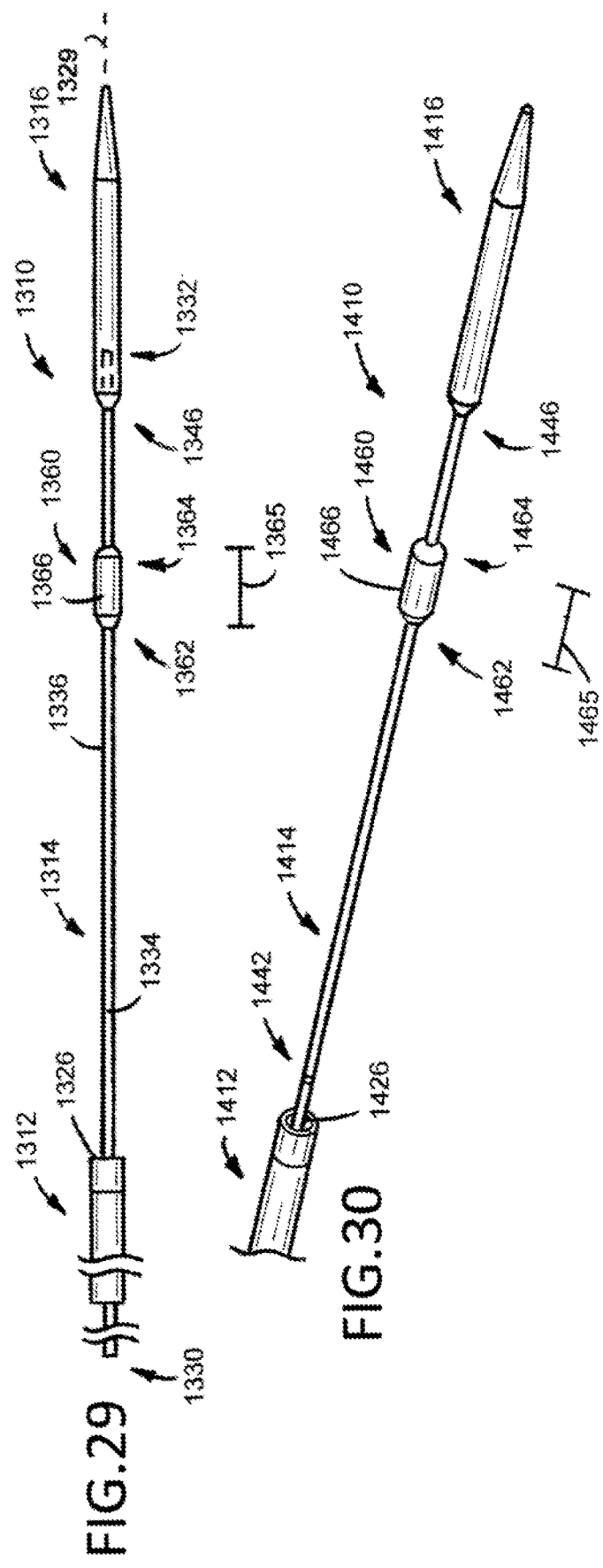

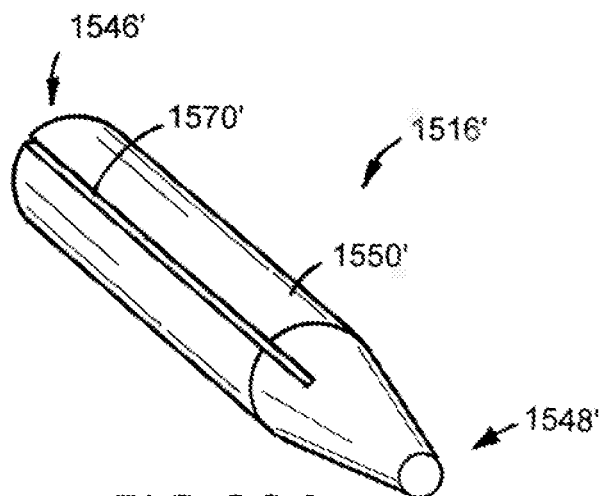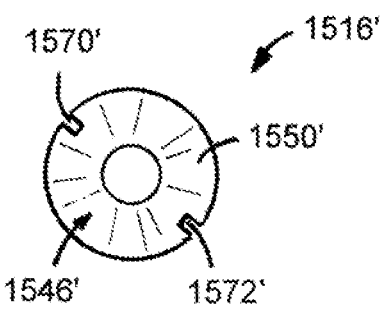
FIG.32A  FIG.32B
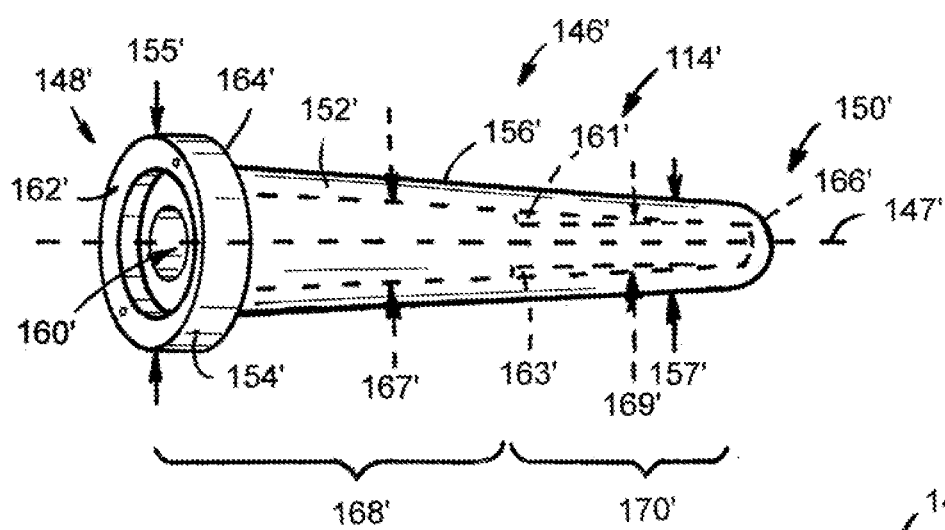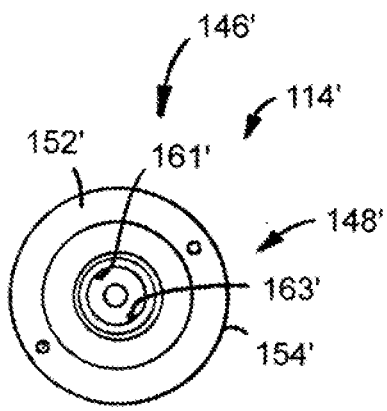
FIG.32C  FIG.32D

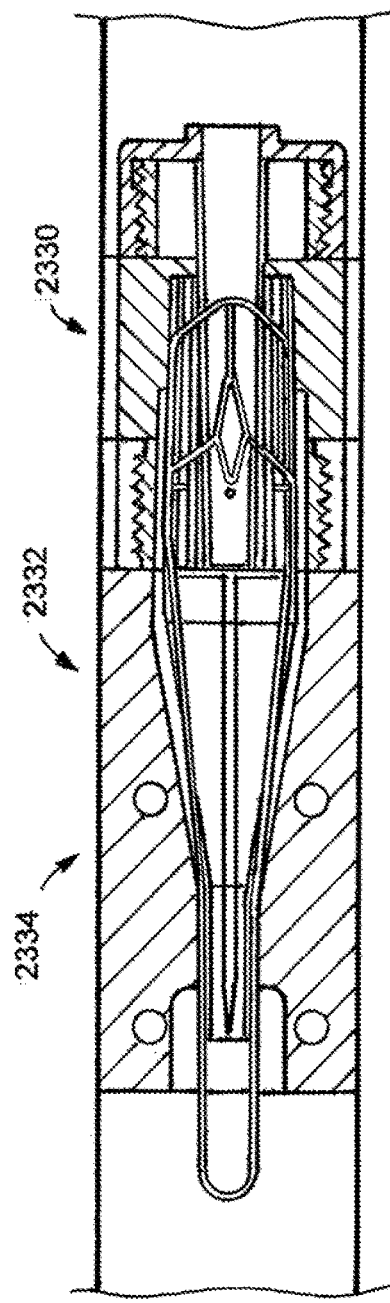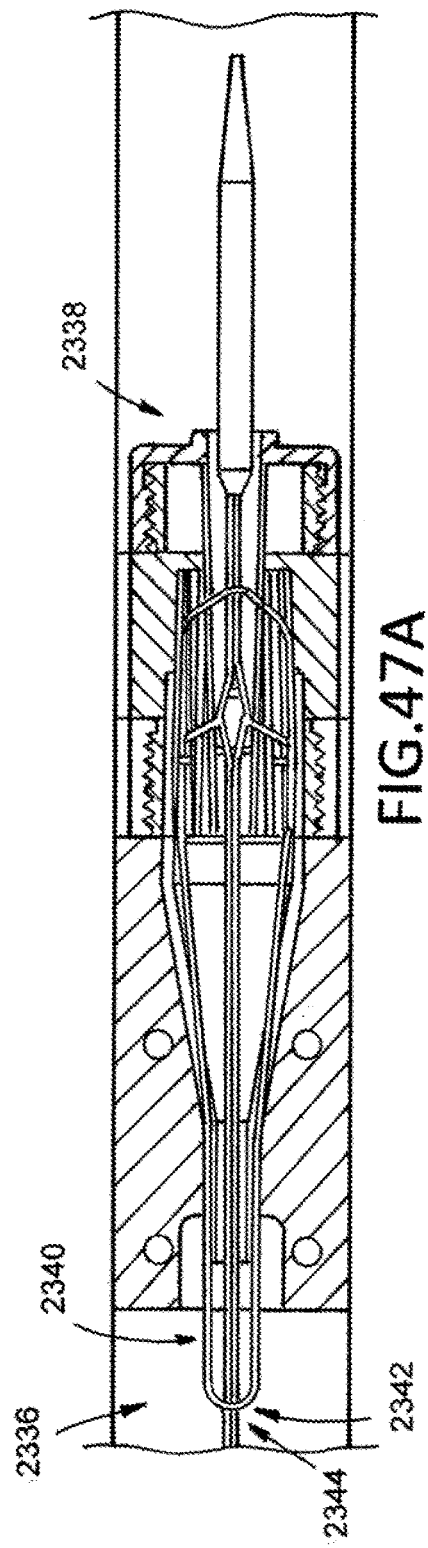

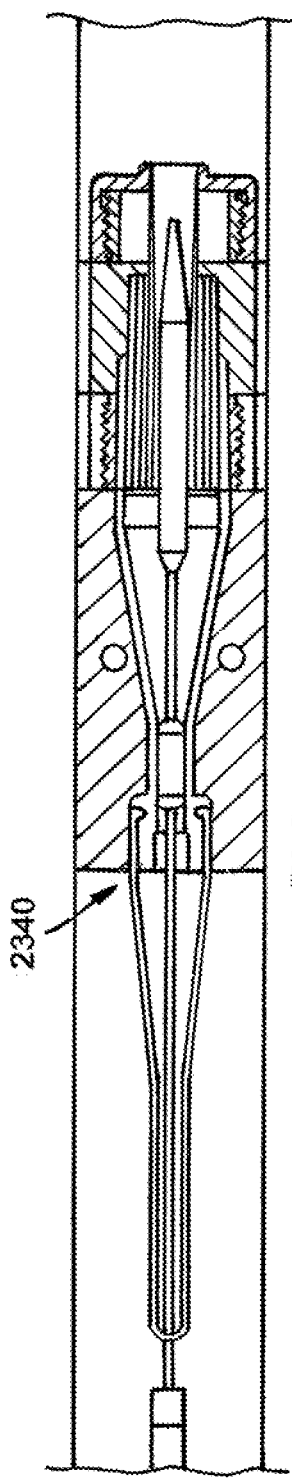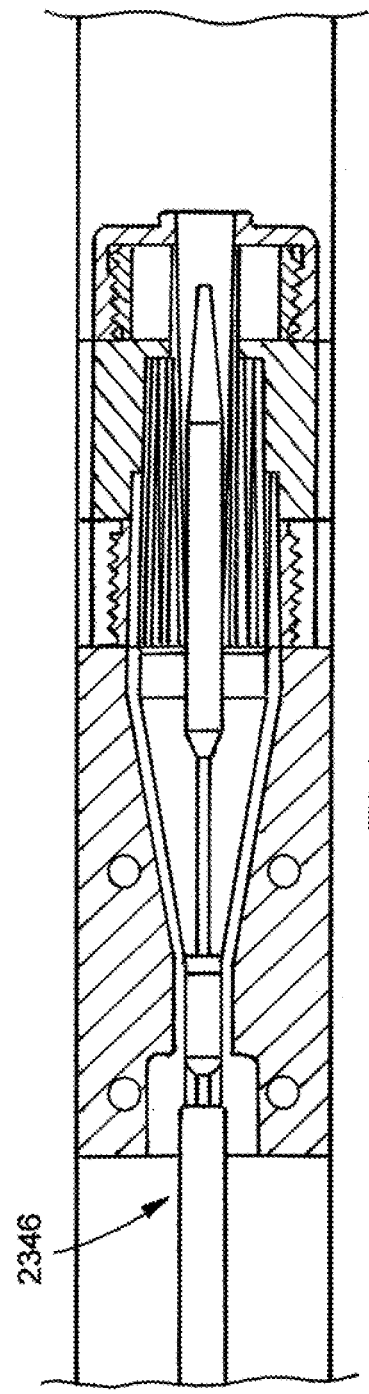

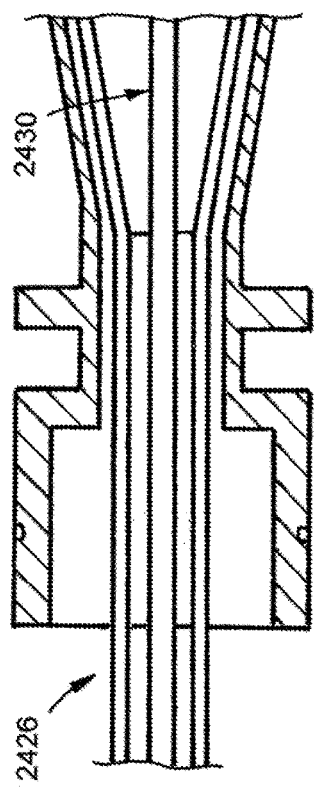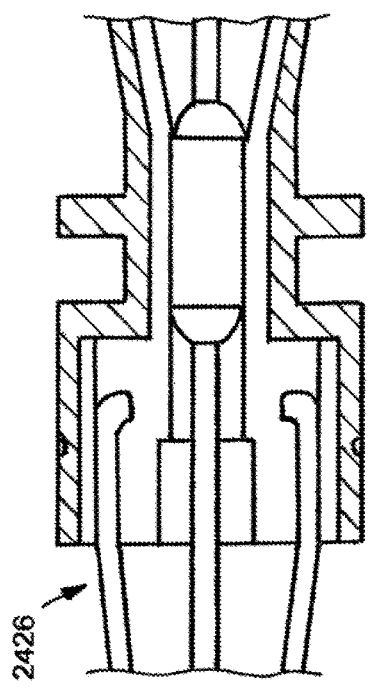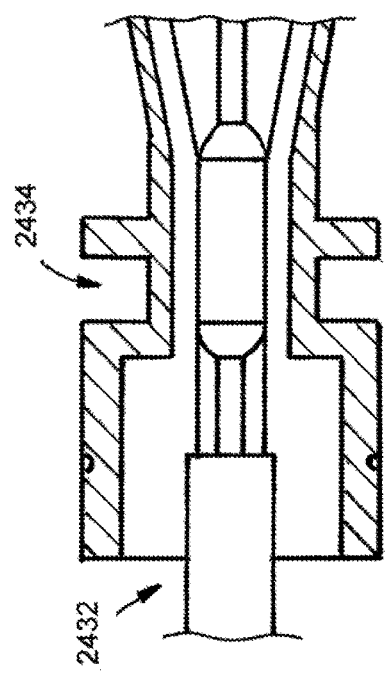

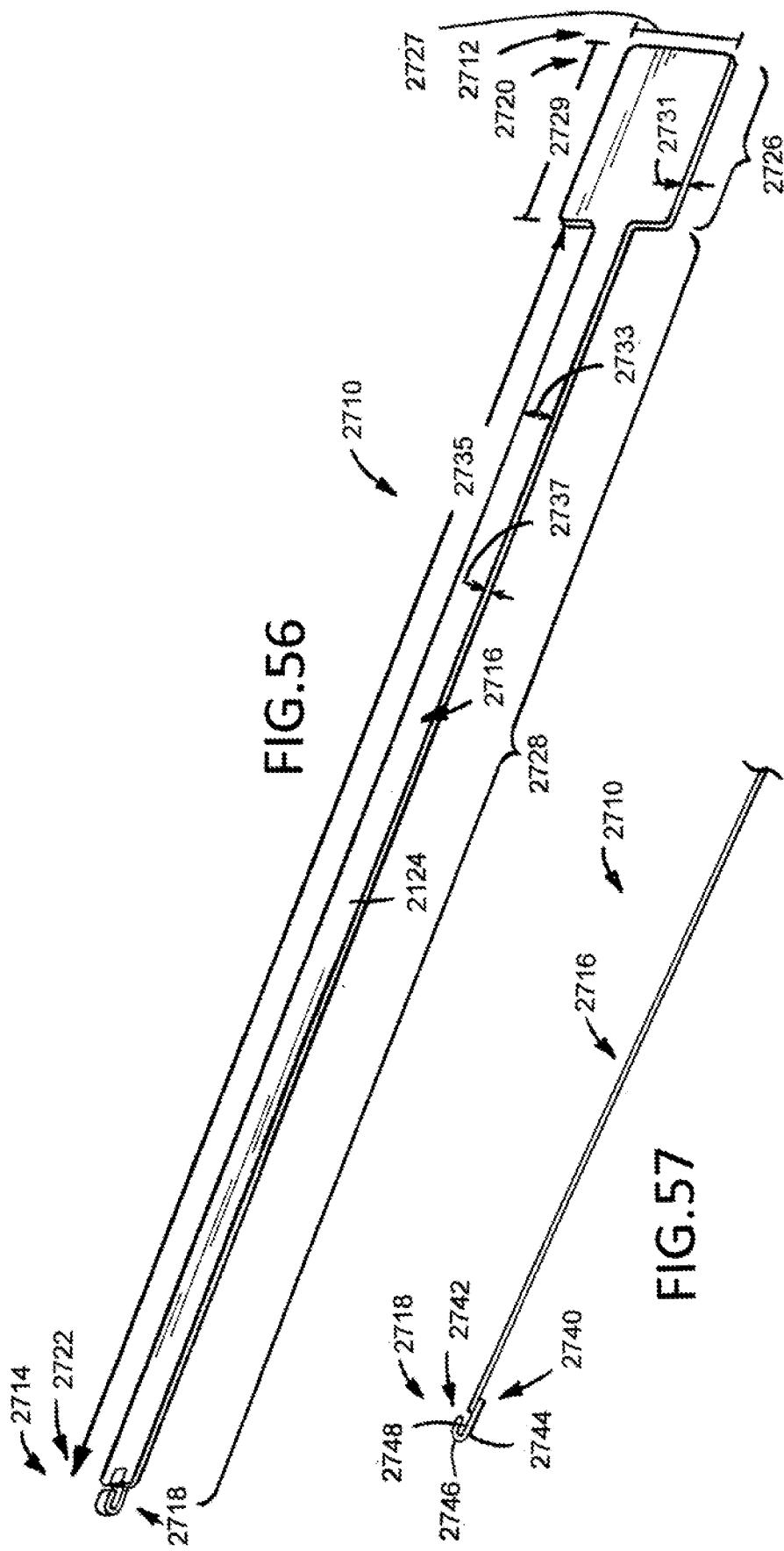

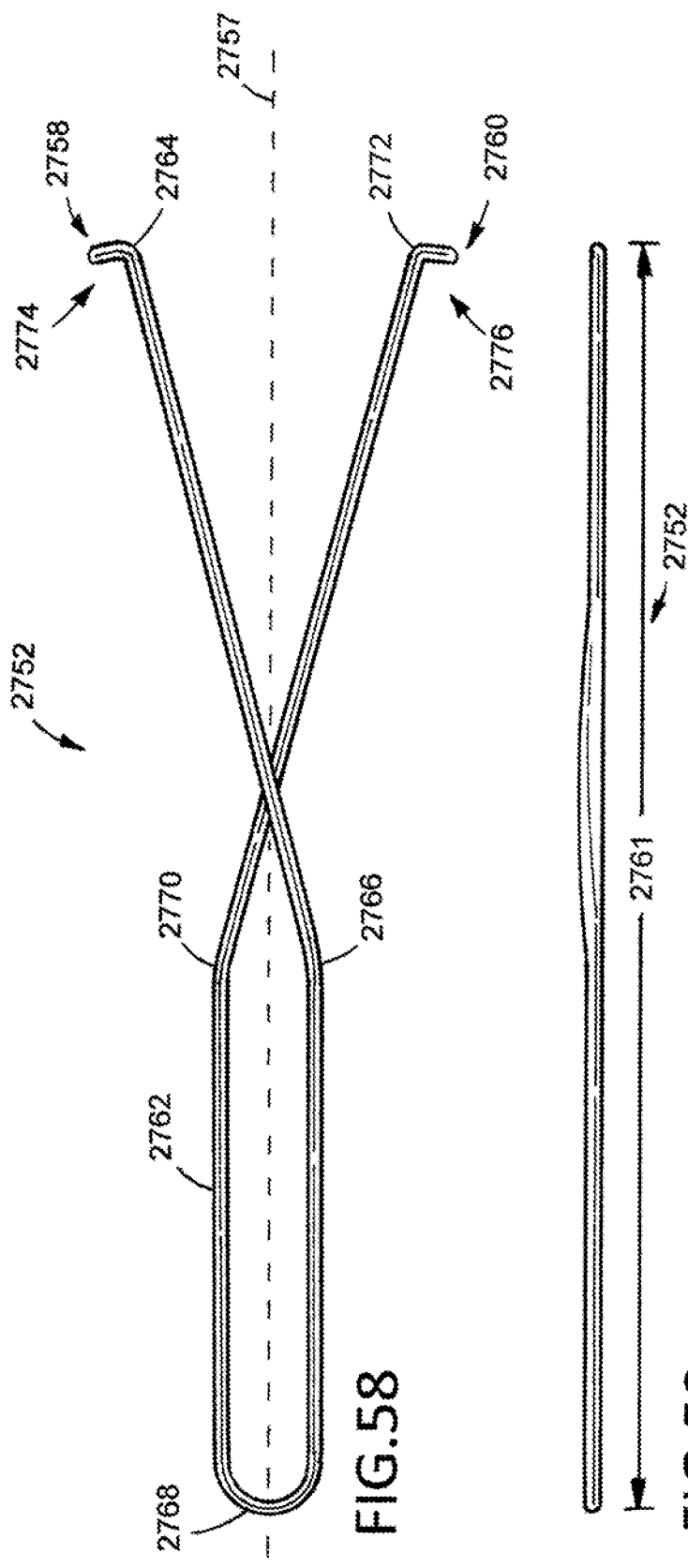

STORAGE DEVICES, LOADING DEVICES, DELIVERY SYSTEMS, KITS, AND ASSOCIATED METHODS

CROSS-REFERENCE TO RELATED APPLICATION

This application claims the benefit of U.S. Provisional Application No. 62/694,660, filed on Jul. 6, 2018. The entire disclosure of this related application is hereby incorporated by reference into this disclosure.

FIELD

The disclosure relates generally to the field of medical devices. More particularly, the disclosure relates to storage devices, loading devices, delivery systems, ancillary devices, kits, and associated methods for implantable medical devices.

BACKGROUND

Various implantable medical devices have been developed that provide a mechanism for treating various disorders. For example, one potential clinical application for an implantable valve is to treat chronic venous insufficiency, in which the natural valves in the veins of the lower extremities are incompetent, causing reflux, elevated venous pressures and reduced blood flow. Another clinical application for an implantable valve is to treat pulmonary insufficiency, which is a condition in which the pulmonary valve is incompetent and allows backflow from the pulmonary artery to the right ventricle of the heart. The implantable valve can include a mechanical construct and a graft material. In certain valve constructs, the valve graft material may require that the implantable valve be stored in a wet condition to maintain the integrity of the graft material. For example, the implantable valve can be stored in a chemical solution, such as glutaraldehyde, which requires that the solution be rinsed from the implantable valve prior to implantation. The need for rinsing is common practice in the bioprosthetic valve field. For example, when heart valves are stored in a solution, such as glutaraldehyde or formaldehyde, it is common practice that the valve be removed from a storage container, rinsed in bowls of saline at the patient's bedside, and loaded into the delivery system prior to the implant procedure, which increases the likelihood of contamination of the implantable medical device.

Therefore, a need exists for new and useful storage devices, loading devices, delivery systems, ancillary devices, kits, and associated methods.

SUMMARY OF SELECTED EXAMPLE EMBODIMENTS

Various storage devices, loading devices, delivery systems, kits, and methods are described herein.

An example storage device comprises a storage member, a first cap, and a second cap. The storage member has a first end, a second end, and a main body that defines a first opening, a second opening, a passageway, a separating wall, and a plurality of holes. The passageway extends from the first opening to the second opening and has a first portion and a second portion. The separating wall extends into the passageway at a location between the first end and the second end. The first portion of the passageway extends from the first end of the storage member to the separating wall and the second portion of the passageway extends from the second end of the storage member to the separating wall. The second portion is sized and configured to house an implantable medical device. Each hole of the plurality of holes extends through the separating wall and provides access between the first portion of the passageway and the second portion of the passageway. The first cap is releasably attached to the first end of the storage member. The second cap is releasably attached to the second end of the storage member.

An example loading device comprises a storage member, a first cap, a loading member, and a second cap. The storage member has a first end, a second end, and a main body that defines a first opening, a second opening, a passageway, a separating wall, and a plurality of holes. The passageway extends from the first opening to the second opening and has a first portion and a second portion. The separating wall extends into the passageway at a location between the first end and the second end. The first portion of the passageway extends from the first end of the storage member to the separating wall and the second portion of the passageway extends from the second end of the storage member to the separating wall. The second portion is sized and configured to house an implantable medical device. Each hole of the plurality of holes extends through the separating wall and provides access between the first portion of the passageway and the second portion of the passageway. The first cap is releasably attached to the first end of the storage member. The loading member is releasably attached to the second end of the storage member and has a first end, a second end, and a main body that defines a first opening, a second opening, and a passageway that extends from the first opening to the second opening. The passageway of the loading member has a first portion, a second portion, a third portion, and a fourth portion. The first portion of the passageway of the loading member extends from the first end of the loading member to the second portion of the passageway of the loading member and has a first inside diameter. The second portion of the passageway of the loading member extends from the first portion of the passageway of the loading member to the third portion of the passageway of the loading member and has a second inside diameter that tapers from the first portion of the passageway of the loading member to the third portion of the passageway of the loading member. The third portion of the passageway of the loading member extends from the second portion of the passageway of the loading member to the second end of the loading member and has a third inside diameter that is less than the first inside diameter of the first portion of the passageway of the loading member. The fourth portion of the passageway of the loading member extends from the third portion and has a width that is greater than the third inside diameter of the third portion of the passageway. The second cap is releasably attached to the second end of the loading member.

An example delivery system comprises a sheath, an elongate member, a tip, and a gripping member. The sheath has a first end, a second end, a length, and a main body that defines a lumen. The length of the sheath extends from the first end to the second end. The lumen extends through the entire length of the sheath. The elongate member has a lengthwise axis, a first end, a second end, and a main body that defines an outer surface, and a notch. The notch extends into the main body of the elongate member from the outer surface, toward the lengthwise axis, and toward the second end of the elongate member at an angle that is greater than 0 degrees relative to the lengthwise axis. The tip is disposed on the second end of the elongate member and has a first end and a second end. The gripping member is attached to the elongate member between the notch and the first end of the tip. The gripping member has a first end, a second end, a length, and a main body. The gripping member is sized and configured to be disposed within the sheath. The notch is disposed between the first end of the elongate member and the gripping member.

An example kit comprises a storage device, a device guard, a delivery system, and a loading member. The storage device comprises a storage member, a first cap, and a second cap. Another example kit comprises a loading device, a device guard, and a delivery system. The loading device comprises a storage member, a first cap, a loading member, and a second cap.

An example method of sterilizing an implantable medical device comprises: inserting an implantable medical device into a storage member; attaching a first cap to the storage member; introducing a sterilizing material into the storage member; introducing a holding material into the storage member such that the sterilizing material is removed from the storage member; attaching a second cap to the storage member.

An example method of storing an implantable medical device comprises: inserting a sterilized implantable medical device into a storage member; attaching a first cap to the storage member; introducing a holding material into the storage member; attaching a second cap to the storage member.

An example method of rinsing an implantable medical device comprises: attaching a device that includes a rinsing material to a one-way valve of a storage device; introducing the rinsing material into the storage device such that it passes through the storage device; stopping the step of introducing the rinsing material into the storage device.

An example method of loading an implantable medical device onto a delivery system comprises: removing a cap from a storage member containing an implantable medical device; removing a diffuser from the storage member; attaching a device guard to the storage member; removing a second cap; attaching the storage member to a loading member of a guide system; applying an axial force on a portion of a delivery system such that it is passed through the storage member and partially disposed within the device guard; positioning a loading puller within a notch defined by an elongate member of the delivery system; applying an axial force on the elongate member of the delivery system away from the storage member until the loading puller moves to its open configuration and is free of the implantable medical device; removing the loading puller from the delivery system and loading member; applying an axial force on a sheath of the delivery system toward the loading member while maintaining the position of the elongate member until the sheath contacts the loading member; applying an axial force on the elongate member while maintaining the position of the sheath such that the elongate member is withdrawn from the loading member and the medical device is advanced into the sheath; removing the delivery system from the loading member.

Another example method of loading an implantable medical device onto a delivery system comprises: removing a cap from a storage member containing an implantable medical device; removing a diffuser from the storage member; attaching a device guard to the storage member; applying an axial force on a portion of a delivery system such that it is passed through the storage member and partially disposed within the device guard; positioning a loading puller within a notch defined by an elongate member of the delivery system; applying an axial force on the elongate member of the delivery system until the loading puller moves to its open configuration and is free of the implantable medical device; removing the loading puller from the delivery system and loading member; applying an axial force on a sheath of the delivery system toward the loading member while maintaining the position of the elongate member until the sheath contacts the loading member; applying an axial force on the elongate member while maintaining the position of the sheath such that the elongate member is withdrawn from the loading member and the medical device is advanced into the sheath; removing the delivery system from the loading member.

Another example method of loading an implantable medical device onto a delivery system comprises: obtaining an implantable medical device with an attached loading puller; removing the implantable medical device and loading puller from the container; rinsing the implantable medical device and loading puller; advancing a loading assister through a passageway defined by a loading member; attaching the loading assister to the loading puller; withdrawing the loading assister from the loading member; removing the loading assister from the loading puller; attaching a device guard to the loading member; applying an axial force on an elongate member of a delivery system directed toward a loading member such that it is passed through the loading member and partially disposed within the device guard; positioning a loading puller within a notch defined by an elongate member of the delivery system; applying an axial force on the elongate member of the delivery system directed away from the loading member until the first and second ends of the loading puller are disposed within the fourth portion of the loading member; removing the loading puller from the delivery system and loading member; applying an axial force on a sheath of the delivery system directed toward the loading member while maintaining the position of the elongate member until the sheath contacts the loading member; applying an axial force on the elongate member directed away from the loading member while maintaining the position of the sheath such that the elongate member is withdrawn from the loading member and the medical device is advanced into the sheath; removing the delivery system from the loading member.

Additional understanding of the example storage devices, loading devices, delivery systems, ancillary devices, kits, and associated methods can be obtained by review of the detailed description, below, and the appended drawings.

BRIEF DESCRIPTION OF THE DRAWINGS

FIG. 27 is a partial elevation view of a first example delivery system.

FIG. 28 is a magnified view of area II-II illustrated in FIG. 27.

FIG. 29 is a partial elevation view of a second example delivery system.

FIG. 30 is a partial perspective view of a third example delivery system.

FIG. 32A is a perspective view of another alternative tip that can be included on an elongate member of a delivery system.

FIG. 32B is an end view of the tip illustrated in FIG. 32A.

FIG. 32C is a perspective view of an alternative device guard that can be included on a storage device or loading device.

FIG. 32D is an end view of the device guard illustrated in FIG. 32C.

FIG. 46A is a magnified view of area III-III illustrated in FIG. 46.

FIG. 47A is a magnified view of area IV-IV illustrated in FIG. 47.

FIG. 48A is a magnified view of area V-V illustrated in FIG. 48.

FIG. 49A is a magnified view of area VI-VI illustrated in FIG. 49.

FIG. 51A is a magnified view of area VII-VII illustrated in FIG. 51.

FIG. 52A is a magnified view of area VIII-VIII illustrated in FIG. 52.

FIG. 53A is a magnified view of area IX-IX illustrated in FIG. 53.

FIG. 56 is a perspective view of an example loading assister.

FIG. 57 is a partial elevation view of the loading assister illustrated in FIG. 56.

FIG. 58 a top view of another example loading puller.

FIG. 59 is an elevation view of the loading puller illustrated in FIG. 58.

DETAILED DESCRIPTION

The following detailed description and the appended drawings describe and illustrate various example embodiments of storage devices, loading devices, delivery systems, ancillary devices, kits, and methods. The description and illustration of these examples are provided to enable one skilled in the art to make and use a storage device, a loading device, a delivery system, an ancillary device, to make a kit, and to practice a method. They are not intended to limit the scope of the claims in any manner.

As used herein, the term "diameter" refers to the length of a straight line passing from side to side through the center of a body, element, or feature, and does not impart any structural configuration on the body, element, or feature.

As used herein, the term "circumferential" refers to an enclosing boundary of a body, element, or feature, and does not impart any structural configuration on the body, element, or feature.

Figure 1:
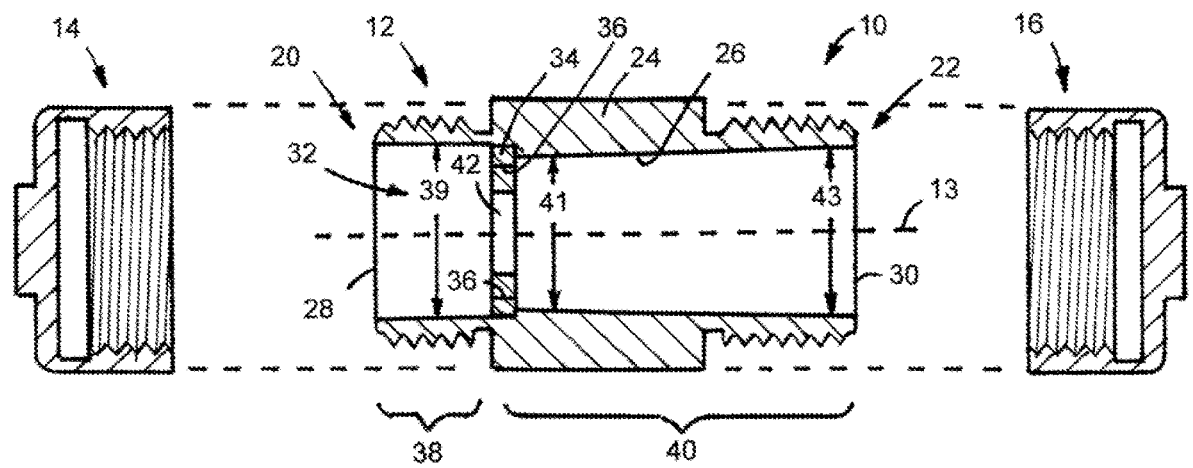
FIG. 1 is an exploded cross-sectional view of a first example storage device taken along the lengthwise axis of the storage member.
Figure 2:
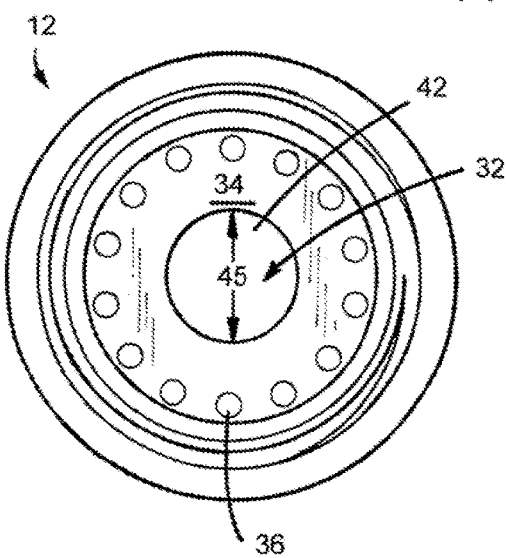
FIG. 2 is an end view of the storage member illustrated in FIG. 1.
Figure 3:
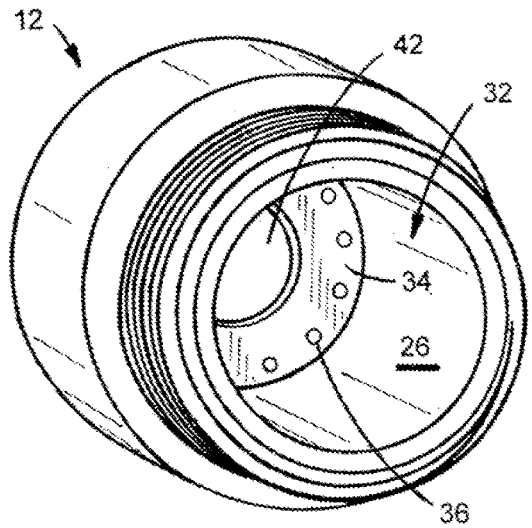
FIG. 3 is a perspective view of the storage member illustrated in FIG. 1.

FIGS. 1, 2, and 3 illustrate a first example storage device 10 that includes a storage member 12, a first cap 14, and a second cap 16. In the illustrated embodiment, each of the first cap 14 and the second cap 16 is releasably attached to the storage member 12.

The storage member 12 has a lengthwise axis 13, a first end 20, a second end 22, and a main body 24 that defines a circumferential wall 26, a first opening 28, a second opening 30, a passageway 32, a separating wall 34, and a plurality of holes 36. The passageway 32 extends through the storage member 12 from the first opening 28 to the second opening 30 and has a first portion 38 that extends from the first end 20 to the separating wall 34 and a second portion 40 that extends from the second end 22 to the separating wall 34. The first portion 38 has a first inside diameter 39. The second portion 40 has a second inside diameter 41 at the separating wall 34 that is less than the first inside diameter 39 and a third inside diameter 43 at the second end 22 that is equal to the first inside diameter 39 such that the second portion 40 tapers from the second end 22 to the separating wall 34 (e.g., creating a partial cone). In the illustrated embodiment, the second portion 40 is sized and configured to house an implantable medical device, as described in more detail herein. The separating wall 34 extends into the passageway 32 at a location between the first end 20 and the second end 22 that is positioned closer to the first end 20. The separating wall 34 defines a through hole 42 that has inside diameter 45 that is less than the second inside diameter 41 of the second portion 40. Each hole of the plurality of holes 36 extends through the separating wall 34 and provides access between the first portion 38 of the passageway 32 and the second portion 40 of the passageway 32 such that a fluid passed through the storage member 12 can pass through the through hole 42 and/or the plurality of holes 36 over the outside and inside surfaces of a medical device disposed within the second portion of the passageway 40. Each hole of the plurality of holes 36 is equally spaced from an adjacent hole of the plurality of holes 36 and is disposed the same distance from the circumferential wall 26 relative to the other holes of the plurality of holes 36.

While the storage member 12 has been illustrated as having a particular structural arrangement, a storage member can have any suitable structural arrangement and selection of a suitable structural arrangement for a storage member can be based on various considerations, including the type of implantable medical device intended to be stored within the storage member. For example, while the passageway 32 has been illustrated as having a first portion 38 and a second portion 40, a passageway defined by a main body of a storage member can have any suitable number of portions, such as one, at least one, two, a plurality, three, four, and any other number considered suitable for a particular embodiment. While the second portion 40 has been illustrated as having a second inside diameter 41 at the separating wall 34 that is less than the first inside diameter 39 and a third inside diameter 43 at the second end 22 that is equal to the first inside diameter 39, a second portion can have any suitable inside diameters. For example, a second portion can have a second inside diameter at the separating wall that is equal to, less than, greater than, or about a first inside diameter of a first portion and/or a third inside diameter at a second end that is equal to, less than, greater than, or about the first inside diameter. While the separating wall 34 has been illustrated as positioned closer to the first end 20, a separating wall can be positioned at any suitable location between the first and second ends of a storage member. For example, a separating wall can be disposed in the center of a storage member between first and second ends, or positioned closer to a second end of a storage member. While the storage member 12 has been illustrated as defining a plurality of holes 36 such that each hole of the plurality of holes 36 is equally spaced from an adjacent hole of the plurality of holes 36 and is disposed the same distance from the circumferential wall 26 relative to the other holes of the plurality of holes 36, a storage member can include any suitable number of holes positioned in any suitable orientation. Examples of numbers of holes considered suitable for a main body of a storage member to define on a separating wall include one, at least one, two, a plurality, three, four, five, more than five, more than ten, and any other number considered suitable for a particular embodiment. Examples of positions considered suitable to locate a plurality of holes include such that each hole of a plurality of holes is equally spaced, or irregularly spaced, from an adjacent hole of the plurality of holes and is disposed the same distance, or a varied distance, from a circumferential wall relative to the other holes of the plurality of holes.

Each of the first cap 14 and the second cap 16 is sized and configured to be releasably attached to the storage member 12. The first cap 14 is releasably attached to the first end 20 of the storage member 12 and the second cap 16 is releasably attached to the second end 22 of the storage member. When attached to the storage member 12, each of the first cap 14 and the second cap 16 seals the passageway 32 defined by the storage member 12. In the illustrated embodiment, each of the first cap 14 and the second cap 16 defines threads that mate with threads defined by the storage member 12 to achieve releasable attachment between the storage member 12 and the first and second caps 14, 16.

While the first cap 14 has been illustrated as being threadably attached to the storage member 12 and the second cap 16 has been illustrated as being threadably attached to the storage member 12, a first cap and a second cap can be attached to a storage member using any suitable technique or method of attachment and selection of a suitable technique or method of attachment between the cap and a storage member can be based on various considerations, including the material(s) that forms the cap and/or storage member. Examples of techniques and methods of attachment considered suitable between a cap and a storage member, between a storage member and any other component, between a loading member and any other component, and/or between any two components described herein include using threaded connections, threaded connections using a thread disposed on an exterior surface of a storage member to avoid rotation of the storage member (e.g., to avoid disruption of an implantable medical device stored in the storage device during attachment of a cap), snap fit attachments, using one or more connectors, one or more mating slots and projections, one or more sealed unions, tapered attachments (e.g., morse taper), and any other technique or method of attachment considered suitable for a particular application.

Figure 4:
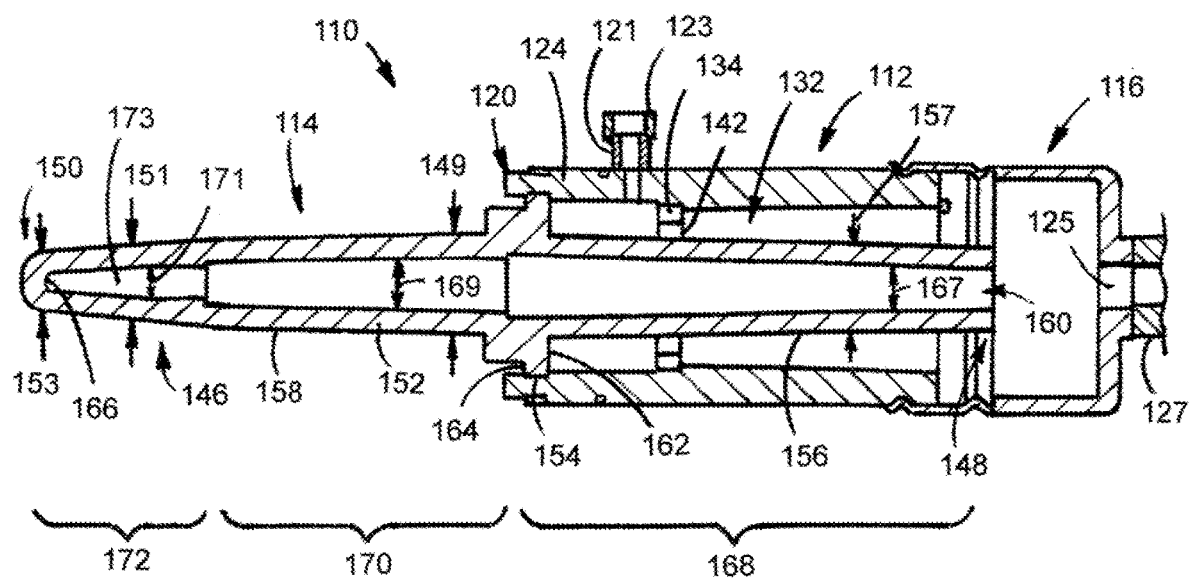
FIG. 4 is a partial cross-sectional view of a second example storage device taken along the lengthwise axis of the storage member.
Figure 5:
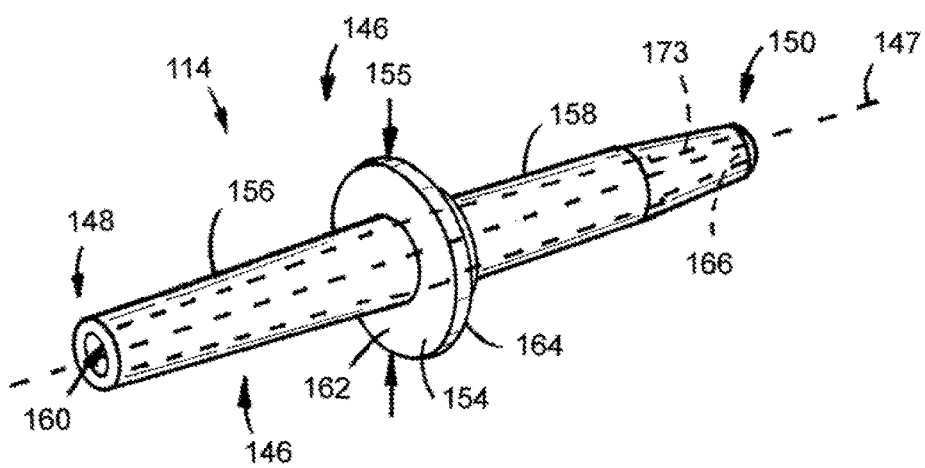
FIG. 5 is a perspective view of the device guard illustrated in FIG. 4.

FIGS. 4 and 5 illustrate another example storage device 110. The storage device 110 is similar to the storage device 10 illustrated in FIGS. 1, 2, and 3 and described above, except as detailed below. The storage device 110 includes a storage member 112, a first cap 114, and a second cap 116. In the illustrated embodiment, each of the first cap 114 and the second cap 116 defines structure that mates with structure defined by the storage member 112 to achieve a releasable snap fit attachment between the storage member 112 and the first and second caps 114, 116.

In the illustrated embodiment, the storage member 112 includes a port 121 extending from the main body 124 and a first two-way valve 123 attached to the port 121. In addition, the second cap 116 defines a passageway 125 that extends through the main body of the second cap 116 that is in communication with a second two-way valve 127. This structural arrangement provides a mechanism for sterilizing and/or rinsing an implantable medical device stored in the storage device 110, decreasing the complexity of sterilizing, storing, rinsing, and/or loading an implantable medical device, and minimizing the risk associated with handling an implantable medical device that is intended to be positioned within the storage device. In an alternative embodiment, the port 121, the first two-way valve 123, the passageway 125, and/or the second two-way valve 127 can be omitted.

In the illustrated embodiment, the first cap 114 comprises a device guard 146 that is releasably attached to the first end 120 of the storage member 112 and partially extends into the passageway 132 defined by the storage member 112. The device guard 146 has a lengthwise axis 147, a first end 148, a second end 150, and a main body 152 that defines a base 154, a first projection 156, a second projection 158, and a recess 160. The base 154 is disposed between the first end 148 and the second end 150 and is sized and configured to be releasably attached within the passageway 132 of the storage member 112. In the illustrated embodiment, the base 154 has an outside diameter 155, a first side 162, a second side 164, and is sized and configured to be releasably attached to the storage member 112 within the passageway 132 using a snap fit attachment between the device guard 146 and the storage member 112. Thus, the storage member 112 and the device guard 146 define mating structure that achieves a releasable snap fit attachment between the storage member 112 and the device guard 146.

The first projection 156 extends from the first side 162 to the first end 148 and the second projection 158 extends from the second side 164 to the second end 150. The first projection 156 has an outside diameter 157 that tapers from the base 154 to the first end 148, which provides a mechanism for positioning an implantable medical device between the first projection 156 and the storage member 112. The second projection 158 has a first outside diameter 149 at the base 154, a second outside diameter 151 between the base 154 and the second end 150, and a third outside diameter 153 at the second end 150. The second outside diameter 151 is less than the first outside diameter 149 and the third outside diameter 153 is less than the second outside diameter 151. The recess 160 extends from the first end 148 toward the second end 150 to a recess base 166 and is sized and configured to receive a portion of a delivery system, as described in more detail herein. The recess 160 has a first portion 168, a second portion 170, and a third portion 172. The first portion 168 has an inside diameter 167 that increases from the first end 148 to the second portion 170. The second portion 170 has an inside diameter 169 that tapers from the first portion 168 to the third portion 172. The third portion 172 has an inside diameter 171 that is less than the inside diameter 169 of the second portion 170. Each of the first portion 168 and the second portion 170 has a partial conical configuration and the third portion 172 is sized and configured to mate with a portion of a delivery system (e.g., tip 1516) such that the portion of the delivery system is rotationally fixed relative to the device guard 146 when disposed within the third portion 172, as described in more detail herein. In the illustrated embodiment, the third portion 172 defines a planar surface 173 that extends from the second portion 170 to the recess base 166 that is sized and configured to mate with a portion of a tip (e.g., planar surface 1572 of tip 1516) of a delivery system, as described in more detail herein. When attached to the storage member 112, the device guard 146 is positioned such that the first projection 156 extends through the through hole 142 of the separating wall 134. During use, the device guard 146 acts as a mechanical stop to advancement of a delivery system through a storage member, as described in more detail herein.

While the device guard 146 has been illustrated as having a particular structural arrangement, a device guard can have any suitable structural arrangement and selection of a suitable structural arrangement for a device guard can be based on various considerations, including the type of implantable medical device intended to be implanted using a storage device of which the device guard is a component. For example, while the device guard 146 has been illustrated as a single component, a device guard can be formed as multiple components (e.g., base, first projection, second projection) releasably attached, or fixedly attached, to one another, a first projection can have a constant outside diameter along its length, a second projection can have a constant outside diameter along its length, and/or a first portion can have an inside diameter that is constant from first end to second portion. While each of the first portion 168 and the second portion 170 has been illustrated as having a partial conical configuration and the third portion 172 has been illustrated as having a planar surface 173 that extends from the second portion 170 to the recess base 166, a recess defined by a device guard can have any suitable configuration. For example, a recess can define any structural arrangement that is sized and configured to receive any suitable portion of a delivery system (e.g., portion of a tip, entire tip) and/or rotationally fix a portion of a delivery system relative to the device guard when disposed within the device guard. While device guard 146 has been illustrated as being releasably attached to storage member 112, any suitable device guard, such as those described herein (e.g., device guard 715, device guard 1714), can be releasably attached to a storage member.

Figure 6:
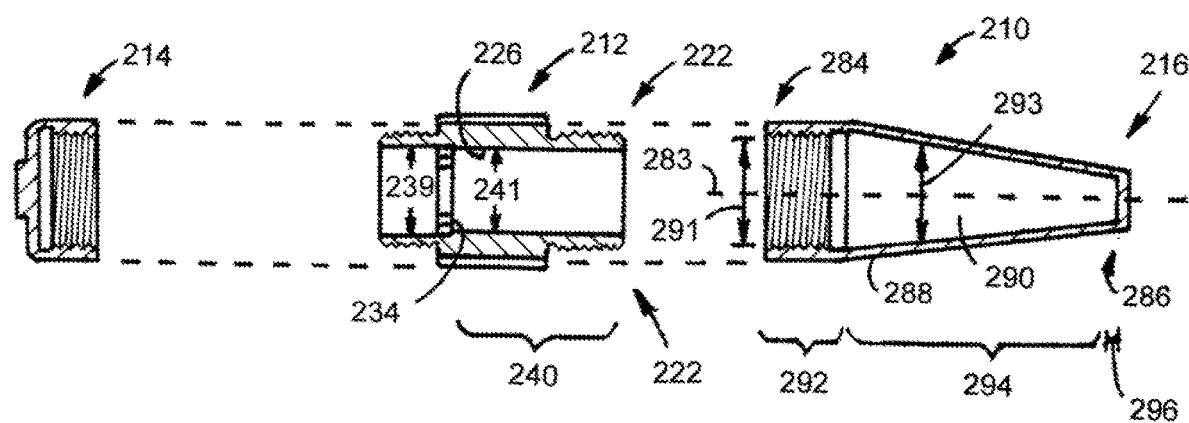
FIG. 6 is an exploded cross-sectional view of a third example storage device taken along the lengthwise axis of the storage member.
Figure 7:
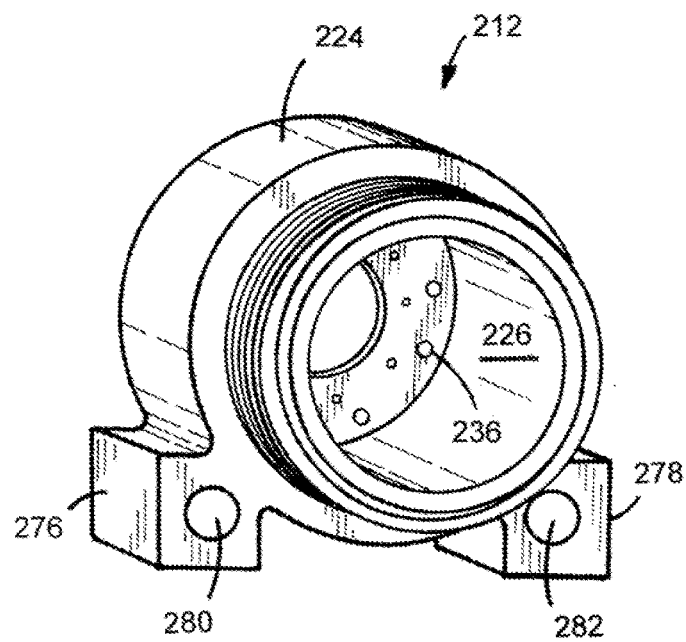
FIG. 7 is a perspective view of the storage member illustrated in FIG. 6.
Figure 8:
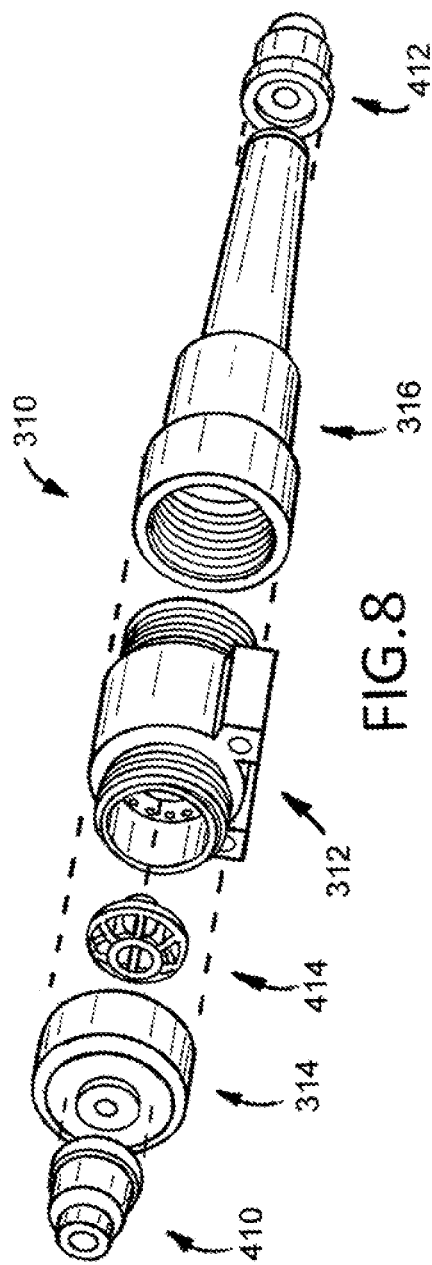
FIG. 8 is an exploded perspective view of a fourth example storage device.
Figure 9:
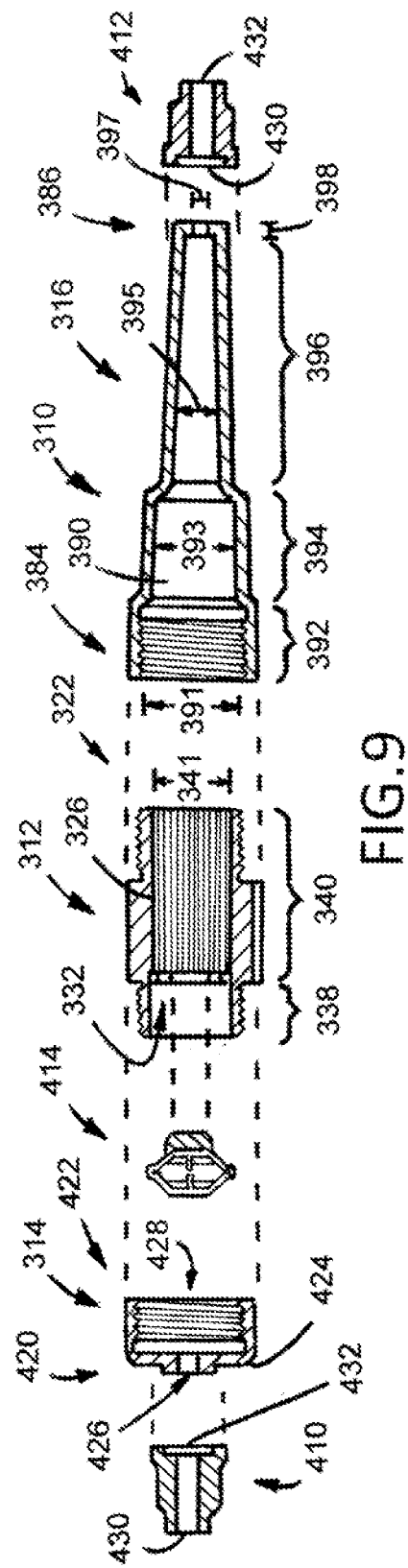
FIG. 9 is an exploded cross-sectional view of the storage device illustrated in FIG. 8 taken along the lengthwise axis of the storage member.
Figure 10:
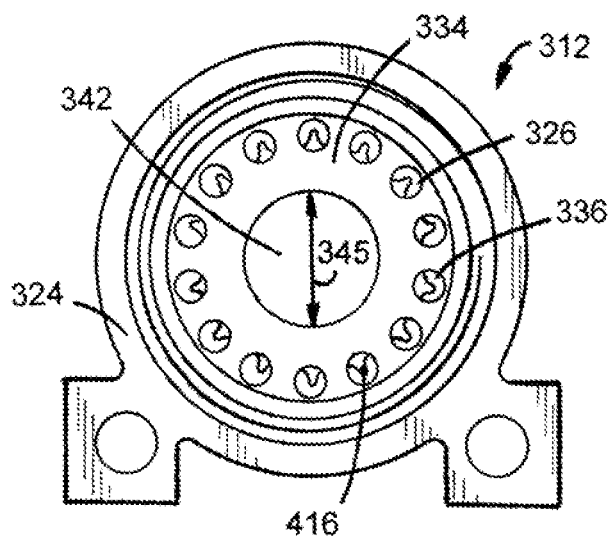
FIG. 10 is an end view of the storage member illustrated in FIG. 8.
Figure 11:
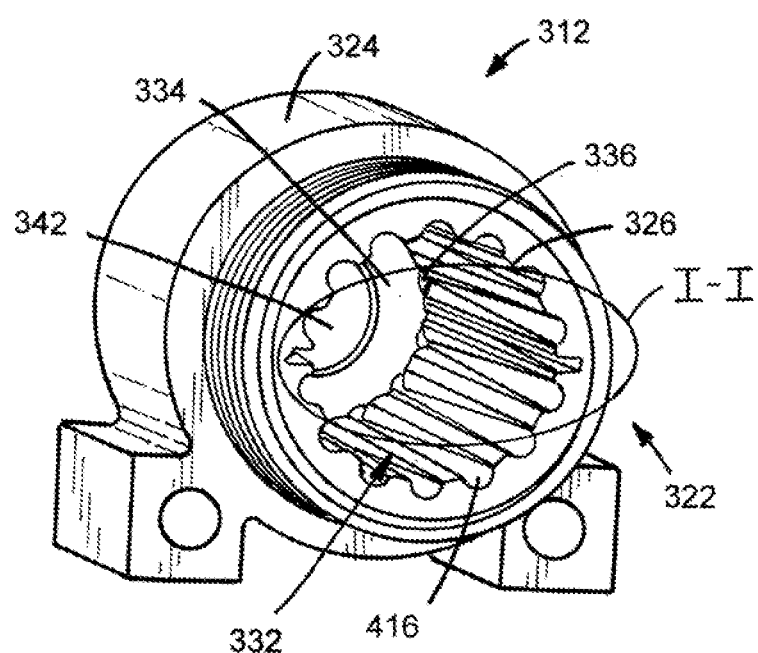
FIG. 11 is a perspective view of the storage member illustrated in FIG. 8.
Figure 12:
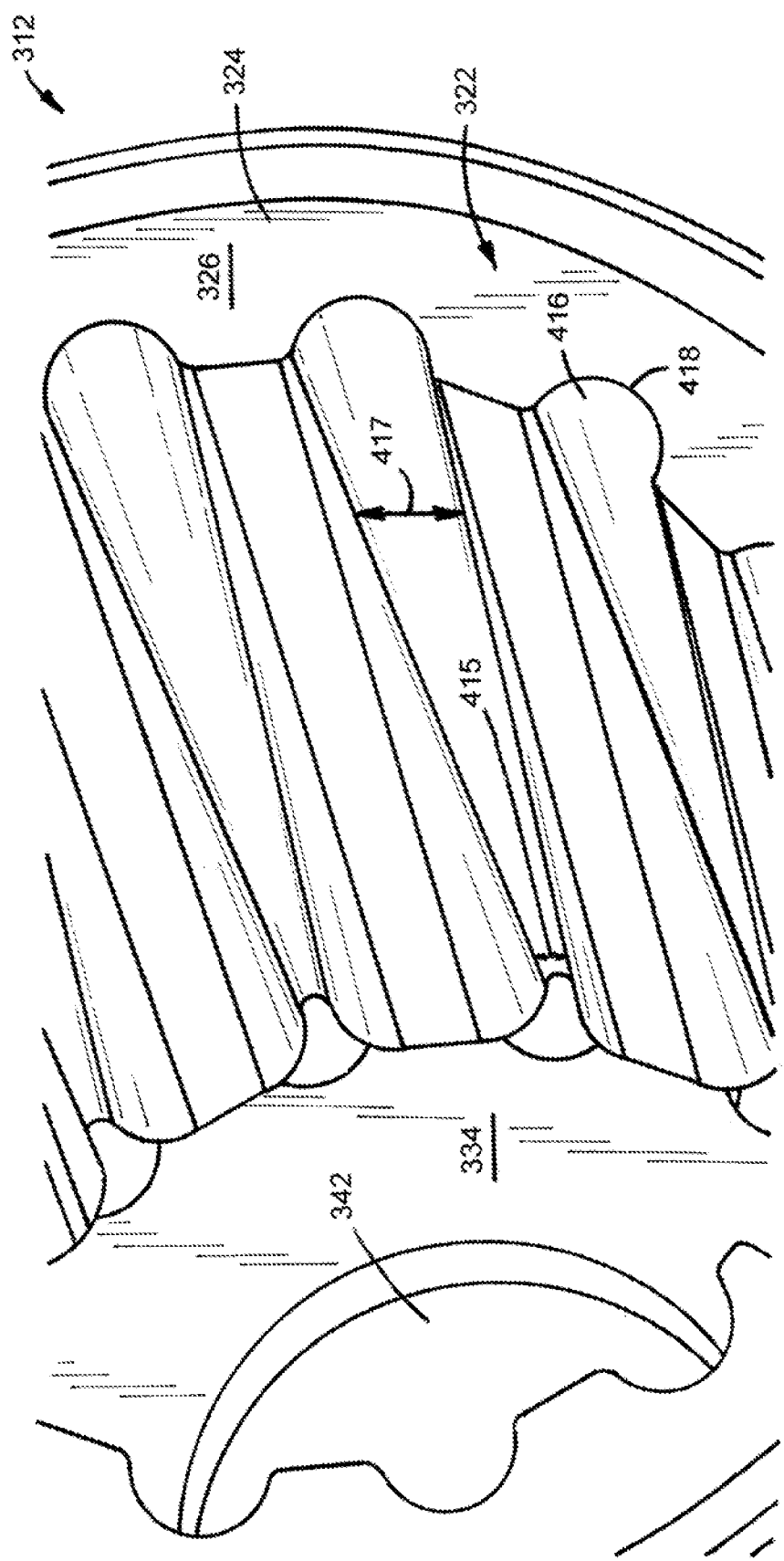
FIG. 12 is a magnified view of area I-I illustrated in FIG. 11.

FIGS. 6 and 7 illustrate another example storage device 210. The storage device 210 is similar to the storage device 10 illustrated in FIGS. 1, 2, and 3 and described above, except as detailed below. The storage device 210 includes a storage member 212, a first cap 214, and a second cap 216.

In the illustrated embodiment, the second portion 240 has a second inside diameter 241 at the separating wall 234 that is equal to the first inside diameter 239 such that the second portion 240 has a constant inside diameter 241 from the separating wall 234 to the second end 222 (e.g., creating a cylinder). In addition, each hole of the plurality of holes 236 defined by the main body 224 of the storage member 212 is not equally spaced from an adjacent hole of the plurality of holes 236 and is disposed a different distance from the circumferential wall 226 relative to the other holes of the plurality of holes 236. The main body 224 of the storage member 212 defines first and second projections 276, 278 that extend from the circumferential wall 226, a first passageway 280 that extends through the first projection 276, and a second passageway 282 that extends through the second projection 278. The projections 276, 278 and the passageways 280, 282 are sized and configured to mate with a loading member and/or guide member, as described in more detail herein, such that the storage member 212 can be releasably attached to the loading member and/or guide member. While the storage member 212 has been illustrated as including a specific structural arrangement to accomplish releasable attachment to a loading member and/or guide member, any suitable structure can be used to accomplish such a releasable attachment. Any embodiment of a storage member described herein can optionally include one or more projections (e.g., projections 276, 278) and one or more passageways (e.g., passageways 280, 282) such that the storage member can releasably attached to a loading member and/or guide member and be used with a guide system, as described in more detail herein.

In the illustrated embodiment, the second cap 216 is releasably attached to the second end 222 of the storage member 212. The second cap 216 has a lengthwise axis 283, a first end 284, a second end 286, and a main body 288 that defines a recess 290 that extends into the second cap 216. The recess 290 has a first portion 292, a second portion 294, and extends to a recess base 296. The first portion 292 extends from the first end 284 toward the second end 286 and has a first inside diameter 291. The second portion 294 extends from the first portion 292 to the recess base 296 and has a second inside diameter 293 that tapers from the first portion 292 to the recess base 296.

FIGS. 8, 9, 10, 11, 12, 13, and 14 illustrate another example storage device 310. The storage device 310 is similar to the storage device 210 illustrated in FIGS. 6 and 7 and described above, except as detailed below. The storage device 310 includes a storage member 312, a first cap 314, a second cap 316, a first one-way valve 410, a second one-way valve 412, and a diffuser 414.

In the illustrated embodiment, the inside diameter of the second portion 340 of the storage member 312 has a second inside diameter 341 at the separating wall 334 that positions the circumferential wall 326 in the second portion 340 of the passageway 332 such that it partially obstructs the plurality of holes 336. As shown FIGS. 10, 11, and 12 the main body 324 of the storage member 312 defines a plurality of recesses 416. Each recess of the plurality of recesses 416 extends into the circumferential wall 326 to a recess base 418 and extends from the separating wall 334 toward the second end 322. In the illustrated embodiment, each recess of the plurality of recesses 416 extends to the second end 322. Each recess of the plurality of recesses 416 is in communication with a hole of the plurality of holes 336 and has a first width 415 at the separating wall 334 at the recess base 418 and a second width 417 between the separating wall 334 and the second end 322 at the recess base 418 that is greater than the first width 415. By positioning each recess of the plurality of recesses 416 such that it is adjacent to and in communication with a hole of the plurality of holes 336, fluid passed through the storage member 312 from the first one-way valve 410 toward the second one-way valve 412 can flow through the plurality of holes 336 and within the plurality of recesses 416 to increase the amount of fluid that contacts any implantable medical device disposed within the storage member 312. The through hole 342 defined by the main body 324 of the storage member 312 is sized and configured to receive a portion of the diffuser 414, as described in more detail herein.

While each recess of the plurality of recesses 416 has been illustrated as extending from the separating wall 334 to the second 322, as being in communication with a hole of the plurality of holes 336, and having a first width 415 at the separating wall 334 at the recess base 418 and a second width 417 between the separating wall 334 and the second end 322 at the recess base 418 that is greater than the first width 415, each recess can have any suitable structural arrangement. Selection of a suitable structural arrangement for each recess included in a storage member can be based on various considerations, including the structural arrangement of an implantable medical device intended to be disposed within the storage member. For example, a storage member can define any suitable number of recesses, such as one, at least one, two, a plurality, three, four, five, more than five, more than ten, and any other number considered suitable for a particular embodiment. A recess included on a storage member can extend any suitable length of a storage member. For example, a recess, or each recess of a plurality of recesses, can extend from a separating wall to a second end of a storage member, from a separating wall to a location between the separating wall and the second end, from a location between a separating wall and a second end to the second end, from a first location between a separating wall and a second end to a second location between the first location and the second end, and any other length of a storage member considered suitable for a particular embodiment. A recess included on a storage member can have any suitable width along its length. For example, a recess, or each recess of a plurality of recesses, can have a first width at a first end (e.g., at a separating wall) at a recess base and a second width at a second end (e.g., between a separating wall and a second end) at a recess base that is greater than, less than, equal to, or about the first width. A recess included on a storage member can have any suitable structural arrangement, such as curved, cuboidal, prismatic, and any other structural arrangement considered suitable for a particular embodiment.

In the illustrated embodiment, the second cap 316 is releasably attached to the second end 322 of the storage member 312. The passageway 390 of the second cap 316 has a first portion 392, a second portion 394, a third portion 396, and a fourth portion 398. The first portion 392 extends from the first end 384 toward the second end 386 and has a first inside diameter 391. The second portion 394 extends from the first portion 392 to the third portion 396 and has a second inside diameter 393 that tapers from the first portion 392 to the third portion 396. The third portion 396 extends from the second portion 394 to the fourth portion 398 and has an inside diameter 395 that tapers from the second portion 394 to the fourth portion 398. The fourth portion 398 extends from the third portion 396 to the second end 386 and has an inside diameter 397 that is sized and configured to allow fluid to pass through the passageway 390 to the second one-way valve 412, as described in more detail herein.

In the illustrated embodiment, the first cap 314 has a first end 420, a second end 422, and a main body 424 that defines a passageway 426 and a recess 428. The passageway 426 extends from the first end 420 to the recess 428 and is sized and configured to allow fluid to pass through the passageway 426. The first one-way valve 410 is releasably attached to the first end 420 of the first cap 314 and the second one-way valve 412 is releasably attached to the second end 386 of the second cap 316. Each of the first and second one-way valves 410, 412 has a first opening 430, a second opening 432, and is adapted to allow fluid to pass through the valve in one direction. In the illustrated embodiment, the first one-way valve 410 is adapted to allow fluid to pass through the valve from the first opening 430 to the second opening 432 and the second one-way valve 412 is adapted to allow fluid to pass through the valve from the second opening 432 to the first opening 430. Alternatively, a first one-way valve can be adapted to allow fluid to pass through the valve from a first opening to a second opening, or from a second opening to a first opening, and/or a second one-way valve can be adapted to allow fluid to pass through the valve from a first opening to a second opening, or from a second opening to a first opening. In alternative embodiments, a first one-way valve and/or second one-way valve can be omitted from a storage device and/or loading device, as described in more detail herein, and a first cap can define a recess and omit the inclusion of a passageway, a second cap can define a recess and omit the inclusion of a passageway, and/or a loading member can define a recess and omit the inclusion of a passageway. Alternatively, a first one-way valve and/or second one-way valve can be omitted from a storage device and/or loading device, as described in more detail herein, and a cap can be disposed on a first end of a first cap, a second end of a second cap, and/or a second end of a loading member to seal the passageway defined by the first cap, the passageway defined by the second cap, and/or the passageway defined by the loading member such that fluid cannot pass through the passageway(s). Alternatively, a first one-way valve and/or second one-way valve can be omitted from a storage device and/or loading device, as described in more detail herein, and a first two-way valve and/or second two-way valve can be included in the storage device and/or loading device in place of any one-way valves. Alternatively, a first one-way valve and/or second one-way valve included in a storage device can be permanently fixed to a cap, disposed within a recess defined by a cap, or other component, of the storage device.

Figure 13:
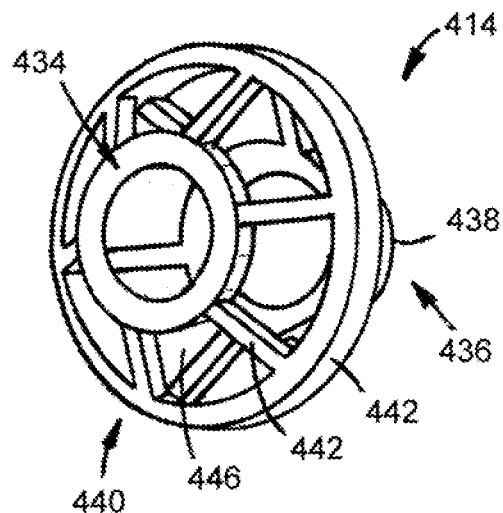
FIG. 13 is a perspective view of the diffuser illustrated in FIG. 8.
Figure 14:
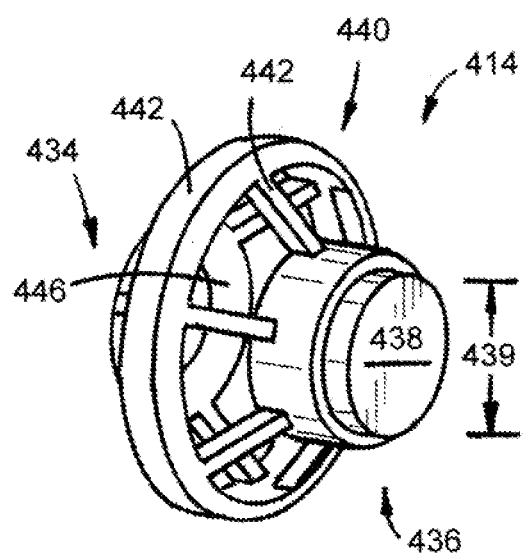
FIG. 14 is another perspective view of the diffuser illustrated in FIG. 8.

The diffuser 414 is releasably disposed within the first portion 338 of the passageway 332 and the through hole 342 of the separating wall 334. As shown in FIGS. 13 and 14, the diffuser 414 has a first end 434, a second end 436, a base 438, and a frame 440. The base 438 extends from the second end 436 toward the first end 434 to the frame 440 and is sized and configured to be received by the through hole 342 of the separating wall 334. The base 438 has an outside diameter 439 that is equal to the inside diameter 345 of the through hole 342 (e.g., such that the diffuser seals the through hole 342). Alternative embodiments, however, can include a diffuser that has a base with an outside diameter that is less than, greater than, or about, an inside diameter of a through hole. The storage member 312 and the diffuser 414 define mating structure that achieves a snap-fit attachment between the base 438 of the diffuser 414 and the separating wall 334 of the storage member 312. The frame 440 extends from the base 438 to the first end 434 and has a plurality of struts 442 that define a plurality of openings 446 that are sized and configured to allow a fluid to pass through the frame 432 during use. The diffuser 414 provides a mechanism for dispersing a fluid passed through the storage member 312 during use such that the fluid can pass through the plurality of holes 336 and/or through the through hole 342 in embodiments in which the base 438 of the diffuser 414 does not seal the through hole 342. In alternative embodiments, a diffuser can be omitted from a storage device and/or loading device, as described in more detail herein.

While the diffuser 414 has been illustrated as having a particular structural arrangement and as being releasably disposed within a first portion of a storage member, a diffuser can have any suitable structural arrangement and can be positioned within a storage member at any suitable location. Selection of a suitable structural arrangement for a diffuser and of a suitable location to position a diffuser within a storage member can be based on various considerations, including the structural arrangement of a storage member within which the diffuser is disposed. Examples of suitable locations for positioning a diffuser within a storage member include such that a diffuser is releasably disposed within a first portion of a storage device, releasably disposed within a second portion of a storage device, permanently, or releasably, attached to a cap (e.g., first cap, second cap) of a storage device, permanently, or releasably, attached to a storage member (e.g., within a first portion of a passageway, within a second portion of a passageway), and any other location considered suitable for a particular embodiment.

The storage device 310 provides a mechanism for decreasing the complexity of sterilizing, storing, rinsing, and/or loading an implantable medical device and minimizing the risk associated with handling an implantable medical device that is intended for implantation. For example, the storage device 310 provides a mechanism for sterilizing, storing, rinsing, and/or loading an implantable medical device using a closed system that reduces the interaction with the implantable medical device during sterilization, storing, rinsing, and/or loading.

Figure 15:
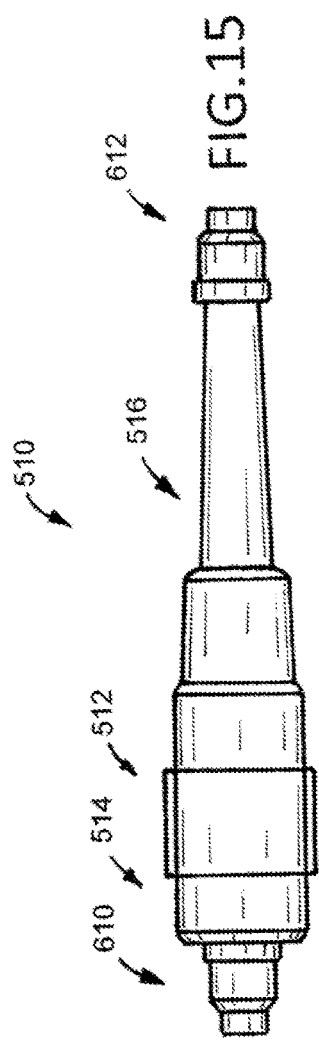
FIG. 15 is an elevation view of a fifth example storage device.
Figure 16:
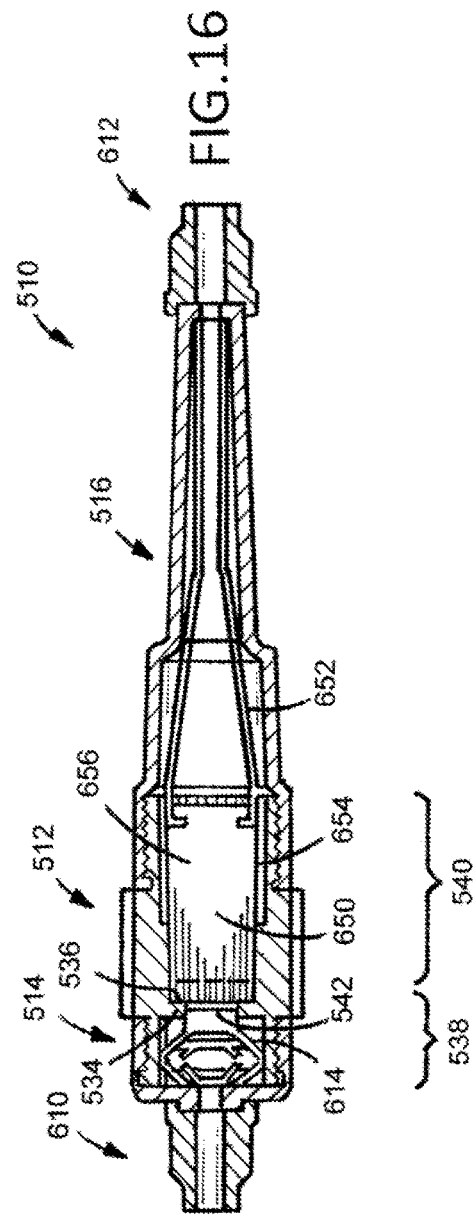
FIG. 16 is a cross-sectional view of the storage device illustrated in FIG. 15 taken along the lengthwise axis of the storage member.
Figure 16A:
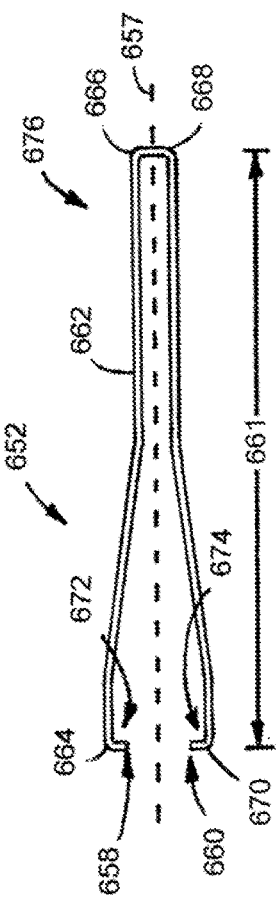
FIG. 16A is a top view of the loading puller illustrated in FIG. 16.

FIGS. 15, 16, and 16A illustrate another example storage device 510. The storage device 510 is similar to the storage device 310 illustrated in FIGS. 8, 9, 10, 11, 12, 13, and 14 and described above, except as detailed below. The storage device 510 includes a storage member 512, a first cap 514, a second cap 516, a first one-way valve 610, a second one-way valve 612, a diffuser 614, an implantable medical device 650, and a loading puller 652.

In the illustrated embodiment, the implantable member device 650 comprises a frame 654 and a material 656 attached to the frame 654. The implantable medical device 650 is disposed within the second portion 540 of the storage member 512 such that a fluid can pass over the outside and inside surfaces of the implantable medical device 650 when the fluid is passed through the first portion 538 of the storage member 512 and into the second portion 540 via the plurality of holes 536 and the through hole 542 of the separating wall 534.

Figure 16B:
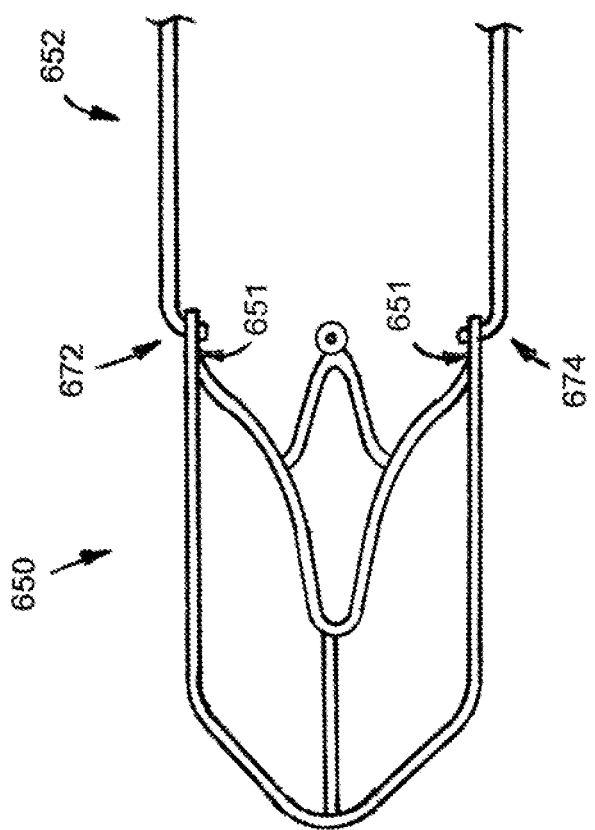
FIG. 16B is a partial top view of a loading puller attached to an implantable medical device.

In the illustrated embodiment, the loading puller 652 is releasably attached to the implantable medical device 650 and is partially disposed within each of the storage member 512 and the second cap 516. The loading puller 652 has a lengthwise axis 657, a first end 658, a second end 660, a length 661, and main body 662 that defines a first bend 664, a second bend 666, a third bend 668, and a fourth bend 670. The loading puller 657 is sized and configured to mate with a notch defined by an elongate member of a delivery system, as described in more detail herein. The first bend 664 is positioned near the first end 658 between the first end 658 and the second bend 666 and the fourth bend 670 is positioned near the second end 660 between the second end 660 and the third bend 668 such that the loading puller defines two hooked ends 672, 674 that partially surround a portion of the frame 654 of the implantable medical device 650 when the loading puller 652 is releasably attached to the implantable medical device 650. The first hooked end 672 is opposably positioned from the second hooked end 674 relative to a lengthwise axis 657 of the loading puller 652. The second bend 666 is disposed between the first bend 664 and the third bend 668 and the third bend 668 is disposed between the second bend 666 and the fourth bend 670 such that the loading puller 652 defines a u-shaped member 676. The loading puller 652 is moveable between a first, uncompressed, or open configuration and a second, compressed, or closed, configuration. In the closed configuration, the loading puller 652 has a width disposed between the hooked end 672, 674 that is less than the outside diameter of an implantable medical device such that the loading puller 652 can be releasably attached to the implantable medical device. In the closed configuration, a portion of the loading puller 652 (e.g., hooked ends 672, 674) is disposed within one or more openings 651 defined by a frame of an implantable medical device 650, such that the loading puller 652 is capable of applying axial force on the implantable medical device 650 when axial force is applied to the loading puller 652, as shown in FIG. 16B. In the open configuration, the loading puller 652 has a width disposed between the hooked ends 672, 674 that is greater than the outside diameter of the implantable medical device such that the loading puller is free of the implantable medical device. In the illustrated embodiment, the loading puller 652 is biased to the open configuration.

While the loading puller 652 has been illustrated as having a particular structural arrangement, a loading puller can have any suitable structural arrangement capable of providing releasable attachment to an implantable medical device and advancing the implantable medical device through a storage device and/or loading device, as described in more detail herein. Selection of a suitable structural arrangement for a loading puller can be based on various considerations, such as the structural arrangement of an implantable medical device to which the loading puller is intended to be attached. For example, while loading puller 652 has been illustrated as having a first hooked end 672 that is opposably positioned from a second hooked end 674 relative to the lengthwise axis 657 of the loading puller 652, a first hooked end can be positioned at any suitable location relative to a second hooked end relative to a lengthwise axis of the loading puller. While the loading puller 652 has been illustrated as defining four bends, a loading puller can define any suitable number of bends. Examples of numbers of bends considered suitable for a loading puller to define include one, at least one, two, a plurality, three, four, five, more than five, and any other number considered suitable for a particular embodiment. For example, a loading puller can define only first and second bends to define first and second hooked ends and can include a curve defined between the first bend and the second bend such that the first hooked end is opposably positioned from the second hooked end. Alternatively, a loading puller can define only first, second, and third bends to define first and second hooked ends and the third bend can be defined between the first bend and the second bend such that the first hooked end is opposably positioned from the second hooked end.

A loading puller 652 can be formed of any suitable material and using any suitable method of manufacture and selection of a suitable material and method of manufacture can be based on various considerations, including the material forming an implantable medical device to which the loading puller is intended to be releasably attached. Examples of materials considered suitable to form a loading puller include biocompatible materials, materials that can be made biocompatible, metals, shape memory alloys, Nitinol, plastics, and any other material considered suitable for a particular embodiment. In the illustrated embodiment, the loading puller is formed of Nitinol.

Figure 17:
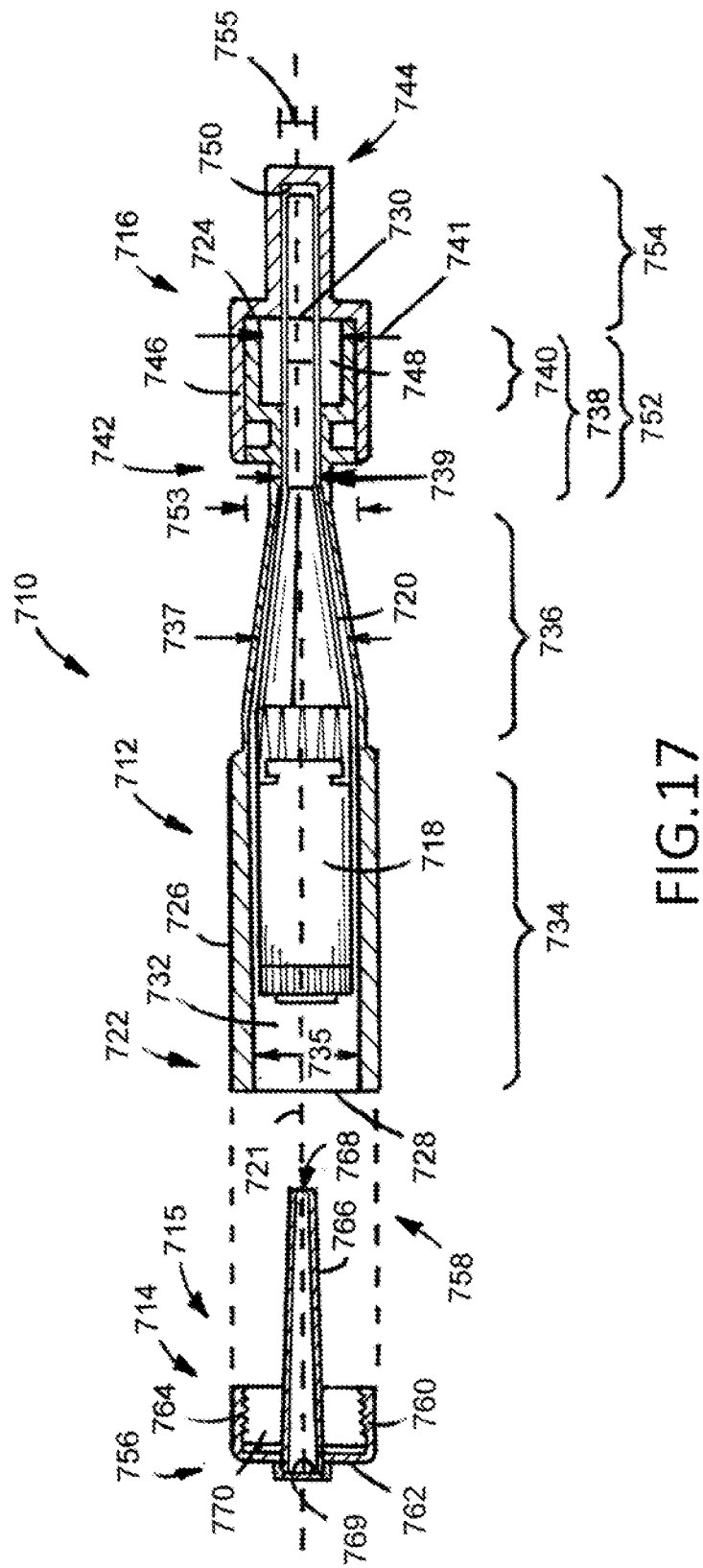
FIG. 17 is a partially exploded cross-sectional view of a first example loading device taken along the lengthwise axis of the loading member.
Figure 18:
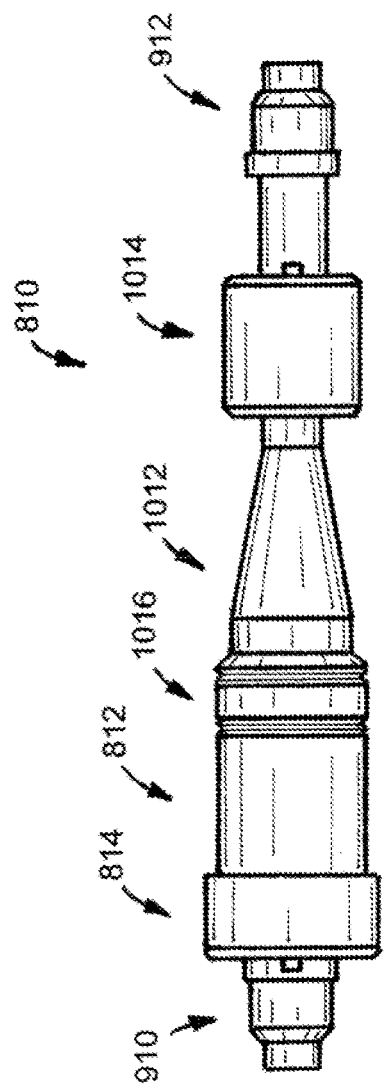
FIG. 18 is an elevation view of a second example loading device.

FIG. 17 illustrates an example loading device 710. The loading device 710 includes a loading member 712, a first cap 714, a second cap 716, an implantable medical device 718, and a loading puller 720. The implantable medical device 718 is similar to the implantable medical device 650 illustrated in FIGS. 15 and 16 and described above, except as detailed below. The loading puller 720 is similar to the loading puller 652 illustrated in FIGS. 15 and 16 and described above, except as detailed below.

In the illustrated embodiment, the loading member 712 has a lengthwise axis 721, a first end 722, a second end 724, and a main body 726 that defines a first opening 728, a second opening 730, and a passageway 732. The passageway 732 extends from the first opening 728 to the second opening 730 and has a first portion 734, a second portion 736, a third portion 738, and a fourth portion 740. The passageway 732 is sized and configured to house the implantable medical device 718. The first portion 734 extends from the first end 722 to the second portion 736 and has an inside diameter 735. The second portion 736 extends from the first portion 734 to the third portion 738 and has an inside diameter 737 that tapers from the first portion 734 to the third portion 738. The third portion 738 extends from the second portion 736 toward the second end. In the illustrated embodiment, the third portion 738 extends from the second portion 736 to the second end 724, has a first cross-sectional configuration taken along a plane orthogonal to the lengthwise axis 721 (e.g., circular cross-sectional configuration), and has an inside diameter 739 that is less than the inside diameter 735 of the first portion 734. The fourth portion 740 extends from the third portion 738 (e.g., a location between the second end 724 and the second portion 736) to the second end 724, has a second cross-sectional configuration taken along a plane orthogonal to the lengthwise axis 721 (e.g., elongated cross-sectional configuration, rectangular cross-sectional configuration), and has a width 741 (measured on a plane that is orthogonal to the lengthwise axis 721) that is greater than the inside diameter 739 of the third portion 738 and less than the inside diameter 735 of the first portion 734 of the passageway 732. In use, when the loading puller 720 is pulled through the passageway 732 the loading puller 720 is in its closed configuration and the implantable medical device 718 is in its compressed configuration as its moves through the second portion 736 of the passageway 732. When the loading puller 720 reaches the fourth portion 740 of the passageway 732 it expands to its open configuration while the implantable medical device 718 remains in its compressed configuration. While the implantable medical device 718 is illustrated as being disposed within the first portion 734 of the passageway 732, an implantable medical device can be disposed within any suitable portion of a loading member. Depending on the structural arrangement of an implantable medical device intended to be positioned within a loading device, a passageway can have any suitable structural arrangement, For example, the various portions of the passageway can have any suitable cross-sectional configuration, such as circular, elongated, oval, rectangular, a portion of a passageway can have a constant inside diameter along the length of the portion, an inside diameter that varies along the length of the portion (e.g., tapers from the first end toward the second end, or a location between the first end and the second end toward the second end, defines a shoulder within the portion such that a first inside diameter is between the first end and the shoulder and a second inside diameter is between the shoulder and the second end that is greater than the first inside diameter), or any other arrangement considered suitable for a particular embodiment.

The second cap 716 is releasably attached to the second end 724 of the loading member 712 and has a first end 742, a second end, 744, and a main body 746 that defines a recess 748 and a recess base 750. The recess 748 has a first portion 752 and a second portion 754. The first portion 752 has a first inside diameter 753 and the second portion 754 has a second inside diameter 755 that is less than the first inside diameter 753 of the first portion 752. The second portion 754 is sized and configured to receive a portion of the loading puller 720. The second cap 716 and the loading member 712 define mating structure that achieves a snap-fit attachment between the second cap 716 and the loading member 712.

In the illustrated embodiment, the first cap 714 comprises a device guard 715 that is releasably attached to the first end 722 of the loading member 712 and partially extends into the passageway 732 defined by the loading member 712. The device guard 715 has a first end 756, a second end 758, and a main body 760 that defines a base 762, a sidewall 764, a projection 766, and a recess 768 that extends into the projection 766. The base 762 and the sidewall 764 cooperatively define a cavity 770 that is sized and configured to receive a portion of the loading member 712. The projection 766 extends from the base 762, through the cavity 770, and to an environment exterior to the cavity 770. The recess 768 extends from the second end 758 toward the first end 756 to a recess base 769. The recess 768 is sized and configured to receive a portion of a delivery system, as described in more detail herein. While device guard 715 has been illustrated as being releasably attached to loading member 712, any suitable device guard, such as those described herein (e.g., device guard 146, device guard 1714), or cap, such as those described herein (e.g., cap 14), can be releasably attached to a loading member. Alternative embodiments can include a device guard that includes a projection that has a length that is greater than, or equal to, a tip of a delivery system or that defines an opening on a first end or a hollowed extension that is sized and configured to receive a portion of a tip of a delivery system.

In the illustrated embodiment, the loading puller 720 is releasably attached to the implantable medical device 718 and is partially disposed within each of the loading member 712 (e.g., passageway 732) and the second cap 716. In embodiments that include first and second tracks, as described in more detail herein, a loading puller is partially disposed within the passageway defined by the loading member, a first track, and a second track.

Optionally, a loading device can include a port (e.g., port 121), a first two-way valve (e.g., valve 123), a passageway defined on a first cap (e.g., passageway 426), a passageway defined on a second cap (e.g., passageway 125), and a second two-way valve (e.g., valve 127). In these embodiments, an implantable medical device can be positioned within the loading member (e.g., first portion of passageway) and the caps can be positioned on the loading member as described. Subsequently, if not already sterilized, a sterilizing material can be passed through the loading member using the port to sterilize the implantable medical device using the first and second two-way valves and any suitable components attached to the valves to pass the sterilizing material through the loading member. After sterilization, a rinsing material can be passed through the loading member using the port to rinse the implantable medical device using the first and second two-way valves and any suitable components attached to the valves to pass the rinsing material through the loading member. Optionally, a holding material can be passed through the loading member using the port to store the implantable medical device using the first and second two-way valves and any suitable components attached to the valves to pass the holding material through the loading member. This structural arrangement provides a mechanism for sterilizing, rinsing, and storing an implantable medical device such that the implantable medical device is not contacted by any component until a delivery system, as described herein, is used to deliver the implantable medical device.

The loading device 710 provides a mechanism for decreasing the complexity of sterilizing, storing, rinsing, and/or loading an implantable medical device and minimizing the risk associated with handling an implantable medical device that is intended for implantation. For example, the loading device 710 provides a mechanism for sterilizing, storing, rinsing, and/or loading an implantable medical device using a closed system that reduces the interaction with the implantable medical device during sterilization, storing, rinsing, and/or loading.

FIGS. 18, 19, 20, 21, 22, 23, 24, 25, and 26 illustrate another example loading device 810. The loading device 810 includes a storage member 812, a first cap 814, a first one-way valve 910, a second one-way valve 912, a diffuser 914, a loading member 1012, a second cap 1014, a connector 1016, and a loading puller 1020. Each of the storage member 812, the first cap 814, the first one-way valve 910, the second one-way valve 912, and the diffuser 914 is similar respectively to the storage member 312, the first cap 314, the first one-way valve 410, the second one-way valve 412, and the diffuser 414 illustrated in FIGS. 8, 9, 10, 11, 12, 13, and 14 and described above, except as detailed below. Each of the loading member 1012 and the second cap 1014 is similar respectively to the loading member 712 and cap 714 illustrated in FIG. 17 and described above, except as detailed below.

Figure 19:
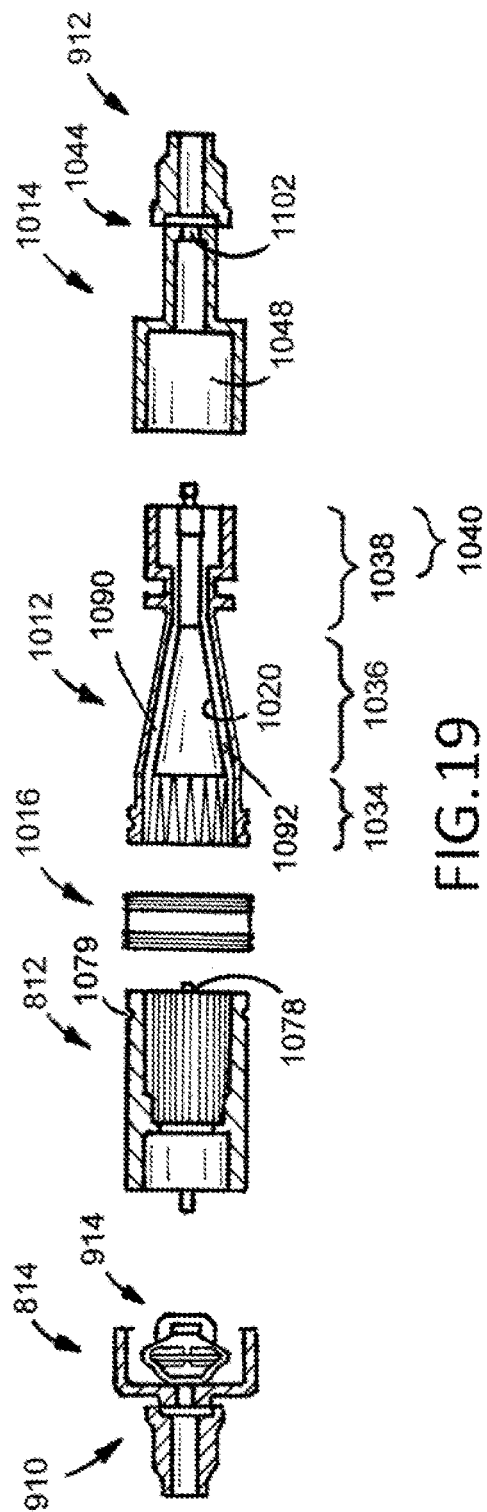
FIG. 19 is an exploded cross-sectional view of the loading device illustrated in FIG. 18 taken along the lengthwise axis of the storage member.
Figure 20:
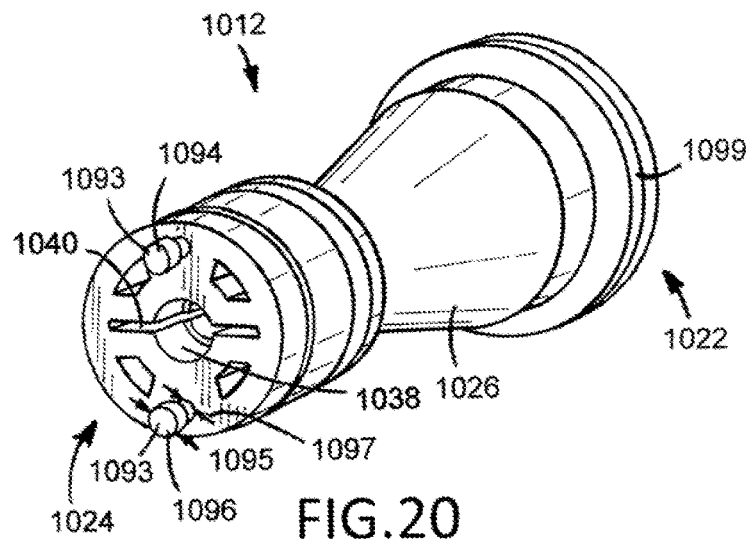
FIG. 20 is a perspective view of the loading member illustrated in FIG. 18.
Figure 22:
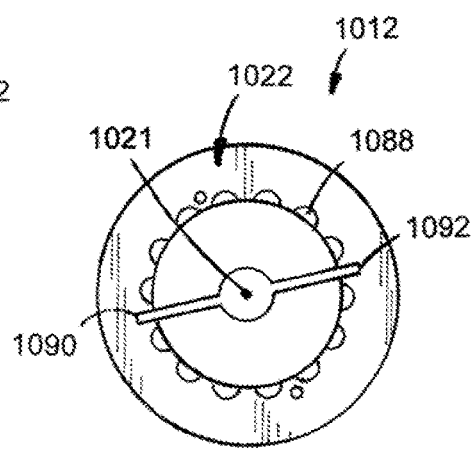
FIG. 22 is an end view of the loading member illustrated in FIG. 18.
Figure 21:
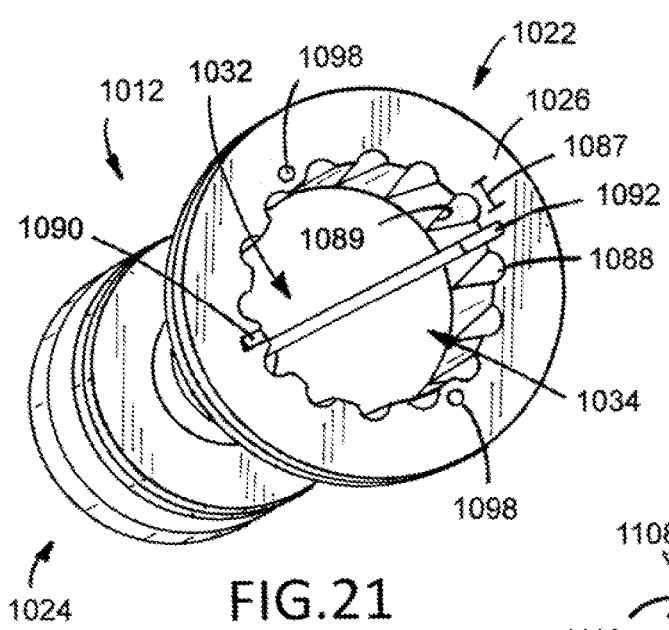
FIG. 21 is another perspective view of the loading member illustrated in FIG. 18.
Figure 24:
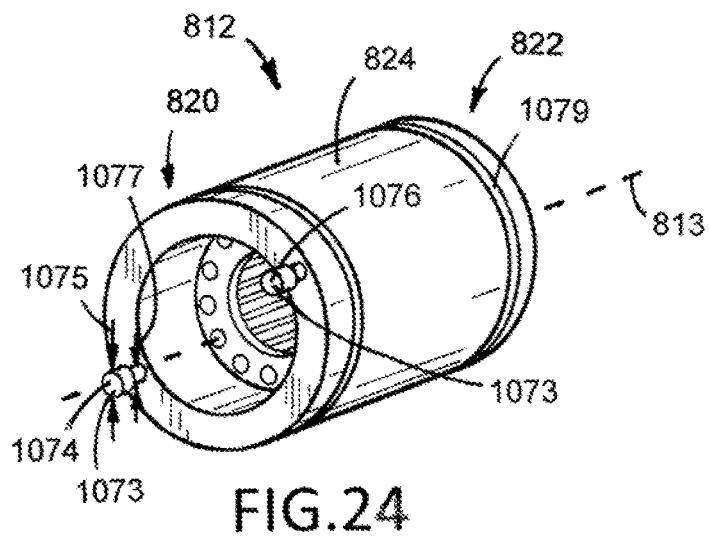
FIG. 24 is a perspective view of the storage member illustrated in FIG. 18.

As shown in FIGS. 19 and 24, the main body 824 of the storage member 812 defines first and second posts 1074, 1076, protuberances 1078, and a recess 1079. Each of the first and second posts 1074, 1076 extends from the first end 820 and away from the second end 822 to an end 1073. Each of the posts 1074, 1076 has a first outside diameter 1075 at the end 1073 of the post and a second outside diameter 1077 between the end of the post and the first end 820 of the first cap 812. The second outside diameter is less than the first outside diameter. Each protuberance 1078 extends from the second end 822 and away from the first end 820 and is sized and configured to be received by a recess 1098 defined by the loading member 1012, as shown in FIG. 21. The recess 1079 extends into the main body 824 from an exterior surface and toward the lengthwise axis 813 of the storage member 812. The recess 1079 is sized and configured to receive a portion of the connector 1016, as described in more detail herein.

Figure 25:
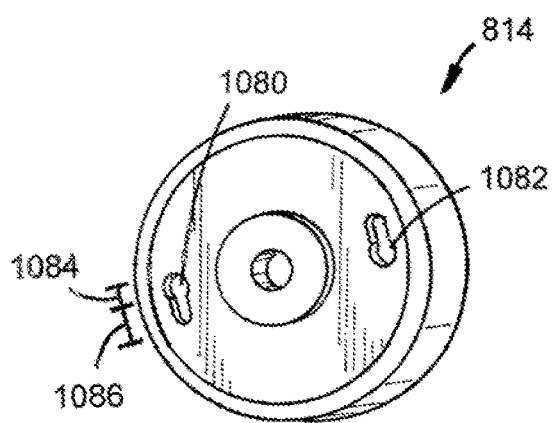
FIG. 25 is a perspective view of the first cap illustrated in FIG. 18.
Figure 26:
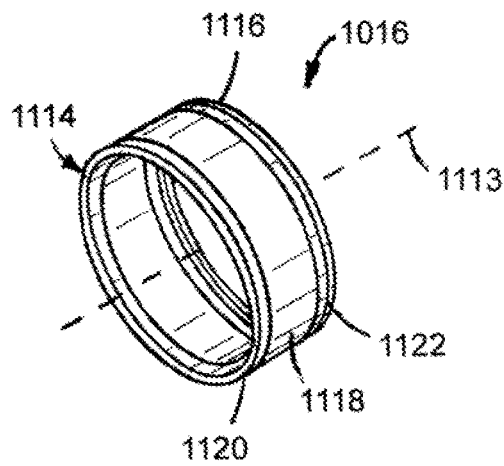
FIG. 26 is a perspective view of the connector illustrated in FIG. 18.

As shown in FIGS. 19 and 25, the diffuser 914 is permanently attached to the first cap 814, the first one-way valve 910 is permanently attached to the first cap 814, and the first cap 814 defines first and second openings 1080, 1082 that are each sized and configured to receive a portion of a post 1074, 1076 defined by the storage member 812. Each opening 1080, 1082 has a first portion 1084 sized and configured to receive the portion of a post 1074, 1076 that has the first outside diameter 1075 and a second portion 1086 that is sized and configured to receive the portion of a post 1074, 1076 that has the second outside diameter 1077. In use, the first cap 814 is positioned on the storage member 812 such that the first post 1074 is disposed within the first opening 1080 and the second post 1076 is disposed within the second opening 1082. After the posts 1074, 1076 have been positioned within the openings 1080, 1082, the first cap 814 is rotated relative to the storage member 812 about the lengthwise axis 813 of the storage member 812 to achieve releasable attachment between the storage member 812 and the first cap 814.

In the illustrated embodiment, the loading member 1012 is releasably attached to the storage member 812 using the connector 1016 and the main body 1026 of the loading member 1012 defines a plurality of recesses 1088, a first track 1090, a second track 1092, first and second posts 1094, 1096, a plurality of recesses 1098, and recess 1099. Each recess of the of the plurality of recesses 1088 extends from the first end 1022 of the loading member 1012 toward the second end 1024 and terminates at the junction between the first portion 1034 and the second portion 1036 of the passageway 1032. Each recess of the plurality of recesses 1088 has a first width 1087 at the first end 1022 of the loading member 1012 and a second width 1089 between the first end 1022 and the second end 1024. The first width 1087 is greater than the second width 1089 such that each recess of the plurality of recesses tapers from the first end 1022 toward the second end 1024. Each of the first track 1090 and the second track 1092 extends from the first end 1022 of the loading member 1012, into the main body 1026, through each of the first portion 1034, second portion 1036, and a portion of the third portion 1038 of the passageway 1032, to the fourth portion 1040 of the passageway 1032 and is sized and configured to receive a portion of the loading puller 1020. Each of the first and second tracks 1090, 1092 provides a mechanism to guide the loading puller 1020 through the loading member 1012 during use. Each of the first and second posts 1094, 1096 extends from the second end 1024 of the loading member 1012 and away from the first end 1022 to an end 1093. Each of the posts 1094, 1096 has a first outside diameter 1095 at the end 1093 of the post and a second outside diameter 1097 between the end 1093 of the post and the second end 1024 of the loading member 1012. The second outside diameter 1097 is less than the first outside diameter 1095. Each recess 1098 extends from the first end 1022, into the main body 1026 of the loading member 1012, and is sized and configured to receive a protuberance 1078 defined by the storage member 812. When the protuberances 1078 are received within the recesses 1098, the plurality of recesses 916 defined by the storage member 812 is aligned with the plurality of recesses 1088 defined by the loading member 1012. The recess 1099 extends into the main body 1026 from an exterior surface and toward the lengthwise axis 1021 of the loading member 1012. The recess 1099 is sized and configured to receive a portion of the connector 1016, as described in more detail herein.

While each recess of the plurality of recesses 1088 has been illustrated as extending from the first end 1022 of the loading member 1012 toward the second end 1024 and terminating at the junction between the first portion 1034 and the second portion 1036 of the passageway 1032 and as having a first width 1087 at the first end 1022 of the loading member 1012 and a second width 1089 between the first end 1022 and the second end 1024 that is less than the first width 1087, each recess can have any suitable structural arrangement. Selection of a suitable structural arrangement for each recess included in a loading member can be based on various considerations, including the structural arrangement of an implantable medical device intended to be passed through a loading member. For example, a loading member can define any suitable number of recesses, such as one, at least one, two, a plurality, three, four, five, more than five, more than ten, and any other number considered suitable for a particular embodiment. A recess included on a loading member can extend any suitable length of a loading member. For example, a recess, or each recess of a plurality of recesses, can extend from a first end to a second end of a loading member, from a first end to a location between the first end and the second end of a loading member, from a location between a first end and a second end to the second end of the loading member, from a first location between a first end and a second end to a second location between the first location and the second end of a loading member, and any other length of a loading member considered suitable for a particular embodiment. A recess included on a loading member can have any suitable width along its length. For example, a recess, or each recess of a plurality of recesses, can have a first width at a first end (e.g., at a first end of a loading member) and a second width at a second end (e.g., between a first end and a second end of a loading member) that is greater than, less than, equal to, or about the first width. A recess included on a loading member can have any suitable structural arrangement, such as curved, cuboidal, prismatic, and any other structural arrangement considered suitable for a particular embodiment.

Figure 23:
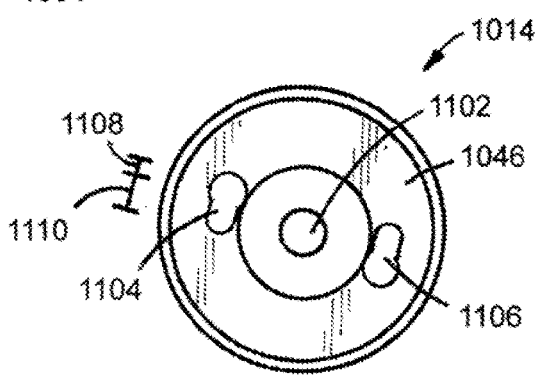
FIG. 23 is an end view of the second cap illustrated in FIG. 18.

In the illustrated embodiment, the second cap 1014 is releasably attached to the second end 1024 of the loading member 1012 and the second one-way valve 912 is permanently attached to the second end 1044 of the second cap 1014. Alternative embodiment, however, can include a cap that incorporates a one-way or two-way valve within the cap such that a separate component attached to the cap is not needed. The main body 1046 of the second cap 1014 defines a passageway 1102 that extends through the second end 1044 and provides access to the recess 1048. As shown in FIG. 23, the second cap 1014 defines first and second openings 1104, 1106 that are each sized and configured to receive a portion of a post 1094, 1096 defined by the loading member 1012. Each opening 1104, 1106 has a first portion 1108 sized and configured to receive the portion of a post 1094, 1096 that has the first outside diameter 1095 and a second portion 1110 that is sized and configured to receive the portion of a post 1094, 1096 that has the second outside diameter 1097. In use, the second cap 1014 is positioned on the loading member 1012 such that the first post 1094 is disposed within the first opening 1104 and the second post 1096 is disposed within the second opening 1106. After the posts 1094, 1096 have been positioned within the openings 1104, 1106, the second cap 1014 is rotated relative to the loading member 1012 about the lengthwise axis 1021 of the loading member 1012 to achieve releasable attachment between the loading member 1012 and the second cap 1014.

The connector 1016 is releasably attached to the storage member 812 and the loading member 1012. The connector 1016 has a lengthwise axis 1113, a first end 1114, a second end 1116, and a main body 1118 that defines a first projection 1120 and a second projection 1122. Each of the first projection 1120 and the second projection 1122 extends from the main body 1118 and toward the lengthwise axis 1113 of the connector 1016. The first projection 1120 is sized and configured to be received by the recess 1079 defined by the storage member 812 and the second projection 1122 is sized and configured to be received by the recess 1099 defined by the loading member 1012. The connector 1016 provides releasable attachment between the storage member 812 and the loading member 1012. In an alternative embodiment, a connector can be omitted and a storage member can be directly attached to a loading member using any suitable method or technique that achieves releasable attachment, such as those described herein. Alternatively, a connector can be permanently attached to a storage member and a loading member (e.g., using a crimp connection).

Any of the storage devices and/or loading devices described herein can optionally include an implantable medical device housed within a second portion of a storage member. Any suitable implantable medical device can be included in a storage member and selection of a suitable implantable medical device can be based on various considerations, including the treatment intended to be performed. Examples of implantable medical devices considered suitable to include in a storage member include implantable medical devices that include a frame, such as a support frame, implantable medical devices that include a frame and a material attached to the frame, venous valves, heart valves, stents, occluders that include a frame along with leaflets that are sewn or otherwise attached to each other to permanently close an associated valve orifice or a graft material that lacks an orifice, and any other implantable medical device considered suitable for a particular embodiment.

Examples of frames considered suitable to include on an implantable medical device include those that comprise an expandable frame having radially compressed and radially expanded configurations. Such a frame can be implanted at a point of treatment within a body vessel by minimally invasive techniques, such as delivery and deployment with a delivery system, such as those described herein, that is sized and configured for navigation within the body vessel. It is noted, though, that implantable medical devices, such as frames, regardless of the type and/or nature of the frame, can be implanted within a body vessel at a desired point of treatment using conventional minimally-invasive techniques, such as by delivery with an associated delivery system, such as those described herein, by surgical techniques, or by any other suitable technique for placing a frame or medical device at a point of treatment within a body vessel.

A frame can be self-expandable or can require an input of force to affect expansion, such as a balloon expandable frame. A frame can provide a stenting function, i.e., exert a radially outward force on the interior wall of a vessel in which the frame, or implantable medical device including the frame, is implanted. By including a frame that exerts such a force, an implantable medical device can provide multiple functions, such as a stenting and a valving function, at a point of treatment within a body vessel, which may be desirable in certain situations, such as when a degree of vessel stenosis, occlusion, and/or weakening is present.

A frame of an implantable medical device can include any suitable structural elements, such as struts and bends, conventional structural features that facilitate anchoring of the frame at a point of treatment within a body vessel, such as barbs and/or microbarbs, and structural features, such as radiopaque markers, that facilitate visualization of the frame in conventional or other medical visualization techniques, such as radiography, fluoroscopy, and other techniques. Furthermore, a frame can include structural features, such as eyelets, barbs, fillets and other suitable structures, that provide attachment points for grafts and other materials.

A frame can be made from any suitable material and selection of an appropriate material for use in a frame according to a particular embodiment can be based on various considerations, including any desired flexibility and visualization characteristics. The material selected for a frame need only be biocompatible or be able to be made biocompatible. Examples of suitable materials include, without limitation, stainless steel, nickel titanium (NiTi) alloys, e.g., Nitinol, other shape memory and/or superelastic materials, molybdenum alloys, tantalum alloys, titanium alloys, precious metal alloys, nickel chromium alloys, cobalt chromium alloys, nickel cobalt chromium alloys, nickel cobalt chromium molybdenum alloys, nickel titanium chromium alloys, linear elastic Nitinol wires, polymeric materials, and composite materials. Absorbable and bioremodellable materials can also be used to form a frame. As used herein, the term "absorbable" refers to the ability of a material to degrade and to be absorbed into a tissue and/or body fluid upon contact with the tissue and/or body fluid. A number of absorbable materials are known in the art, and any suitable absorbable material can be used. Examples of suitable types of absorbable materials include absorbable homopolymers, copolymers, or blends of absorbable polymers. Specific examples of suitable absorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived absorbable polymers that may be suitable, including modified polysaccharides, such as cellulose, chitin, and dextran, and modified proteins, such as fibrin and casein.

Stainless steel and nitinol are currently considered suitable materials for use in a frame of an implantable medical device due at least to their biocompatibility, shapeability, and well-characterized nature. Also, cold drawn cobalt chromium alloys, such as ASTM F562 and ASTM F1058 (commercial examples of which include MP35N™ and Elgiloy™, both of which are available from Fort Wayne Metals, Fort Wayne, IN; MP35N is a registered trademark of SPS Technologies, Inc. (Jenkintown, PA, USA); Elgiloy is a registered trademark of Combined Metals of Chicago LLC (Elk Grove Village, IL, USA)), are currently considered suitable materials for frames at least because they are non-magnetic materials that provide beneficial magnetic resonance imaging (MRI) compatibility and avoid MRI artifacts typically associated with some other materials, such as stainless steel.

A frame can be fabricated in any suitable manner and by any suitable technique and selection of an appropriate manner and/or technique for fabricating a frame can be based on various considerations, including the nature of the material from which the frame is being fabricated. Examples of suitable techniques include forming a frame from wire, such as by wrapping a suitable wire around a suitable mandrel, by cutting the frame from a tubular section of an appropriate material, such as by laser-cutting the support frame from a metal tubular member, and by forming the desired structure of the frame in sheet form, such as by vapor deposition or other suitable technique, configuring the sheet into tubular form, such as by rolling or other suitable technique, and fixing the frame in tubular form, such as by laser-welding or other suitable technique.

If an implantable medical device includes a frame and a material attached to the frame, the material attached to the frame can form any suitable structure and selection of a suitable structure for a material attached to a frame to form can be based on various considerations, including the treatment intended to be performed. Any suitable material can be attached to the frame to form an implantable medical device and selection of an appropriate material for use with a frame in an implantable medical device can be based on various considerations, including the intended use and desired function of the implantable medical device. For valve devices, such as venous valves, heart valves, or any other valve device, one or more leaflets, each having a free edge, can be attached to a frame and comprise a section of material, such as a sheet, that is attached to the frame along a respective attachment pathway. The leaflets can be formed of any suitable material, and need only be biocompatible or be able to be made biocompatible. The material can be formed of a flexible material. Examples of suitable materials for use as leaflets in implantable medical devices include natural materials, synthetic materials, and combinations of natural and synthetic materials. Examples of suitable natural materials include extracellular matrix (ECM) materials, such as small intestine submucosa (SIS), and other bioremodelable materials, such as bovine pericardium. Other examples of suitable ECM materials that can be used include stomach submucosa, liver basement membrane, urinary bladder submucosa, tissue mucosa, and dura mater. Other examples of suitable natural materials include renal capsule matrix, abdominal fascia, parenchyma, such as abdominal parenchyma, connective tissue, pulmonary or lung ligament, tissue laminates, and natural valve leaflets with or without adjacent vessel wall. Pleura is also considered a suitable natural material, including visceral pleura. Fixed tissues are also considered suitable, including fixed SIS, fixed pericardium, fixed pulmonary or lung ligament, and any other suitable fixed natural tissue. When fixed tissue is used, any suitable fixation technique and/or procedure can be used, including chemical fixatives, such as aldehydes, e.g., formaldehyde, glutaraldehyde, and formalin, and carbodiimides, such as ethyl dimethylaminopropyl carbodiimide, dicyclohexylcarbodiimide. Physical fixation techniques and/or procedures can also be used, including exposure to heat and/or radiation. Lyophilized preparations and chemically-dried preparations of these natural materials are also considered suitable. Examples of suitable synthetic materials include polymeric materials, such as expanded polytetrafluoroethylene, polyurethane, polyurethane urea, polycarbonate, and polyesters.

Any materials attached to a frame can have any suitable size, shape and configuration. For example, valve devices can include one, two or more leaflets that are sheet-like sections of material attached to a frame. Another example of a material that can be attached to a frame is a tubular structure that is attached around the outer circumference of the frame. Indeed, a tubular structure and one, two or more leaflets can be attached to a frame to form a valve device having an outer sleeve.

Any material and/or elements attached to a frame can be attached to the frame in any suitable manner and with any suitable structure and/or substance. For example, leaflets can be attached to a frame in a valve device using sutures, tissue welding, adhesive(s), mechanical attachment(s), a combination of these approaches, and any other suitable structure and/or substance.

The loading device 810 provides a mechanism for decreasing the complexity of sterilizing, storing, rinsing, and/or loading an implantable medical device and minimizing the risk associated with handling an implantable medical device that is intended for implantation. For example, the loading device 810 provides a mechanism for sterilizing, storing, rinsing, and/or loading an implantable medical device using a closed system that reduces the interaction with the implantable medical device during sterilization, storing, rinsing, and/or loading.

FIGS. 27 and 28 illustrate an example delivery system 1210. The delivery system 1210 includes a sheath 1212, an elongate member 1214, and a tip 1216.

The sheath 1212 has a first end 1220, a second end 1222, a length 1223, and a main body 1224 that defines a lumen 1226 that extends through the entire length 1223 and is sized and configured to receive a portion of the elongate member 1214, a portion of the tip 1216, and a portion of an implantable medical device. The second end of a sheath can optionally include a radiopaque material. The elongate member 1214 has a lengthwise axis 1229, a first end 1230, a second end 1232, and a main body 1234 that defines an outer surface 1236, an inner surface 1238, a lumen 1240, and a notch 1242. In the illustrated embodiment, the elongate member 1214 is formed of 304 stainless steel. The lumen 1240 extends through the entire length of the elongate member 1214 and is sized (e.g., 0.035") and configured to receive a portion of a wire guide, or another medical device. The notch 1242 extends into the main body 1234 of the elongate member 1214 from the outer surface 1236 to the inner surface 1238, toward the lengthwise axis 1229, and toward the second end 1232 of the elongate member 1214 at an angle 1243. In the illustrated embodiment, the angle 1243 is greater than zero degrees relative to the lengthwise axis 1229 of the elongate member 1214. A notch can be defined at any suitable angle such as angles equal to, less than, greater than, or about 15 degrees, 30 degrees, 45 degrees, 60 degrees, or 75 degrees relative to the lengthwise axis of an elongate member. The notch 1242 is sized and configured to receive and mate with a portion of a loading puller, as described in more detail herein. In the illustrated embodiment, the angle 1243 is equal to about 45 degrees relative to the lengthwise axis 1229 of the elongate member 1214. While the elongate member 1214 has been illustrated as defining an inner surface 1238 and a lumen 1240, an alternative embodiment can include an elongate member that comprises a solid piece of material that does not include an inner surface that defines a lumen. In this alternative embodiment, a notch can be defined in the main body the elongate member as described above with respect to elongate member 1214.

The tip 1216 is disposed on the second end 1232 of the elongate member 1214 and has a first end 1246, a second end 1248, and a main body 1250 that defines a lumen 1251, a first portion 1252, a second portion 1254, and a third portion 1256. The tip 1216 is sized and configured to be partially disposed within the sheath 1212 and to receive an implantable medical device thereon such that the implantable medical device can be delivered to a point of treatment. In the illustrated embodiment, the first portion 1252 is sized and configured to be disposed within the sheath 1212. In an alternative embodiment, an elongate member can be disposed through the lumen defined by a tip such that the tip is disposed on a portion of the length of the elongate member. The notch 1242 is positioned from the first end 1246 of the tip 1216 a distance 1257 that is greater than the length of a loading puller such that the loading puller can be disposed within the notch and releasably attached to an implantable medical device that is disposed between the notch 1242 and the tip 1216 or disposed on the tip 1216. While the tip 1216 has been illustrated as defining a lumen 1251, an alternative embodiment can include a tip that comprises a solid piece of material that omits a lumen.

FIG. 29 illustrates another example delivery system 1310. The delivery system 1310 is similar to the delivery system 1210 illustrated in FIGS. 27 and 28 and described above, except as detailed below. The delivery system 1310 includes a sheath 1312, an elongate member 1314, a tip 1316, and a gripping member 1360.

In the illustrated embodiment, the elongate member 1314 has a lengthwise axis 1329, a first end 1330, a second end 1332, and a main body 1334 that defines an outer surface 1336. The gripping member 1360 is attached to the elongate member 1314 between the first end 1330 of the elongate member 1314 and the first end 1346 of the tip 1316. The gripping member 1360 has a first end 1362, a second end 1364, a length 1365, and a main body 1366. In use, the gripping member 1360 is sized and configured to be disposed within the lumen 1326 defined by the sheath 1312 and within a lumen defined by an implantable medical device disposed within a storage member. The gripping member 1360 provides a friction force between the frame of an implantable medical device and the sheath 1312 and assists with a controlled release of the implantable medical device during delivery such that jumping of the implantable medical device is prevented when being released from the sheath 1312. In embodiments in which a balloon is included on a delivery system, the balloon can be positioned between a tip and a gripping member, or be considered the tip and positioned distal to a gripping member. In these embodiments, the elongate member can define an inflation lumen that is in fluid communication with a balloon chamber and extends to an inflation port defined distal to a sheath.

A gripping member can be formed of any suitable material and have any suitable structural arrangement and selection of a suitable material and structural arrangement for a gripping member can be based on various considerations, including the intended use of a delivery system of which the gripping member is included. Examples of materials considered suitable for a gripping member include any material that has a coefficient of friction greater than the coefficient of friction of a material that forms an elongate member to which the gripping member is attached, polymers, silicone, polyurethane, rubbers, and any other material considered suitable for a particular embodiment.

FIG. 30 illustrates another example delivery system 1410. The delivery system 1410 is similar to the delivery system 1210 illustrated in FIGS. 27 and 28 and described above, except as detailed below. The delivery system 1410 includes a sheath 1412, an elongate member 1414, a tip 1416, and a gripping member 1460.

In the illustrated embodiment, the delivery system includes a gripping member 1460 that is attached to the elongate member 1414 between the notch 1442 and the first end 1446 of the tip 1416. The gripping member 1460 has a first end 1462, a second end 1464, a length 1465, and a main body 1466. In use, the gripping member 1460 is sized and configured to be disposed within the lumen 1426 defined by the sheath 1412 and within a lumen defined by an implantable medical device disposed within a storage member. In the illustrated embodiment, the gripping member 1460 is positioned from the notch 1442 a distance that is greater than the length of a loading puller intended to be used with the delivery system 1410 (e.g., length 661, length 2761). Optionally, a delivery system can include an inner pusher catheter disposed within a sheath and over an elongate member that can be used to assist with delivery of an implantable medical device. In addition, a delivery system can include one or more kerfs disposed between a notch and a proximal end of an elongate member.

Figure 31:
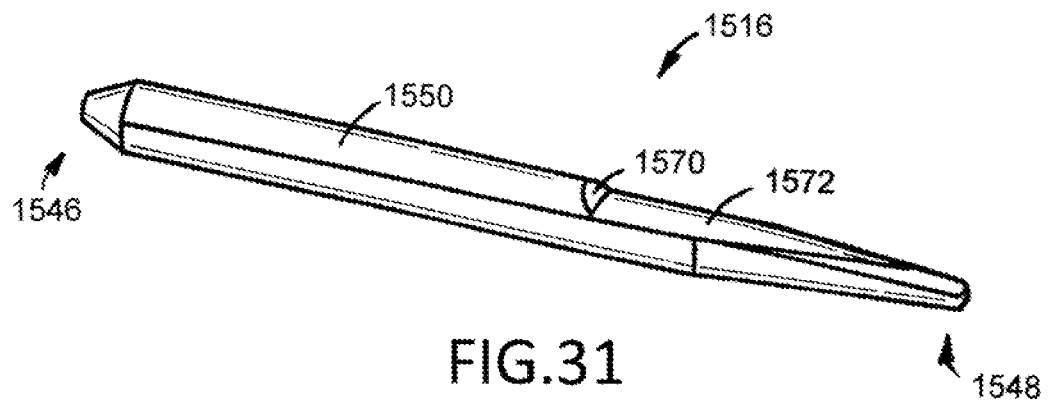
FIG. 31 is a perspective view of an alternative tip that can be included on an elongate member of a delivery system.
Figure 32:
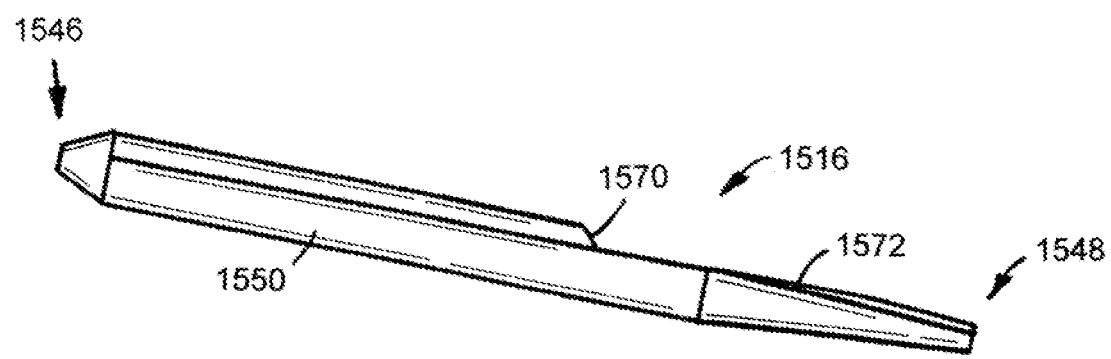
FIG. 32 is an elevation view of the tip illustrated in FIG. 31.
Figure 33:
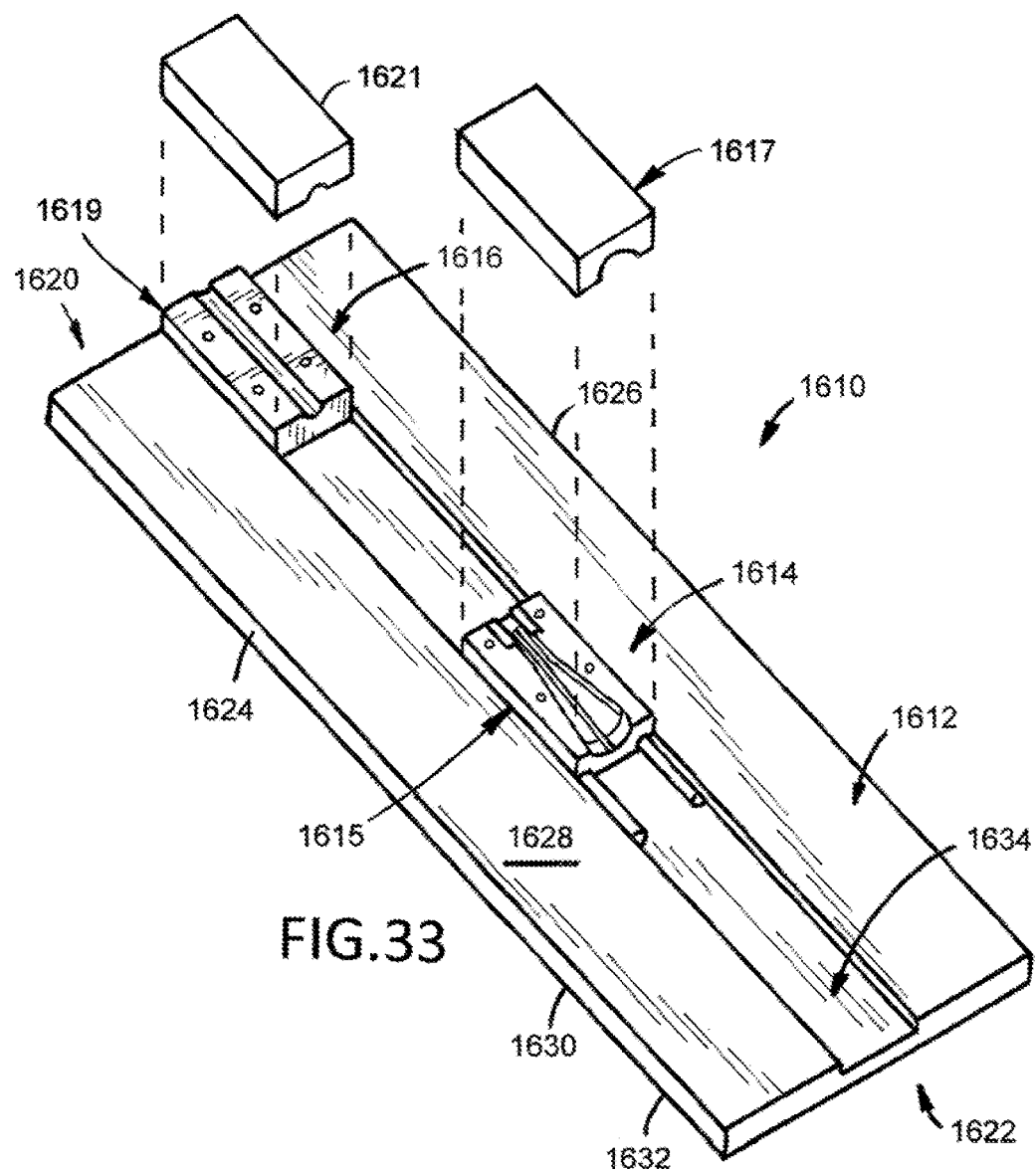
FIG. 33 is a perspective view of an example guide system.
Figure 34:
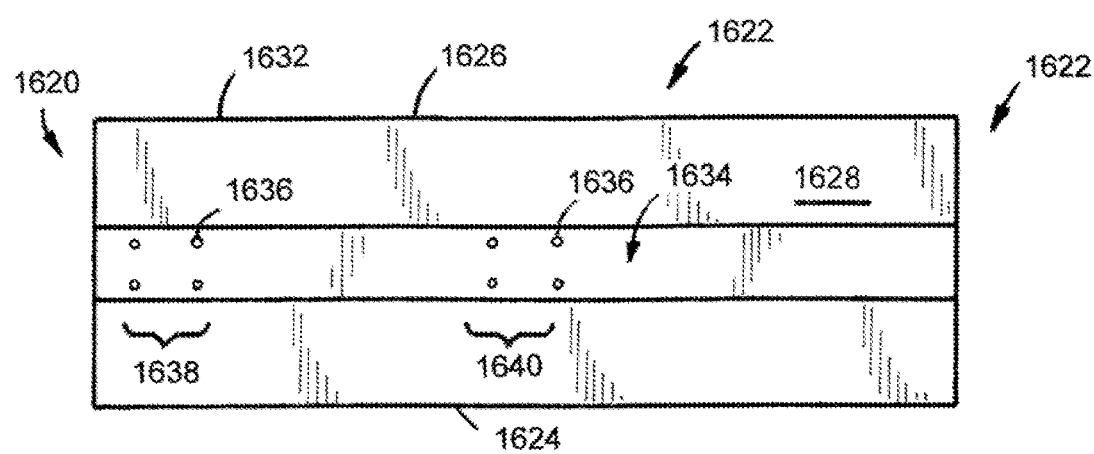
FIG. 34 is a top view of the guide board illustrated in FIG. 33.
Figure 36:
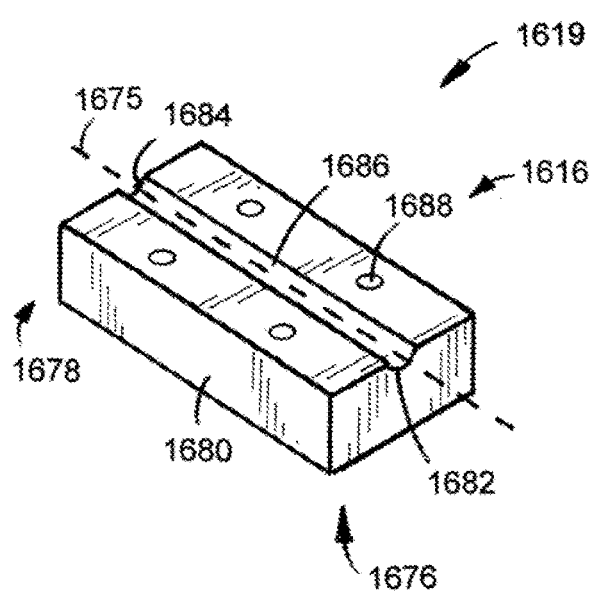
FIG. 36 is a perspective view of a portion of the guide member illustrated in FIG. 33.

FIGS. 31 and 32 illustrate an alternative tip 1516 that can be disposed the second end of an elongate member of an example delivery system. The tip 1516 is similar to the tip 1216 illustrated in FIG. 27 and described above, except as detailed below.

In the illustrated embodiment, the main body 1550 of the tip 1516 defines shoulder 1570 and a planar surface 1572. The shoulder 1570 is disposed between the first end 1546 of the tip 1516 and the second end 1548 of the tip 1516. The planar surface 1572 extends from the shoulder 1570 toward the second end 1548 to a location between the shoulder 1570 and the second end 1548. The inclusion of a shoulder 1570 and a planar surface 1572 provides a mechanism for orienting the tip 1516 and an attached elongate member relative to another component (e.g., loading member, storage member, device guard, planar surface of device guard), such as those described herein.

FIGS. 32A and 32B illustrate an alternative tip 1516' that can be disposed the second end of an elongate member of an example delivery system. The tip 1516' is similar to the tip 1216 illustrated in FIG. 27 and described above, except as detailed below.

In the illustrated embodiment, the main body 1550' of the tip 1516' defines a first recess 1570' and a second recess 1572'. Each of the first recess 1570' and the second recess 1572' extends from the first end 1546' toward the second end 1548' and is sized and configured to receive a portion of a device guard or cap such that the tip 1516' and an attached elongate member can be oriented relative to another component (e.g., loading member, storage member, device guard, planar surface of device guard), such as those described herein. In the illustrated embodiment, each of the first recess 1570' and the second recess 1572' is disposed on a plane that extends through the lengthwise axis of the tip 1516'. However, alternative embodiments can include a first recess that is disposed on a first plane that extends through a lengthwise axis of a tip and a second recess that is disposed on a second plane that extends through the lengthwise axis of the tip at any suitable angle relative to the first plane (e.g., 45 degrees).

While a first recess 1570' and a second recess 1572' have been illustrated, a main body of a tip can define any suitable number of recesses to assist with orienting the tip relative to a portion of a storage device and/or loading device and selection of a suitable number of recesses for a main body of a tip to define can be based on various considerations, such as the type of material forming a tip. Examples of suitable numbers of recesses for a main body of a tip to define include one, two, a plurality, three, four, five, more than five, and any other number considered suitable for a particular embodiment.

FIGS. 32C and 32D illustrate an alternative first cap 114' that can be releasably attached to a storage member of an example storage device or loading member of an example loading device. The first cap 114' is similar to the first cap 114 illustrated in FIGS. 4 and 5 and described above, except as detailed below.

In the illustrated embodiment, the first cap 114' comprises a device guard 146' that can be releasably attached to a first end of a storage member or a loading member. The device guard 146' has a lengthwise axis 147', a first end 148', a second end 150', and a main body 152' that defines a base 154', a first projection 156', a recess 160', a first projection 161', and a second projection 163'. The base 154' extends from the first end 148' toward the second end 150' and is sized and configured to be releasably attached within a passageway of a storage member. In the illustrated embodiment, the base 154' has an outside diameter 155', a first side 162', a second side 164', and is sized and configured to be releasably attached to a storage member within a passageway using a snap fit attachment between the device guard 146' and the storage member.

The first projection 156' extends from the second side 164' to the second end 150'. The first projection 156' has an outside diameter 157' that tapers from between the base 154' and the second end 150'. The recess 160' extends from the first end 148' toward the second end 150' to a recess base 166' and is sized and configured to receive a portion of a delivery system (e.g., tip 1516'), as described in more detail herein. The recess 160' has a first portion 168' and a second portion 170'. The first portion 168' has an inside diameter 167' that is constant from the first end 148' to the second portion 170'. The second portion 170' has an inside diameter 169' that tapers from the first portion 168' to the recess base 166'. The first portion 168' has a cylindrical configuration and the second portion 170' has a conical configuration. Each of the first projection 161' and the second projection 163' extends into the recess 160' and is sized and configured to mate with and be disposed within a recess defined by a tip (e.g., recess 1570', recess 1572') such that the delivery system is rotationally fixed relative to the device guard 146' when the projections 161', 163' are disposed within the recesses defined by the tip of the delivery system.

While a first projection 161' and a second projection 163' have been illustrated, a main body of a device guard can define any suitable number of projections to assist with orienting a tip relative to a portion of a storage device and/or loading device and selection of a suitable number of projections for a main body of a device guard to define can be based on various considerations, such as the type of material forming a tip. Examples of suitable numbers of projections for a main body of a device guard to define include one, two, a plurality, three, four, five, more than five, and any other number considered suitable for a particular embodiment.

FIGS. 33, 34, 35, and 36 illustrate an example guide system 1610. The guide system 1610 includes a guide board 1612, a loading member 1614, and a guide member 1616. The loading member 1614 is similar to the loading member 712 illustrated in FIG. 17 and described above, except as detailed below. The guide system 1610 can be used with any suitable storage device described herein, such as storage device 10, storage device 110, storage device 210, storage device 310, and/or storage device 510.

The guide board 1612 has a first end 1620, a second end 1622, a first side 1624, a second side 1626, a top surface 1628, a bottom surface 1630, and a main body 1632 that defines a notch 1634 and a plurality of apertures 1636. The notch 1634 extends from the first end 1620 to the second end 1622 and is sized and configured to receive the loading member 1614, the guide member 1616, and a storage member or a storage member that includes an attached device guard, as described herein. A first set of apertures 1638 of the plurality of apertures 1636 is disposed near the first end 1620 and a second set of apertures 1640 of the plurality of apertures 1636 is disposed between the first set of apertures 1638 and the second end 1622.

In the illustrated embodiment, the loading member 1614 is disposed within the notch 1634 and is releasably attachable to the guide board 1612 using mounting pins (not shown). The loading member 1614 has a first portion 1615 releasably attached to a second portion 1617 using the mounting pins. Alternatively, a first portion and a second portion of a loading member can be positioned relative to one another and not be releasably attached to one another. The loading member 1614 has a lengthwise axis 1644, a first end 1646, a second end 1648, and a main body 1650 that defines a first opening 1652, a second opening 1654, a passageway 1656, a first track 1658, a second track 1660, a third track 1662, a fourth track 1677, a plurality of mounting passageways 1663, and guide pins 1665. Each of the first opening 1652, the second opening 1654, the passageway 1656, the first track 1658, the second track 1660, and the plurality of mounting passageways 1663 is cooperatively defined by the first and second portions 1615, 1617. The passageway 1656 extends from the first opening 1652 to the second opening 1654 and has a first portion 1664, a second portion 1666, a third portion 1668, a fourth portion 1670, and a fifth portion 1672. The passageway 1656 is sized and configured to receive an implantable medical device, a loading puller, and a portion of a delivery system, such as those described herein. The first portion 1664 extends from the first end 1646 to the second portion and has a constant inside diameter. Alternative embodiments, however, could omit the inclusion of a first portion (e.g., first portion 1664). The second portion 1666 extends from the first portion 1664 to the third portion 1668 and has an inside diameter 1667 that tapers from the first portion 1664 to the third portion 1668. The third portion 1668 extends from the second portion 1666 to the fifth portion 1672 and has an inside diameter 1669 that is less than the inside diameter 1667 of the first portion 1664 at the first end 1646. The third portion 1668 is sized and configured to receive a portion of an implantable medical device, a loading puller, and a portion of a delivery system (e.g., gripping member). The fourth portion 1670 extends from the third portion 1668 to the second end 1648 and has a width 1671 that is greater than the inside diameter 1669 of the third portion 1668. The fourth portion 1670 is sized and configured to receive a portion of a loading puller in the open, or partially opened, configuration, as described in more detail herein. The fifth portion 1672 extends from the third portion 1668 (e.g., a location between the second end 1648 and the third portion 1668) to the second end 1648 and has an inside diameter 1673 that is less than the width 1671 of the fourth portion 1670 and greater than the inside diameter 1669 of the third portion 1668. The fifth portion 1672 is sized and configured to receive a portion of a sheath of a delivery system, as described in more detail herein. The decrease in diameter between the fifth portion 1672 and the third portion 1668 creates a shoulder 1674 that acts as a mechanical stop to advancement of a sheath of delivery system through the passageway 1656. In the illustrated embodiment, the third portion 1668 has a first cross-sectional configuration taken along a plane orthogonal to the lengthwise axis 1644 (e.g., circular cross-sectional configuration), the fourth portion 1670 extends from the third portion 1668 (e.g., a location between the second end 1648 and the second portion 1666) to the second end 1648 and has a second cross-sectional configuration taken along a plane orthogonal to the lengthwise axis 1644 (e.g., elongated cross-sectional configuration, rectangular cross-sectional configuration), and the fifth portion 1672 has a third cross-sectional configuration taken along a plane orthogonal to the lengthwise axis 1644 (e.g., circular cross-sectional configuration). In the illustrated embodiment, the first and third cross-sectional configurations are the same and are circular and the second cross-sectional configuration is different than the first and third cross-sectional configurations and is elongated.

In use, when a loading puller is pulled through the passageway 1656 the loading puller is compressed as its moves through the second portion 1666 of the passageway 1656 and then expands when it reaches the fourth portion 1670 of the passageway 1656.

Each of the first track 1658 and the third track 1662 is disposed on a plane that contains the lengthwise axis 1644 of the loading member, extends into the main body 1650 to a base 1651, and extends from the first end 1646 to the fourth portion 1670. However, alternative embodiments can define a first track and a second track such that each of the first and second tracks are disposed on a plane that does not contain, or contact, the lengthwise axis of the loading member, or such that only one of the first and second tracks is disposed on a plane that contains, or contacts the lengthwise axis of the loading member. Each of the first track 1658 and the third track 1662 has a thickness measured on a place orthogonal to the lengthwise axis 1644 when the first and second portions 1615, 1617 of the loading member 1614 are attached to one another. The distance between the base 1651 of the first track 1658 and the base 1651 of the third track 1662 along the first portion 1664 of the passageway 1656 is greater than the inside diameter of the first portion 1664. The distance between the base 1651 of the first track 1658 and the base 1651 of the third track 1662 along the second portion 1666 of the passageway 1656 is greater than the inside diameter 1667 of the second portion 1666. The distance between the base 1651 of the first track 1658 and the base 1651 of the third track 1662 along the third portion 1668 of the passageway 1656 is greater than the inside diameter 1669 of the third portion 1668 and less than the width 1674 of the fourth portion 1670. Each of the second track 1660 and fourth track 1677 extends from the first end 1646 to the fifth portion 1672. In alternative embodiments, a second track and a fourth track can be omitted from a loading member. Each of the first track 1658 and third track 1662 is sized and configured to receive a portion of a loading puller and provides a mechanism to guide the loading puller through the loading member 1614 during use. Each of the second track 1660 and fourth track 1677 is sized and configured to receive a portion of an implantable medical device. For example, in embodiments in which the implantable medical device includes a frame that has a portion that extends outwardly from the lengthwise axis of the frame (e.g., one or more markers, one or more barbs), one of, or each of, the second track and fourth track provides a mechanism to guide the implantable medical device through the loading member 1614 during use.

Each passageway of the plurality of mounting passageways 1663 is sized and configured to align with the second set of apertures 1640 of the guide board 1612 such that one or more alignment pins (not shown) can be positioned within the passageways and apertures to maintain the position of the loading member 1614 relative to the guide board 1612. Each of the guide pins 1665 extends from the first end 1646 of the first portion 1615 of the loading member 1614, away from the second end 1648, and is sized and configured to be received by a passageway (e.g., passageway 280, passageway 282) defined by a storage member to achieve alignment between the storage member and the loading member 1614.

The guide member 1616 is disposed within the notch 1634 and is releasably attachable to the guide board 1612 using mounting pins (not shown). The guide member 1616 has a first portion 1619 releasably attached to a second portion 1621 using the mounting pins. The guide member 1616 has a lengthwise axis 1675, a first end 1676, a second end 1678, and a main body 1680 that defines a first opening 1682, a second opening 1684, a passageway 1686, and a plurality of mounting passageways 1688. Each of the first opening 1682, the second opening 1684, the passageway 1686, and the plurality of mounting passageways 1688 is cooperatively defined by the first and second portions 1619, 1621. The passageway 1686 extends from the first opening 1682 to the second opening 1684 and is sized and configured to receive a portion of a delivery system (e.g., sheath), such as those described herein. The guide member 1616 provides a mechanism to maintain the position of a delivery system while loading an implantable medical device, as described in more detail herein. Each passageway of the plurality of mounting passageways 1688 is sized and configured to align with the first set of apertures 1638 of the guide board 1612 such that one or more mounting pins (not shown) can be positioned within the passageways and apertures to maintain the position of the guide member 1616 relative to the guide board 1612. While the guide board 1612, loading member 1614, and guide member 1616 have been illustrated as separate elements, a guide board can be an integrated component with a loading member and/or a guide member. For example, a guide member can be permanently attached to a guide board.

Figure 37:
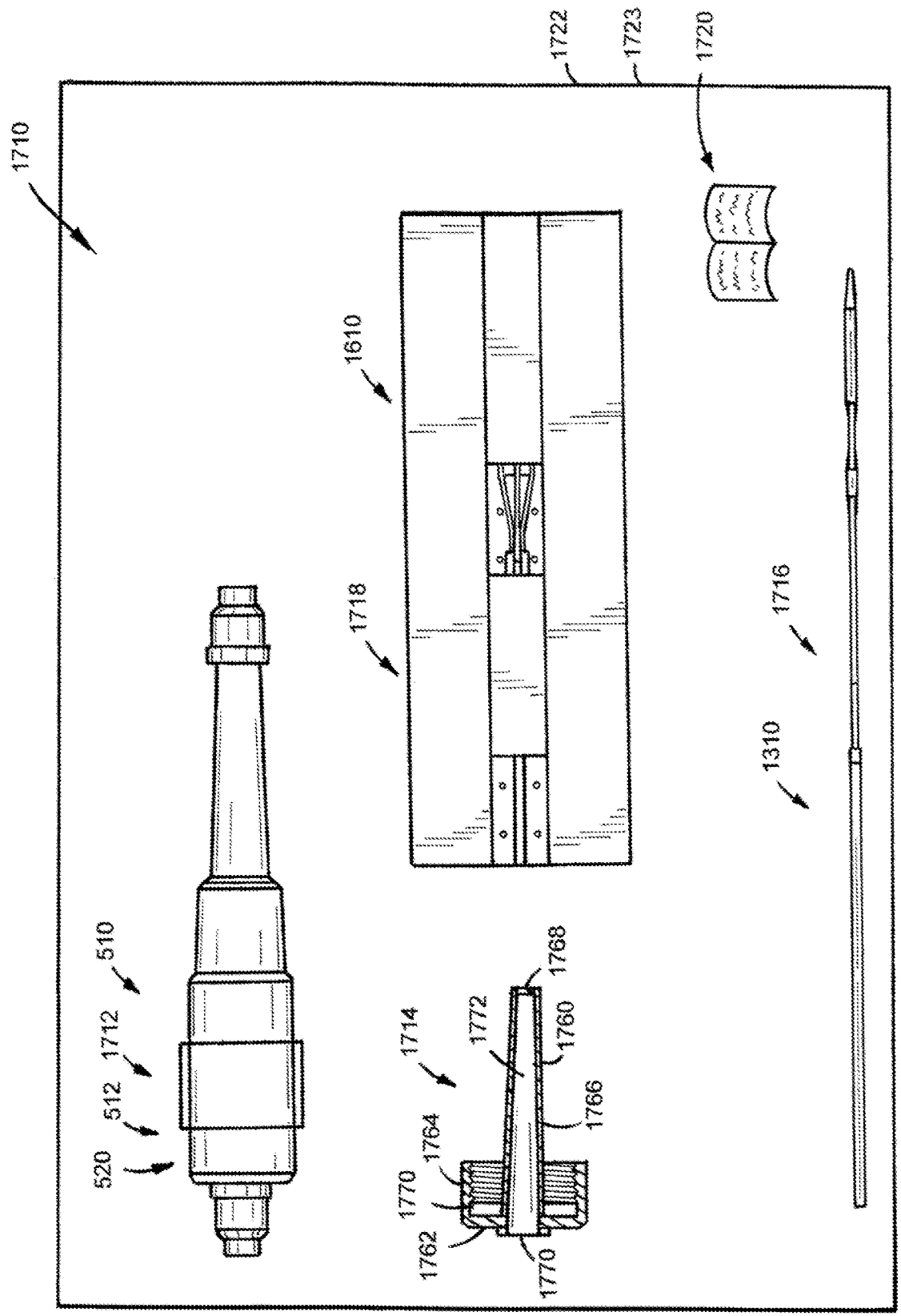
FIG. 37 illustrates an example kit that includes a storage device.

FIG. 37 illustrates an example kit 1710 that includes a storage device 1712 according to an embodiment; a device guard 1714 according to an embodiment; a delivery system 1716 according to an embodiment; a guide system 1718 according to an embodiment; instructions for use 1720; and a storage container 1722.

Any suitable storage device, device guard, delivery system, loading member, loading assister, loading puller, and guide system can be included in a kit and selection of a suitable storage device, device guard, delivery system, loading member, loading assister, loading puller, and guide system to include in a kit can be based on various considerations, including the type of implantable medical device intended to be implanted using the kit. Examples of storage devices considered suitable to include in a kit include storage device 10, storage device 110, storage device 210, storage device 310, storage device 510, variations of the storage devices described herein, and any other storage device according to an embodiment. Examples of device guards considered suitable to include in a kit include device guard 146, device guard 715, device guard 1714, device guard 2615, variations of the device guards described herein, and any other device guard according to an embodiment. Examples of delivery systems considered suitable to include in a kit include delivery system 1210, delivery system 1310, delivery system 1410, delivery system 2510, variations of the delivery systems described herein, and any other delivery system according to an embodiment. Examples of loading members considered suitable to include in a kit include loading member 712, loading member 1012, loading member 1614, loading member 2814, variations of the loading members described herein, and any other loading member according to an embodiment.

Examples of loading assisters considered suitable to include in a kit include loading assister 2710, and any other loading assister considered suitable for a particular embodiment. Examples of loading pullers considered suitable to include in a kit include loading puller 652, loading puller 2752, and any other loading puller considered suitable for a particular embodiment. Examples of guide systems considered suitable to include in a kit include guide system 1610, variations of the guide systems described herein, and any other guide system according to an embodiment. In the illustrated embodiment, the kit 1710 includes storage device 510, as shown in FIGS. 15, 16, and 16A, delivery system 1410, as shown in FIG. 30, and guide system 1610, as shown in FIGS. 33, 34, 35, and 36.

In the illustrated embodiment, the device guard 1714 is similar to the device guard 715 illustrated in FIG. 17 and described above, except as detailed below. The device guard 1714 is releasably attachable to the first end 520 of the storage member 512 and the main body 1760 of the device guard 1714 defines a base 1762, a sidewall 1764, a projection 1766, a first opening 1768, a second opening 1770, and a passageway 1772. The base 1762 and the sidewall 1764 cooperatively define a cavity 1770 that is sized and configured to receive a portion of the storage member 512. The projection 1766 extends from the base 1762, through the cavity 1770, and to an environment exterior to the cavity 1770. The passageway 1772 extends from the first opening 1768 to the second opening 1770 and is sized and configured to receive a portion of a delivery system, as described in more detail herein.

While the kit 1710 has been illustrated as including a single a storage device 510, a single device guard 1714, a single delivery system 1310, and a single guide system 1610, any suitable number, and type, of storage devices, device guards, delivery systems, loading members, loading pullers, loading assisters, and/or guide systems can be included in a kit, such as those described herein. Selection of a suitable number of storage devices, device guards, delivery systems, loading members, loading pullers, loading assisters, and/or guide systems to include in a kit according to a particular embodiment can be based on various considerations, such as the type of implantable medical device intended to be implanted using the kit. Examples of suitable numbers of storage devices, device guards, delivery systems, loading members, loading pullers, loading assisters, and/or guide systems to include in a kit include at least one, one, two, a plurality, three, four and any other number considered suitable for a particular embodiment.

While the kit 1710 has been illustrated as including only a storage device 1712, a device guard 1714, a delivery system 1716, a guide system 1718, instructions for use 1720, and a storage container 1720, a kit can include any suitable number of optional components. Examples of numbers of optional components considered suitable to include in a kit, such as an implantable medical device (e.g., disposed within a storage device, provided free of a storage device, pre-attached to a loading puller, pre-attached to a loading puller and disposed within a container, pre-attached to a loading puller and disposed within a loading member), include one, at least one, two, a plurality, three, four, five, more than five, and any other number considered suitable for a particular embodiment. Examples of optional components and/or devices considered suitable to include in a kit include containers, or bags (e.g., I.V. bag) filled with saline, lubricant, a rinsing solution, or a flushing solution, tubing, bowls, guide wires, catheters, syringes, and/or any other component and/or device considered suitable for a particular embodiment.

A storage container included in a kit can have any suitable structural arrangement and be formed of any suitable material and selection of a suitable structural arrangement and material to form a storage container can be based on various considerations, including the number of storage devices, device guards, delivery systems, loading members, and/or guide systems included in a kit. Examples of structural arrangements considered suitable to form a storage container include boxes, boxes that include a lid, boxes that include a lid attached to the box (e.g., pivotably attached), bags, and any other structural arrangement considered suitable for a particular embodiment. Examples of materials considered suitable to form a storage container include metals, plastics, glass, combinations of the materials described herein, and any other material considered suitable for a particular embodiment. In the illustrated embodiment, the storage container 1722 is a box 1723 formed of a rigid plastic.

Figure 38:
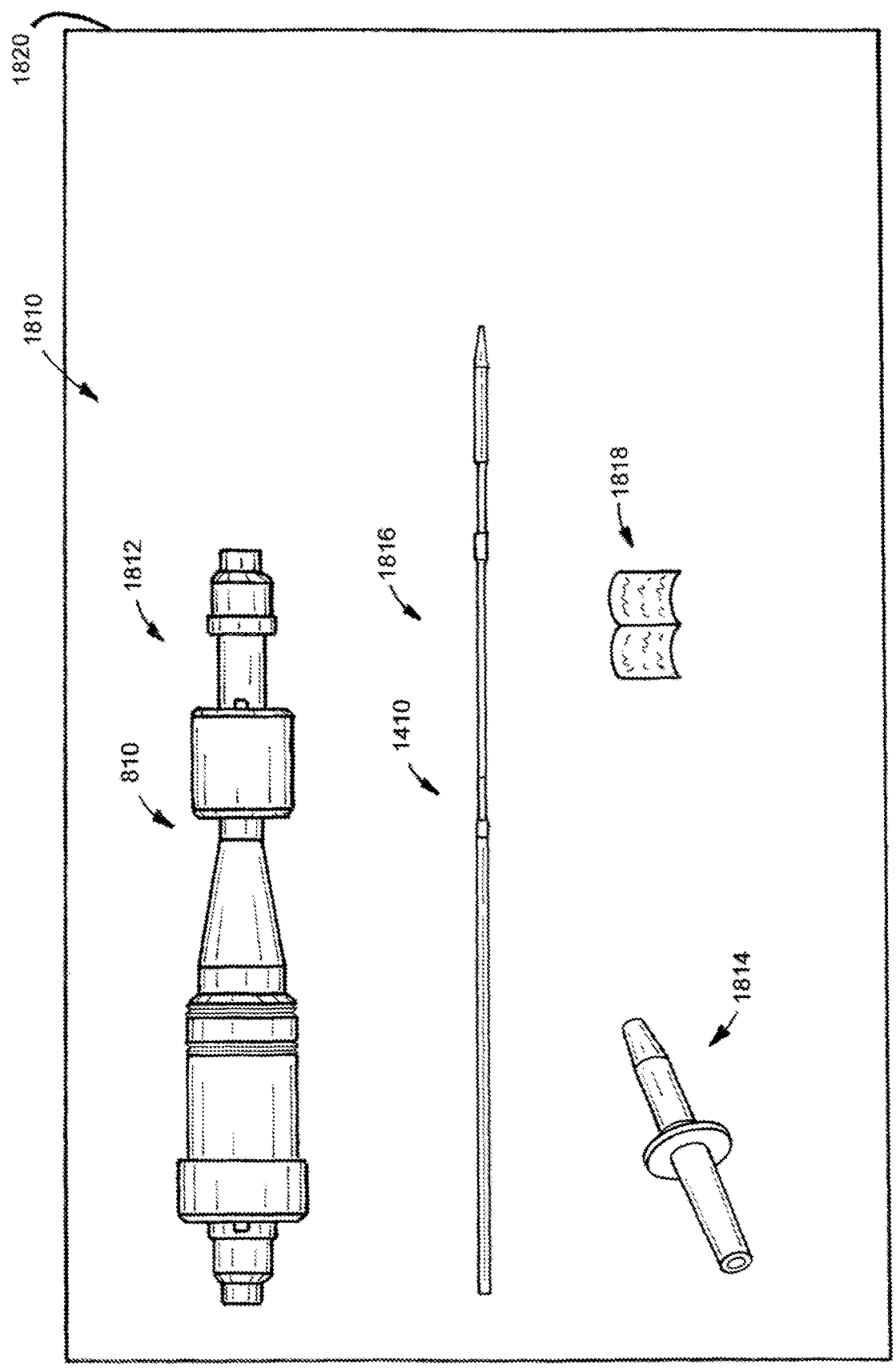
FIG. 38 illustrates an example kit that includes a loading device.

FIG. 38 illustrates an example kit 1810 that includes a loading device 1812 according to an embodiment; a device guard 1814 according to an embodiment; a delivery system 1816 according to an embodiment; instructions for use 1818; and a storage container 1820.

Any suitable loading device, device guard, and delivery system can be included in a kit and selection of a suitable loading device, device guard, and delivery system to include in a kit can be based on various considerations, including the type of implantable medical device intended to be implanted using the kit. Examples of loading devices considered suitable to include in a kit include loading device 710, loading device 810, variations of the loading devices described herein, and any other loading device according to an embodiment. Examples of device guards considered suitable to include in a kit include device guard 146, device guard 715, device guard 1714, device guard 2615, variations of the device guards described herein, and any other device guard according to an embodiment. Examples of delivery systems considered suitable to include in a kit include delivery system 1210, delivery system 1310, delivery system 1410, delivery system 2510, variations of the delivery systems described herein, and any other delivery system according to an embodiment. In the illustrated embodiment, the kit 1810 includes loading device 810, as shown in FIGS. 18, 19, 20, 21, 22, 23, 24, 25, and 26, and delivery system 1410, as shown in FIG. 30.

While the kit 1810 has been illustrated as including a single a loading device 1812, a single device guard 1814, and a single delivery system 1816, any suitable number, and type, of loading devices, device guards, and/or delivery systems can be included in a kit, such as those described herein. Selection of a suitable number of loading devices, device guards, and/or delivery systems to include in a kit according to a particular embodiment can be based on various considerations, such as the type of implantable medical device intended to be implanted using the kit. Examples of suitable numbers of loading devices, device guards, and/or delivery systems to include in a kit include at least one, one, two, a plurality, three, four and any other number considered suitable for a particular embodiment.

While the kit 1810 has been illustrated as including only a loading device 1812, a device guard 1814, a delivery system 1816, instructions for use 1818, and a storage container 1820, a kit can include any suitable number of optional components. Examples of numbers of optional components considered suitable to include in a kit, such as an implantable medical device (e.g., disposed within a loading device, provided free of a loading device, pre-attached to a loading puller, pre-attached to a loading puller and disposed within a container, pre-attached to a loading puller and disposed within a loading member), include one, at least one, two, a plurality, three, four, five, more than five, and any other number considered suitable for a particular embodiment. Examples of optional components and/or devices considered suitable to include in a kit include containers, or bags (e.g., I.V. bag) filled with saline, lubricant, a rinsing solution, or a flushing solution, tubing, bowls, guide wires, catheters, syringes, and/or any other component and/or device considered suitable for a particular embodiment.

A storage member, a cap, a device guard, a one-way valve, a two-way valve, a diffuser, a loading member, a loading puller, a loading assister, a connector, a catheter, an elongate member, a pushing member, a tip, a guide board, a guide member, and any other device, component, element, or feature of the embodiments described herein can be formed of any suitable material and using any suitable method of manufacture. Selection of a suitable material and method of manufacture can be based on various considerations, including the intended use of the device, component, element, or feature. Examples of materials considered suitable to form a storage member, a cap, a device guard, a one-way valve, a two-way valve, a diffuser, a loading member, a loading puller, a loading assister, a connector, a catheter, an elongate member, a pushing member, a tip, a guide board, a guide member, and any other device, component, element, or feature of the embodiments described herein include biocompatible materials, materials that can be made biocompatible, metals, plastics, polymers, transparent materials, opaque materials, and any other material considered suitable for a particular embodiment. Optionally, any of the storage member, a cap, a device guard, a one-way valve, a two-way valve, a diffuser, a loading member, a loading puller, a loading assister, a connector, a catheter, an elongate member, a pushing member, a tip, a guide board, a guide member, and any other device, component, element, or feature of the embodiments described herein can include a gasket (e.g., o-ring) disposed between it and another element to which it is attached.

Any attachment between a storage member, a cap, a device guard, a one-way valve, a diffuser, a loading member, a loading puller, a loading assister, a connector, a catheter, an elongate member, a pushing member, a tip, a guide board, a guide member, and another element described herein can utilize any suitable technique or method of attachment between the elements. Selection of a suitable technique or method of attachment between two elements can be based on various considerations, including the material(s) that forms the elements. Examples of techniques and methods of attachment considered suitable between two elements described herein include those illustrated, using threaded connections, snap fit attachments, using one or more connectors, one or more mating slots and projections, pierceable membranes between the elements, releasable attachments, permanent attachments, and any other technique or method of attachment considered suitable for a particular application.

Various methods sterilizing an implantable medical device, storing an implantable medical device, rinsing an implantable medical device, and loading an implantable medical device onto a delivery system are described herein. While the methods described herein are shown and described as a series of acts, it is to be understood and appreciated that the methods are not limited by the order of acts, as some acts may in accordance with these methods, occur in the order shown and/or described, in different orders, and/or concurrently with other acts described herein.

Figure 39:
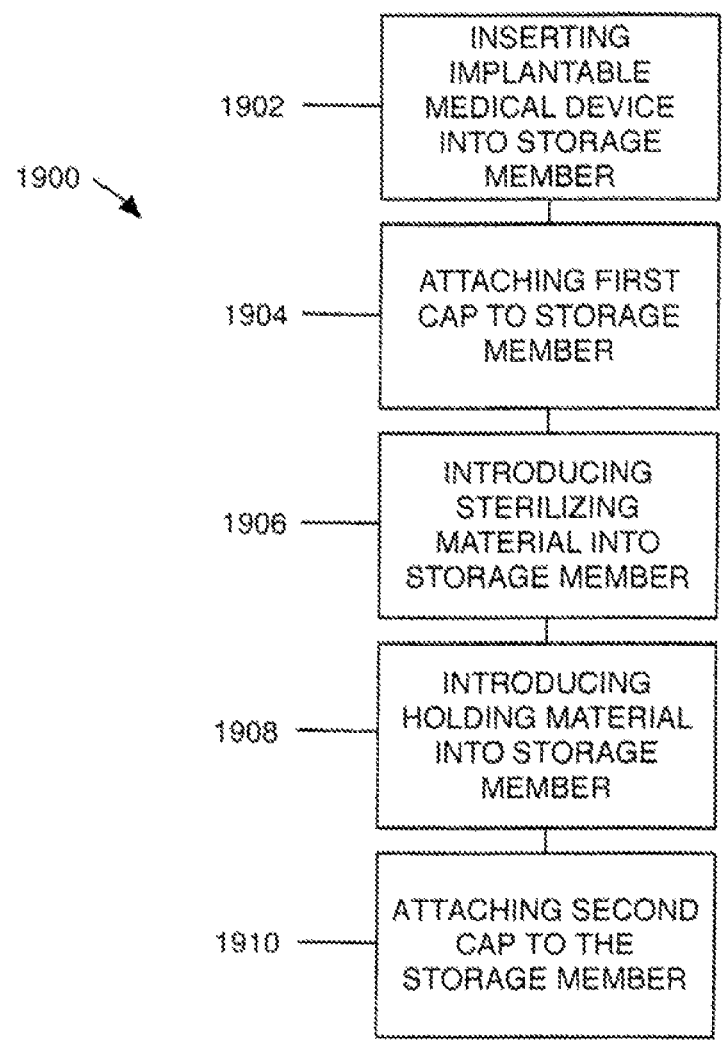
FIG. 39 is a schematic illustration of an example method of sterilizing an implantable medical device.

FIG. 39 is a schematic illustration of an example method 1900 of sterilizing an implantable medical device.

A step 1902 comprises inserting an implantable medical device into a storage member. Another step 1904 comprises attaching a first cap to the storage member. Another step 1906 comprises introducing a sterilizing material into the storage member. Another step 1908 comprises introducing a holding material into the storage member such that the sterilizing material is removed from the storage member. Another step 1910 comprises attaching a second cap to the storage member.

Step 1902 can be accomplished using any suitable implantable medical device, such as those described herein. In the illustrated embodiment, the example method of sterilizing an implantable medical device 1900 comprises a method of sterilizing a valve device. Step 1902 can be accomplished by applying an axial force on the implantable medical device along the lengthwise axis of a storage member and directed toward an end (e.g., the first end, the second end) of the storage member until the implantable medical device is disposed within a portion of the passageway defined by the storage member (e.g., first portion, second portion). Any suitable storage member can be used to complete method 1900, such as the storage members described herein. An optional step that can be completed prior to, or subsequent to, step 1902 comprises releasably attaching a loading puller to the implantable medical device.

Step 1904 can be accomplished using any suitable cap, such as the caps described herein, and the cap can be attached to either the first or second end of the storage member. Alternatively, step 1904 can comprise attaching a loading member to a storage member and can be accomplished using any suitable loading member, such as the loading members described herein.

Step 1906 can be accomplished using any suitable method or technique of introducing a sterilizing material into storage member (e.g., using a syringe) and by passing the sterilizing material through the first opening or second opening of the storage member such that it accumulates within the passageway defined by the storage member (e.g., within only the second portion of the passageway, within only the first portion of the passageway, within both the first portion and the second portion of the passageway), or passes through the passageway. Any suitable sterilizing material can be introduced into a storage member and selection of a suitable sterilizing material can be based on various considerations, including the type of implantable medical device disposed within the storage member. Examples of sterilizing materials include glutaraldehyde, formaldehyde, alcohol, and any other sterilizing material considered suitable for a particular embodiment. An optional step comprises removing the sterilizing material from the storage member. Optionally, step 1906 can be accomplished prior to step 1904.

Step 1908 can be accomplished using any suitable method or technique of introducing a holding material into storage member (e.g., using a syringe) and by passing the holding material through the first opening or second opening of the storage member such that it accumulates within the passageway defined by the storage member (e.g., within only the second portion of the passageway, only within the first portion of the passageway, within both the first portion and the second portion of the passageway), or passes through the passageway, and replaces any sterilizing material in the storage member. Any suitable holding material can be introduced into a storage member and selection of a suitable holding material can be based on various considerations, including the type of implantable medical device disposed within the storage member. Examples of holding materials include glutaraldehyde, saline, formaldehyde, phosphate buffers, phosphate buffered saline (PBS), agents, biological agents, coatings, absorbable coatings, drugs, quenching solutions, quenching solutions that may include an amino acid, anti-calcification materials, rinsing fluids, flushing fluids, and any other holding material considered suitable for a particular embodiment. Optionally, step 1908 can be completed multiple times (e.g., two times, three times). Optionally, step 1908 can be accomplished prior to step 1904 and after step 1906.

Figure 40:
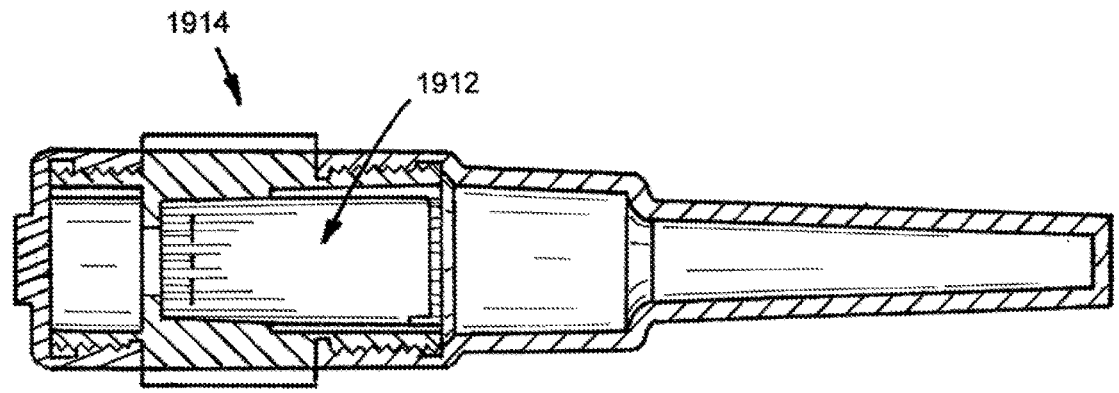
FIG. 40 is a cross-sectional view of an implantable medical device stored within an example storage member.

Step 1910 can be accomplished using any suitable cap, such as the caps described herein, and the cap can be attached to the first or second end of a storage member that does not include a cap. In an alternative embodiment, step 1904 can comprise attaching a cap to the storage member and step 1910 can comprise attaching a loading member to a storage member. FIG. 40 illustrates an implantable medical device 1912 stored within an example storage member 1914.

While various steps, alternative steps, and optional steps have been described above with respect to the example method 1900, these steps, alternative steps, and optional steps can be included in, accomplished concurrently with, and/or accomplished in the alternative to, the method, steps, alternative steps, and/or optional steps described herein with respect to the example method 2000, example method 2100, example method 2200, example method 2300, example method 2400, and/or example method 2900.

Figure 41:
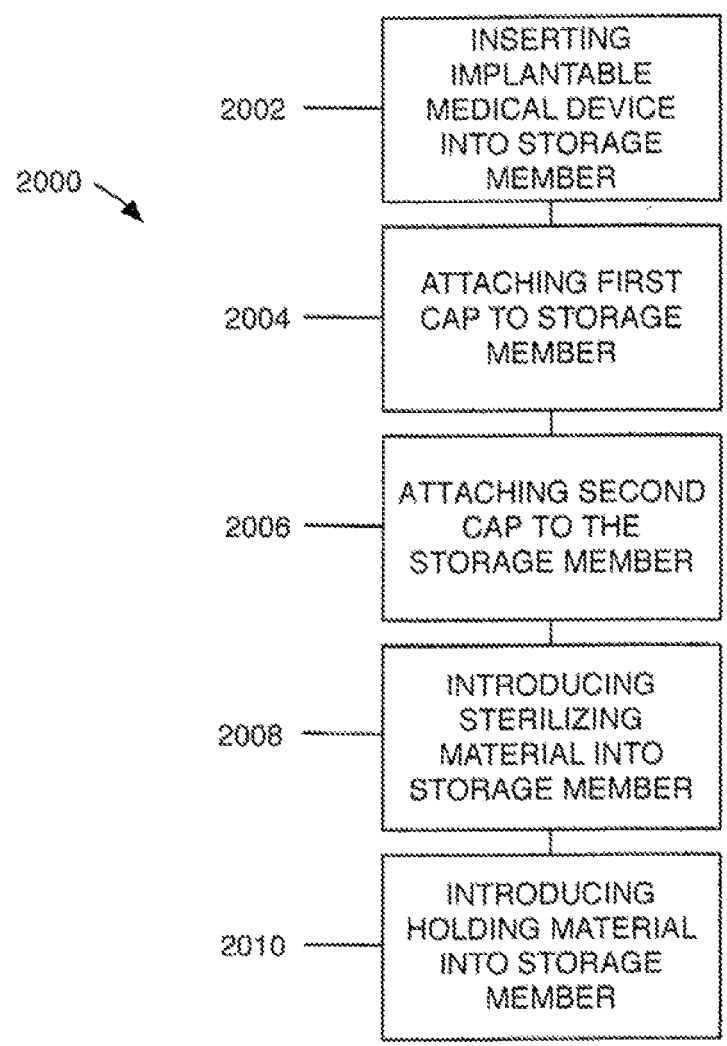
FIG. 41 is a schematic illustration of another example method of sterilizing an implantable medical device.

FIG. 41 is a schematic illustration of another example method 2000 of sterilizing an implantable medical device.

A step 2002 comprises inserting an implantable medical device into a storage member. Another step 2004 comprises attaching a first cap to the storage member. Another step 2006 comprises attaching a second cap to the storage member. Another step 2008 comprises introducing a sterilizing material into the storage member. Another step 2010 comprises introducing a holding material into the storage member such that the sterilizing material is removed from the storage member.

Step 2002 can be accomplished as described above with respect to step 1902.

Step 2004 can be accomplished using any suitable cap, such as the caps described herein, and the cap can be attached to either the first or second end of the storage member. Alternatively, step 2004 can comprise attaching a loading member to a storage member and can be accomplished using any suitable loading member, such as the loading members described herein.

Step 2006 can be accomplished using any suitable cap, such as the caps described herein, and the cap can be attached to the first or second end of a storage member that does not include a cap.

Step 2008 can be accomplished using any suitable method or technique of introducing a sterilizing material into storage member such that the sterilizing material is passed through the first opening or second opening of the storage member and accumulates within the passageway defined by the storage member (e.g., within only the second portion of the passageway, within only the first portion of the passageway, within both the first portion and the second portion of the passageway), or passes through the passageway. For example, a syringe or a line connected to a bag containing a sterilizing material can be attached to a first one-way valve and be utilized to introduce the sterilizing fluid into the storage member such that the sterilizing material is contained within the storage member and does not pass through the second one-way valve. Alternatively, a syringe or a line connected to a bag can be used to pass the sterilizing fluid through the second one-way valve and into the storage member, or through the first one-way valve, the storage member, and the second one-way valve, or through the second one-way valve, the storage member, and the first one-way valve. Any suitable sterilizing material can be introduced into a storage member, such as those described herein. An optional step comprises removing the syringe or line from the one-way valve.

Figure 42:
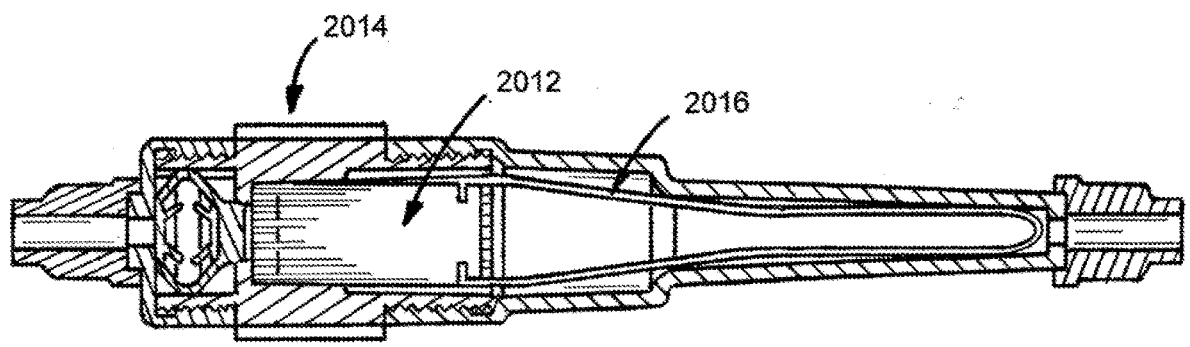
FIG. 42 is a cross-sectional view of an implantable medical device stored within an example storage member.

Step 2010 can be accomplished using any suitable method or technique of introducing a holding material into storage member such that the holding material is passed through the first opening or second opening of the storage member and accumulates within the passageway defined by the storage member (e.g., within only the second portion of the passageway, within only the first portion of the passageway, within both the first portion and the second portion of the passageway), or passes through the passageway. For example, a syringe or a line connected to a bag containing a holding material can be attached to a first one-way valve and be utilized to introduce the holding fluid into the storage member such that the holding material is contained within the storage member and does not pass through the second one-way valve. Alternatively, a syringe or a line connected to a bag can be used to pass the holding fluid through the second one-way valve and into the storage member, or through the first one-way valve, the storage member, and the second one-way valve, or through the second one-way valve, the storage member, and the first one-way valve. An optional step comprises removing the syringe or line from the one-way valve. Any suitable holding material can be introduced into a storage member, such as those described herein. Optionally, step 2010 can be completed multiple times (e.g., two times, three times). Each time step 2010 is completed, it can be completed for a particular period of time (e.g., 1 minute, 5 minutes) and/or until a specified volume of holding fluid has been passed through storage member. FIG. 42 illustrates an implantable medical device 2012 stored within an example storage member 2014 and a loading puller 2016 that defines only first and second bends and a curve between the first and second bends pre-attached to the implantable medical device 2012.

While various steps, alternative steps, and optional steps have been described above with respect to the example method 2000, these steps, alternative steps, and optional steps can be included in, accomplished concurrently with, and/or accomplished in the alternative to, the method, steps, alternative steps, and/or optional steps described herein with respect to the example method 1900, example method 2100, example method 2200, example method 2300, example method 2400, and/or example method 2900.

Figure 43:
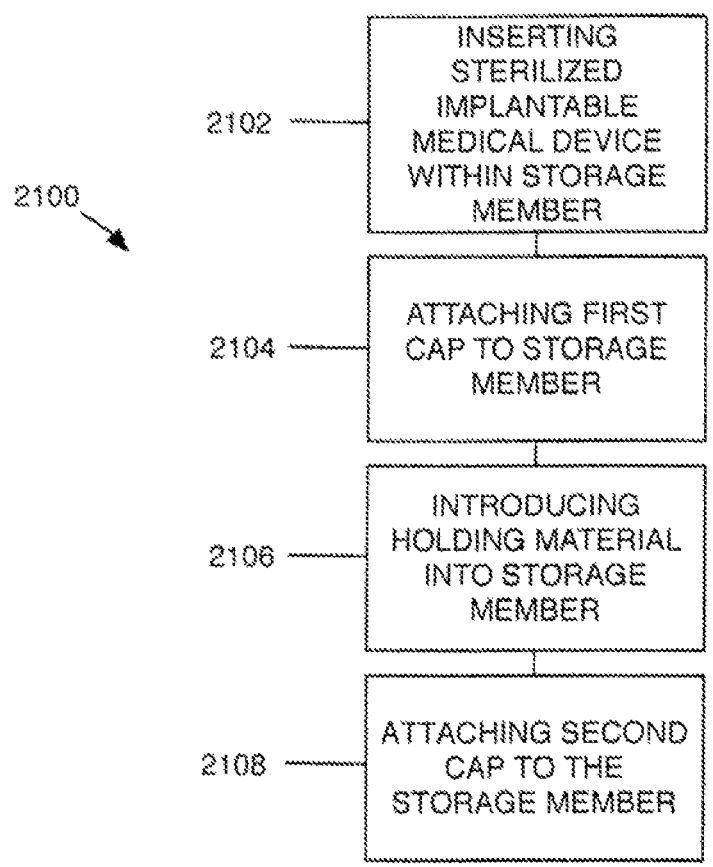
FIG. 43 is a schematic illustration of an example method storing an implantable medical device.

FIG. 43 is a schematic illustration of an example method 2100 of storing an implantable medical device.

A step 2102 comprises inserting a sterilized implantable medical device into a storage member. Another step 2104 comprises attaching a first cap to the storage member. Another step 2106 comprises introducing a holding material into the storage member. Another step 2108 comprises attaching a second cap to the storage member.

Step 2102 can be accomplished as described above with respect to step 1902. Optional steps that can be completed prior to step 2102 include: sterilizing the implantable medical device; rinsing the implantable medical device; and/or attaching a loading puller to the implantable medical device. These optional steps can be accomplished using conventional sterilization and/or rinsing methods or those described herein. In alternative embodiments, step 2102 can comprise obtaining a sterilized implantable medical device disposed within a storage member.

Step 2104 can be accomplished using any suitable cap, such as the caps described herein, and the cap can be attached to either the first or second end of the storage member. Alternatively, step 2104 can comprise attaching a loading member to a storage member and can be accomplished using any suitable loading member, such as the loading members described herein.

Step 2106 can be accomplished using any suitable method or technique of introducing a holding material into storage member (e.g., using a syringe) and by passing the holding material through the first opening or second opening of the storage member such that it accumulates within the passageway defined by the storage member (e.g., within only the second portion of the passageway, within only the first portion of the passageway, within both the first portion and the second portion of the passageway), or passes through the passageway. Any suitable holding material can be introduced into a storage member, such as those described herein. Optionally, step 2106 can be completed multiple times (e.g., two times, three times). Optionally, step 2106 can be accomplished prior to step 2104 or subsequent to step 2108. In embodiments in which step 2106 is accomplished subsequent to step 2108, step 2106 can be accomplished using any suitable method or technique of introducing a holding material into storage member such that the holding material is passed through the first opening or second opening of the storage member and accumulates within the passageway defined by the storage member (e.g., within only the second portion of the passageway, within only the first portion of the passageway, within both the first portion and the second portion of the passageway), or passes through the passageway. For example, a syringe containing a holding material can be attached to a first one-way valve and be utilized to introduce the holding fluid into the storage member such that the holding material is contained within the storage member and does not pass through the second one-way valve. Alternatively, a syringe can be used to pass the holding fluid through the second one-way valve and into the storage member, or through the first one-way valve, the storage member, and the second one-way valve, or through the second one-way valve, the storage member, and the first one-way valve. In this embodiment, step 2106 can be completed multiple times (e.g., two times, three times). Each time step 2106 is completed, it can be completed for a particular period of time (e.g., 1 minute, 5 minutes) and/or until a specified volume of holding fluid has been passed through storage member. An optional step comprises removing the syringe or line from the one-way valve.

Step 2108 can be accomplished using any suitable cap, such as the caps described herein, and the cap can be attached to the first or second end of a storage member that does not include a cap.

While various steps, alternative steps, and optional steps have been described above with respect to the example method 2100, these steps, alternative steps, and optional steps can be included in, accomplished concurrently with, and/or accomplished in the alternative to, the method, steps, alternative steps, and/or optional steps described herein with respect to the example method 1900, example method 2000, example method 2200, example method 2300, example method 2400, and/or example method 2900.

Figure 44:
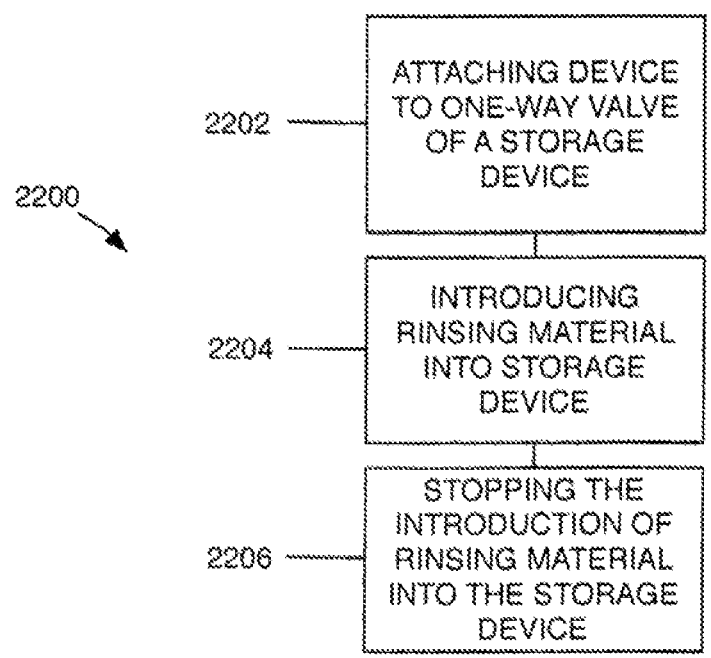
FIG. 44 is a schematic illustration of an example method of rinsing an implantable medical device.

FIG. 44 is a schematic illustration of an example method 2200 of rinsing an implantable medical device.

A step 2202 comprises attaching a device that includes a rinsing material to a one-way valve of a storage device. Another step 2204 comprises introducing the rinsing material into the storage device such that it passes through the storage device. Another step 2206 comprises stopping the step of introducing the rinsing material into the storage device.

Step 2202 can be accomplished using any suitable method or technique of attachment and using any suitable device that includes a rinsing material, such as syringe, a line attached to a bag that includes a rinsing material, and any other device considered suitable for a particular embodiment. Any suitable rinsing material can be included in a device and selection of a suitable rinsing material can be based on various considerations, including the type of implantable medical device disposed within a storage member. Examples of rinsing materials include saline, agents, biological agents, coatings, absorbable coatings, drugs, phosphate buffers, phosphate buffered saline (PBS), and any other rinsing material considered suitable for a particular embodiment. In the embodiment described, a device is attached to a first one-way valve of a storage device. However, alternative embodiments can include a device that is attached to a second one-way valve, or a two-way valve, of a storage device.

While step 2202 has been described as being completed by attaching a device to a storage device, an alternative embodiment can include attaching a device to a loading device. Step 2202 can be accomplished by attaching the device to a first one-way valve of a storage device and/or loading device, a first two-way valve of a storage device and/or loading device, a second one-way valve of a storage device and/or loading device, or a second two-way valve of a storage device and/or loading device.

Step 2204 can be accomplished using any suitable method or technique of introducing a rinsing material into storage device such that the rinsing material is passed through the first opening or second opening of the storage member and accumulates within the passageway defined by the storage member (e.g., within only the second portion of the passageway, within only the first portion of the passageway, within both the first portion and the second portion of the passageway), or passes through the passageway. Alternatively, a syringe can be used to pass the rinsing fluid through the second one-way valve and into the storage member, or through the first one-way valve, the storage member, and the second one-way valve, or through the second one-way valve, the storage member, and the first one-way valve. Alternatively, a syringe containing a rinsing material can be attached to a first one-way valve and be utilized to introduce the rinsing fluid into the storage member such that the rinsing material is contained within the storage member and does not pass through the second one-way valve. Step 2204 can be completed multiple times (e.g., two times, three times). Each time step 2204 is completed, it can be completed for a particular period of time (e.g., 1 minute, 5 minutes) and/or until a specified volume of rinsing fluid has been passed through storage member.

Optionally, steps 2202, 2204, 2206 can be repeating one or more times using a second rinsing fluid that is different than the rinsing fluid initially passed through the storage member. An optional step comprises agitating the storage member during step 2204 or subsequent to the completion of step 2204.

While method 2200 has been described as being accomplished using a one-way valve, other embodiments can include a storage device and/or loading device that omits the inclusion of one or more one-way valves. In these embodiments, method 2200 can include the steps of: removing a first cap, a second cap, a first one-way valve, and/or a second one-way valve; immersing the storage member in a rinsing material; optionally agitating the storage member; and removing the storage member from the rinsing material. In the methods described herein, any inclusion of a one-way valve can be substituted with a two-way valve in an alternative embodiment.

While various steps, alternative steps, and optional steps have been described above with respect to the example method 2200, these steps, alternative steps, and optional steps can be included in, accomplished concurrently with, and/or accomplished in the alternative to, the method, steps, alternative steps, and/or optional steps described herein with respect to the example method 1900, example method 2000, example method 2100, example method 2300, example method 2400, and/or example method 2900.

Figure 45:
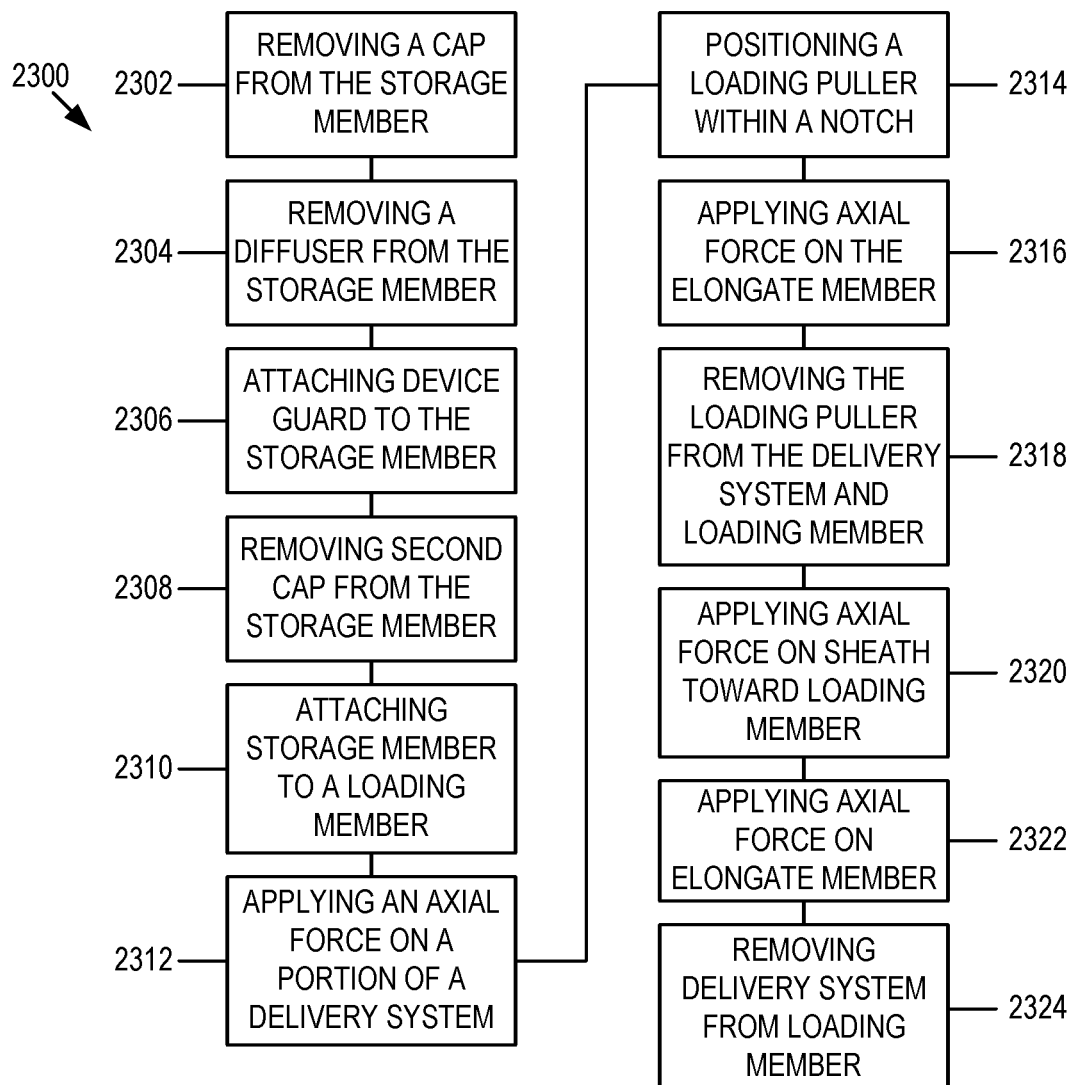
FIG. 45 is a schematic illustration of an example method of loading an implantable medical device onto a delivery system.

FIG. 45 is a schematic illustration of an example method 2300 of loading an implantable medical device onto a delivery system.

A step 2302 comprises removing a first cap from a storage member containing an implantable medical device. Another step 2304 comprises removing a diffuser from the storage member. Another step 2306 comprises attaching a device guard to the storage member. Another step 2308 comprises removing a second cap from the storage member. Another step 2310 comprises attaching the storage member to a loading member of a guide system. Another step 2312 comprises applying an axial force on a portion of a delivery system directed toward a storage member such that it is passed through the storage member, the loading member, and partially disposed within the device guard. Another step 2314 comprises positioning a loading puller within a notch defined by an elongate member of the delivery system. Another step 2316 comprises applying an axial force on the elongate member of the delivery system directed away from the storage member until the first and second ends of the loading puller are disposed within the fourth portion of the loading member. Another step 2318 comprises removing the loading puller from the delivery system and loading member. Another step 2320 comprises applying an axial force on a sheath of the delivery system directed toward the loading member while maintaining the position of the elongate member until the sheath contacts the loading member. Another step 2322 comprises applying an axial force on the elongate member directed away from the storage member while maintaining the position of the sheath such that the elongate member is withdrawn from the loading member and the medical device is advanced into the sheath. Another step 2324 comprises removing the delivery system from the loading member.

Step 2302 can be accomplished by applying a force on a first cap directed away from a storage member such that the cap is removed from the storage member (e.g., axial force, rotational force). The type of force will depend on the type of attachment between the cap and the storage member.

Step 2304 can be accomplished in any suitable manner, such as by applying a force on a diffuser directed away from a storage member in embodiments in which the diffuser is releasably disposed within a storage member. Alternatively, in embodiments in which a diffuser is permanently attached, or releasably attached, to a cap, step 2304 can be accomplished concurrently with step 2302.

Step 2306 can be accomplished by applying a force on a device guard directed toward the storage member until the device guard is attached to the storage member. Step 2306 can be accomplished using any suitable device guard, such as the device guards described herein. In an alternative embodiment, step 2306 can be omitted from a method of loading an implantable medical device onto a delivery system.

Step 2308 can be accomplished by applying a force on a second cap directed away from a storage member such that the cap is removed from the storage member (e.g., axial force, rotational force). The type of force will depend on the type of attachment between the cap and the storage member.

Figure 46:
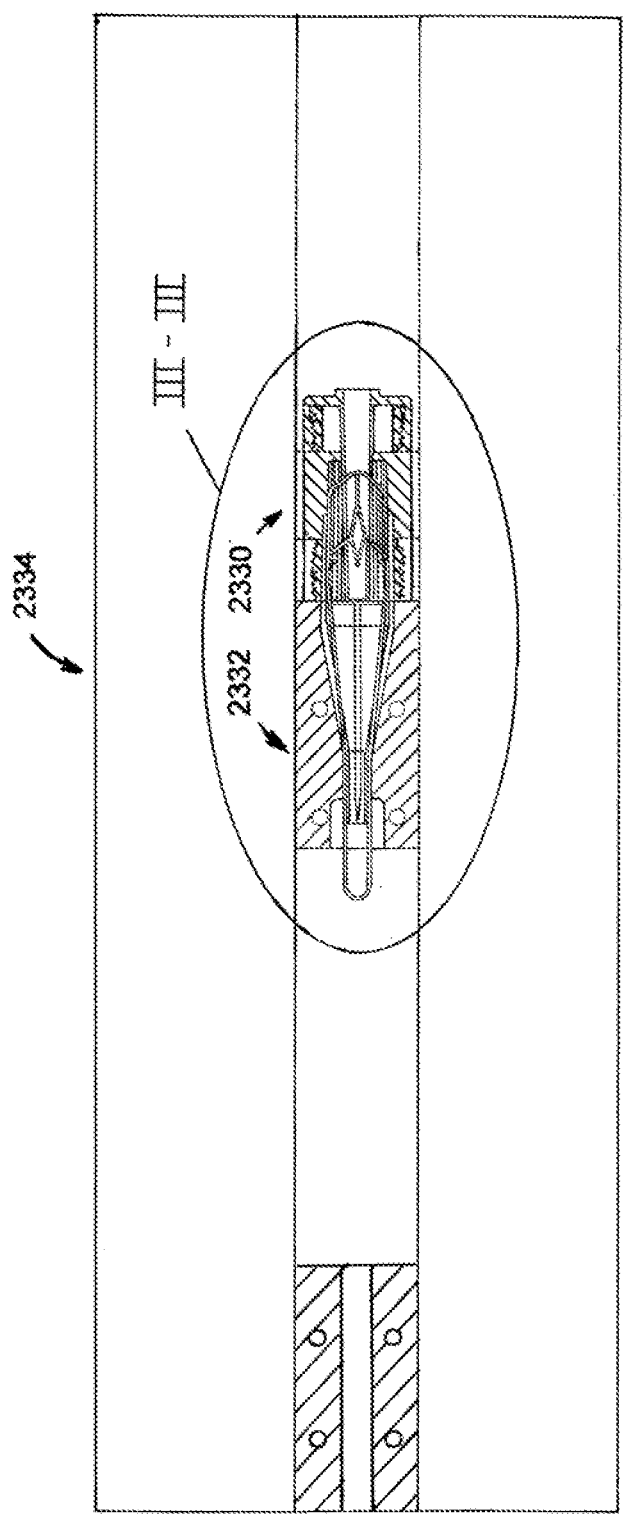
FIG. 46 is a cross-sectional view of a storage member attached to a loading member of a guide system.

Step 2310 can be accomplished by applying a force on a storage member directed toward a loading member until the storage member is attached to the loading member, applying a force on a loading member directed toward a storage member until the storage member is attached to the loading member, or applying a force on a storage member directed toward a loading member and applying a force on a loading member directed toward a storage member until the storage member is attached to the loading member. FIGS. 46 and 46A illustrate a storage member 2330 attached to a loading member 2332 of a guide system 2334.

Step 2312 can be accomplished using any suitable delivery system, such as the delivery systems described herein. Step 2312 can be accomplished by maintaining the position of a sheath and applying an axial force on an elongate member directed toward a loading member until the elongate member is passed through the storage member, the loading member, and is partially disposed (e.g., tip) within the device guard.

Figure 47:
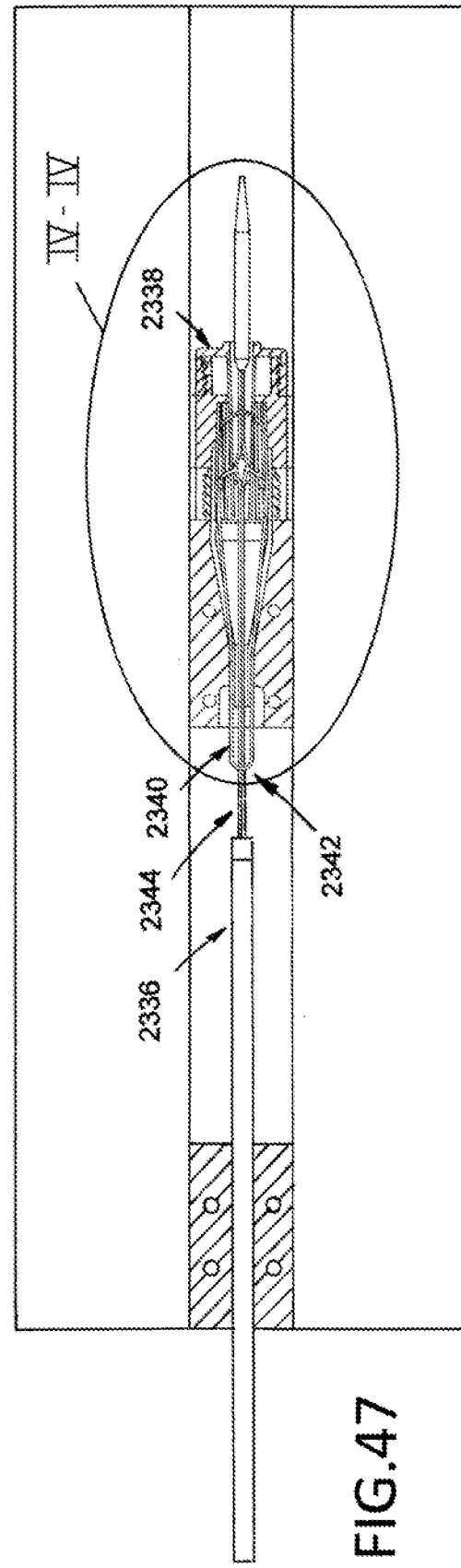
FIG. 47 is a cross-sectional view of a delivery system partially disposed within a device guard and a loading puller disposed within a notch defined by an elongate member.
Figure 48:
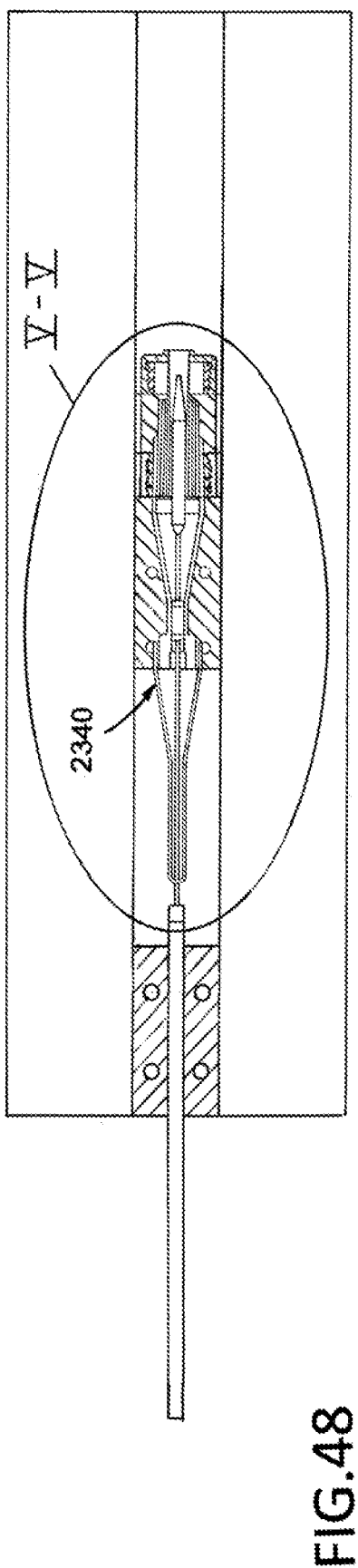
FIG. 48 is a cross-sectional view of a loading puller in an open configuration.

Step 2314 can be accomplished by applying a force on a loading puller directed toward an elongate member of a delivery system until the loading puller is disposed within the notch defined by the elongate member. FIGS. 47 and 47A illustrate a delivery system 2336 partially disposed within the device guard 2338 and the loading puller 2340 disposed within the notch 2342 defined by the elongate member 2344. FIGS. 48 and 48A illustrate the loading puller 2340 in the open configuration, free of the implantable medical device, and disposed within the fourth portion of the loading member. In embodiments in which loading puller 2752, as described in more detail herein, is being utilized, another step comprises applying an axial force on each of the first and second portions directed initially toward the lengthwise axis 2757 of the loading puller 2752 and, once the first and second portions pass the lengthwise axis 2757, away from the lengthwise axis 2757 to move the loading puller to the open configuration.

Figure 49:
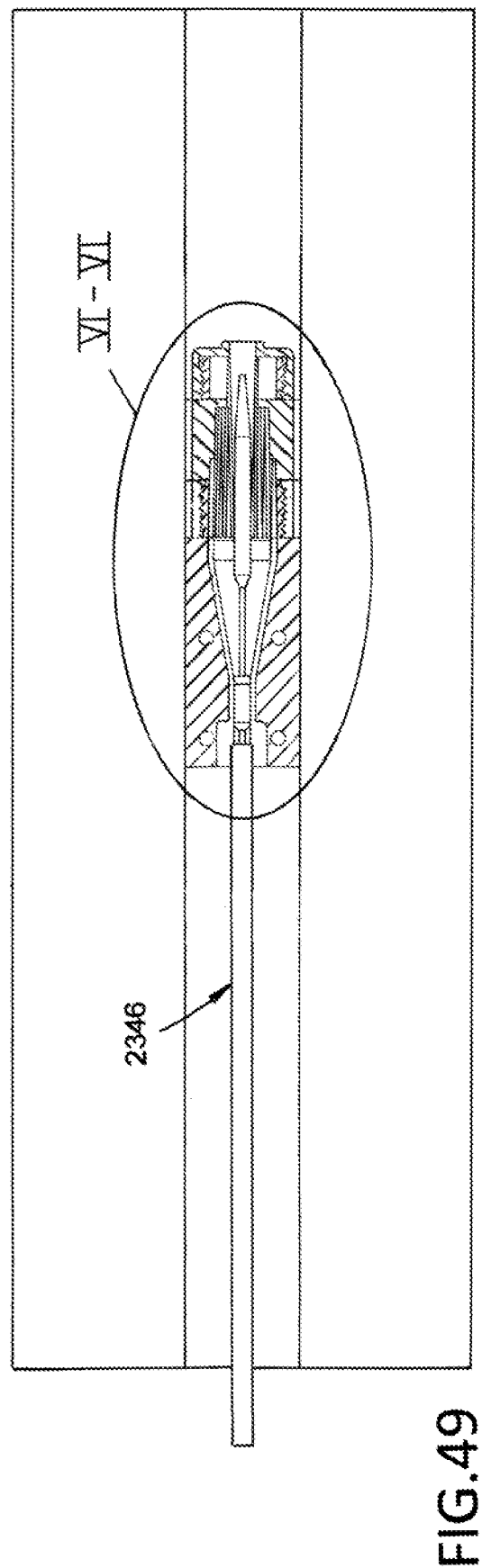
FIG. 49 is a cross-sectional view of a sheath contacting the loading member.

Step 2318 can be accomplished by applying an axial force on the loading puller directed away from the delivery system until it is free of the delivery system. FIGS. 49 and 49A illustrate the sheath advanced toward the loading puller such that it contacts the loading member (e.g., it contacts shoulder 1674 defined within passageway defined by the loading member, it contacts the second end of the loading member).

Step 2322 can optionally be accomplished using structure attached to, or separate from, a loading member that provides for a releasable attachment between the loading member and a sheath during use such that the position of the sheath can be maintained while the elongate member is being retracted into the sheath. For example, a loading member can include a collet, or flexible flaps, that extend into the passageway defined by the loading member that are sized and configured to mate with a sheath and maintain the position of the sheath until an axial force is applied to the sheath to remove it from the loading member.

Step 2324 can be accomplished by applying an axial force on the delivery system directed away from the loading member until the delivery system is free of the loading member. An optional step comprises implanting the implantable medical device within a body of a patient. Another optional step comprises orienting the tip of the delivery system relative to the implantable medical device using the device guard.

While various steps, alternative steps, and optional steps have been described above with respect to the example method 2300, these steps, alternative steps, and optional steps can be included in, accomplished concurrently with, and/or accomplished in the alternative to, the method, steps, alternative steps, and/or optional steps described herein with respect to the example method 1900, example method 2000, example method 2100, example method 2200, example method 2400, and/or example method 2900.

Figure 50:
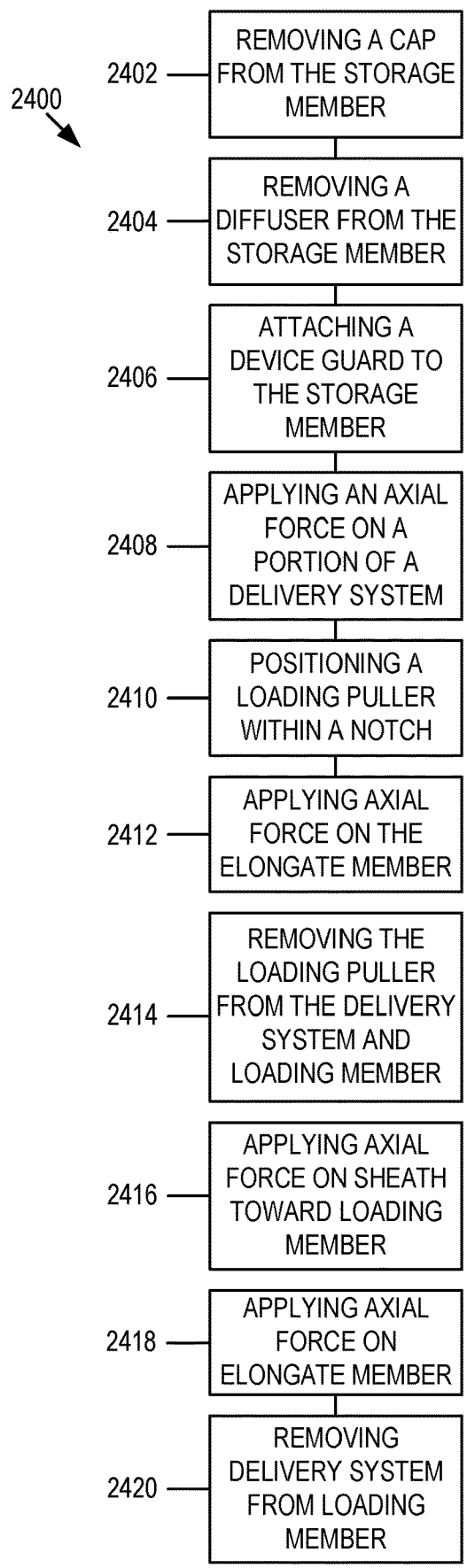
FIG. 50 is a schematic illustration of another example method of loading an implantable medical device onto a delivery system.

FIG. 50 is a schematic illustration of another example method 2400 of loading an implantable medical device onto a delivery system.

A step 2402 comprises removing a cap from a storage member containing an implantable medical device. Another step 2404 comprises removing a diffuser from the storage member. Another step 2406 comprises attaching a device guard to the storage member. Another step 2408 comprises applying an axial force on an elongate member of a delivery system directed toward the storage member while maintaining the position of a sheath of the delivery system such that the elongate member is passed through the storage member and partially disposed within the device guard. Another step 2410 comprises positioning a loading puller within a notch defined by an elongate member of the delivery system. Another step 2412 comprises applying an axial force on the elongate member of the delivery system directed away from the loading member until the first and second ends of the loading puller are disposed within the fourth portion of the loading member. Another step 2414 comprises removing the loading puller from the delivery system and loading member. Another step 2416 comprises applying an axial force on a sheath of the delivery system directed toward the loading member while maintaining the position of the elongate member until the sheath contacts the loading member. Another step 2418 comprises applying an axial force on the elongate member directed away from the loading member while maintaining the position of the sheath such that the elongate member is withdrawn from the loading member and the medical device is advanced into the sheath. Another step 2420 comprises removing the delivery system from the loading member.

Figure 51:
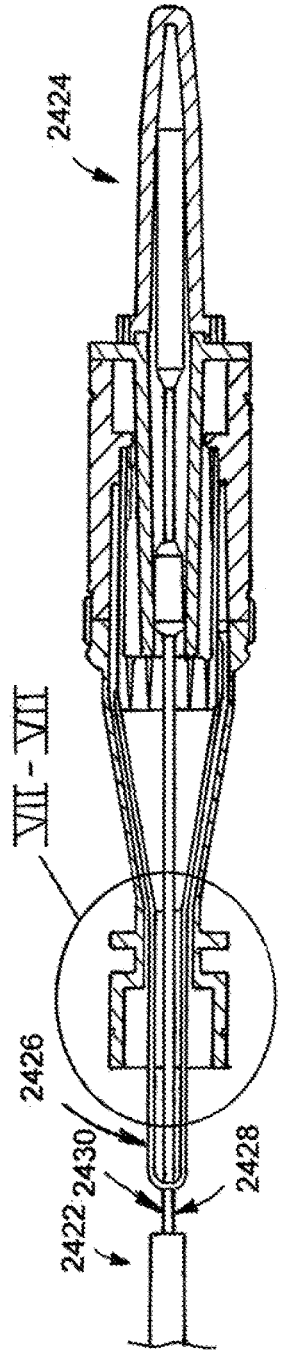
FIG. 51 is a cross-sectional view of a delivery system partially disposed within a device guard and a loading puller disposed within a notch defined by an elongate member.
Figure 52:
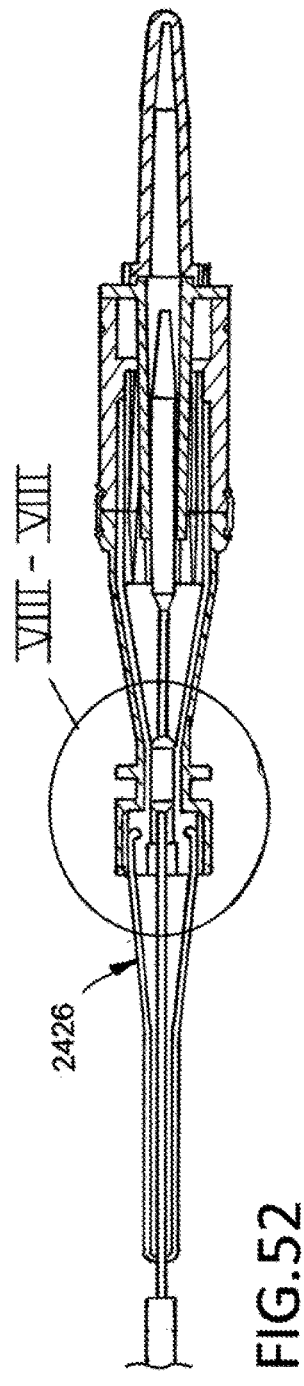
FIG. 52 is a cross-sectional view of a delivery system partially disposed within a device guard and a loading puller disposed within a notch defined by an elongate member. The loading puller is in an open configuration.
Figure 53:
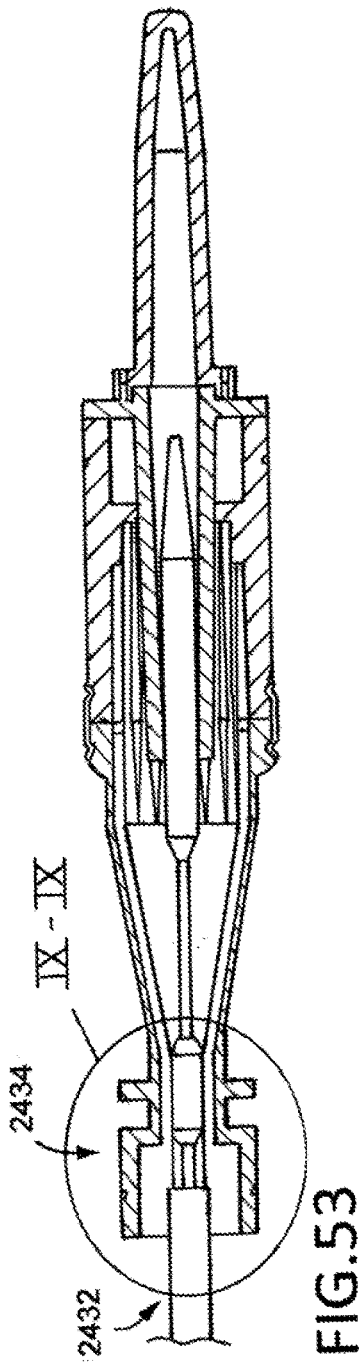
FIG. 53 is a cross-sectional view of a delivery system partially disposed within a device guard and a sheath contacting a loading member.

Step 2404 can be accomplished as described above with respect to step 2304. Step 2406 can be accomplished using any suitable device guard, such as the device guards described herein. In an alternative embodiment, step 2406 can be omitted from a method of loading an implantable medical device onto a delivery system. Step 2408 can be accomplished using any suitable delivery system, such as the delivery systems described herein. Depending on the arrangement of the storage member being used in a method of loading an implantable medical device onto a delivery system, an implantable medical device can be wet during the loading process. FIGS. 51 and 51A illustrate a delivery system 2422 partially disposed within the device guard 2424 and the loading puller 2426 disposed within the notch 2428 defined by the elongate member 2430. FIGS. 52 and 52A illustrate the loading puller 2426 in the open configuration. FIGS. 53 and 53A illustrate the sheath 2432 advanced toward the loading member 2434 such that it contacts the loading member 2434. When disposed within a delivery system, an implantable medical device can be partially disposed on a gripping member and entirely disposed proximal to a tip. An optional step comprises implanting the implantable medical device within a body of a patient. Another optional step comprises orienting the tip of the delivery system relative to the implantable medical device using the device guard. Another optional step comprises removing a second cap from the loading member to expose the loading puller.

While various steps, alternative steps, and optional steps have been described above with respect to the example method 2400, these steps, alternative steps, and optional steps can be included in, accomplished concurrently with, and/or accomplished in the alternative to, the method, steps, alternative steps, and/or optional steps described herein with respect to the example method 1900, example method 2000, example method 2100, example method 2200, example method 2300, and/or example method 2900.

Figure 54:
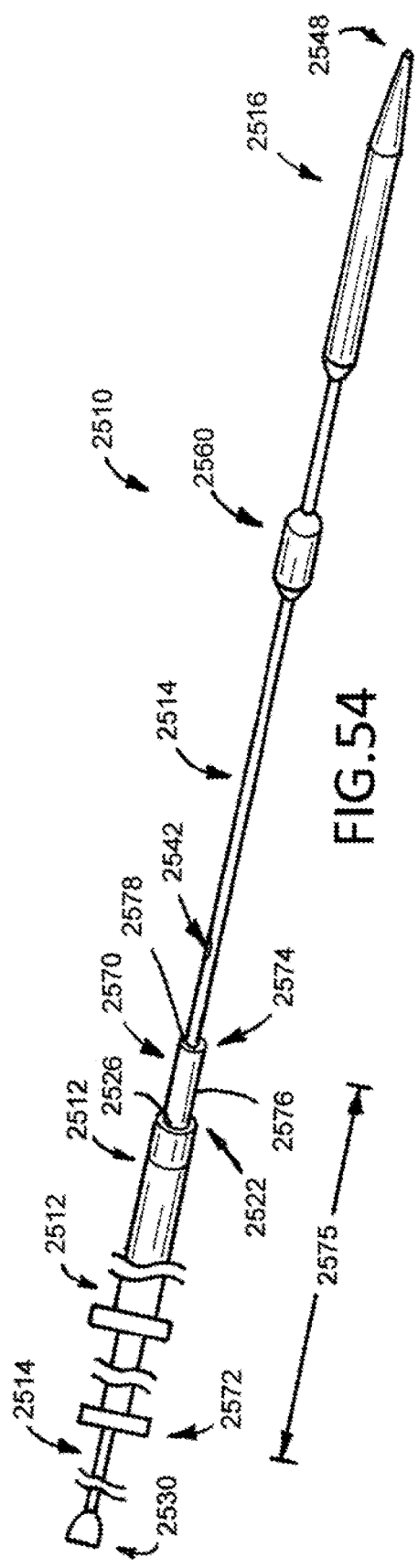
FIG. 54 is a partial perspective view of a fourth example delivery system.

FIG. 54 illustrates another example delivery system 2510. The delivery system 2510 is similar to the delivery system 1410 illustrated in FIG. 30 and described above, except as detailed below. The delivery system 2510 includes a sheath 2512, an elongate member 2514, a tip 2516, a gripping member 2560, and a pushing member 2570.

In the illustrated embodiment, the pushing member 2570 is partially disposed within the lumen 2526 defined by the sheath 2512 and has a first end 2572, a second end 2574, a length 2575, and a main body 2576 that defines a lumen 2578 that extends through the entire length 2575 and is sized and configured to receive a portion of the elongate member 2514. Optionally, the material forming a pushing member can include a radiopaque filled for improved visualization and/or a pushing member can be sized and configured to receive a portion of a gripping member and/or a tip. The lumen 2526 defined by the sheath 2512 is sized and configured to receive a portion of the elongate member 2514, the gripping member 2560, an implantable medical device disposed on the elongate member and/or gripping member, and a portion of the tip 2516. Alternative embodiments, however, can include a sheath that defines a lumen that is sized and configured such that it does not receive a portion of a tip. In use, when it is desired to deploy an implantable medical device disposed within the lumen 2526 defined by the sheath 2512, a user applies an axial force on the sheath 2512 directed away from the tip 2516 and toward the first end 2530 of the elongate member 2514 while maintaining the position of the elongate member 2514 and pushing member 2570. Alternatively, a user applies an axial force on the elongate member 2514 and the pushing member 2570 directed toward the sheath while maintaining the position of the sheath 2512. Once the second end 2522 of the sheath 2512 is positioned at a point between the gripping member 2560 and the notch 2542, a user can either maintain the position of the pushing member 2570 and apply an axial force on the elongate member 2514 directed away from the sheath such that the tip 2516 is advanced toward the second end 2522 of the sheath 2512 or apply an axial force on the pushing member 2570 directed toward the tip while maintaining the position of the elongate member 2514 such that the second end 2574 of the pushing member 2570 is advanced toward the tip 2516, or beyond the second end 2548 of the tip 2516. This provides a mechanism for delivering the implantable medical device at a point of treatment.

Figure 55:
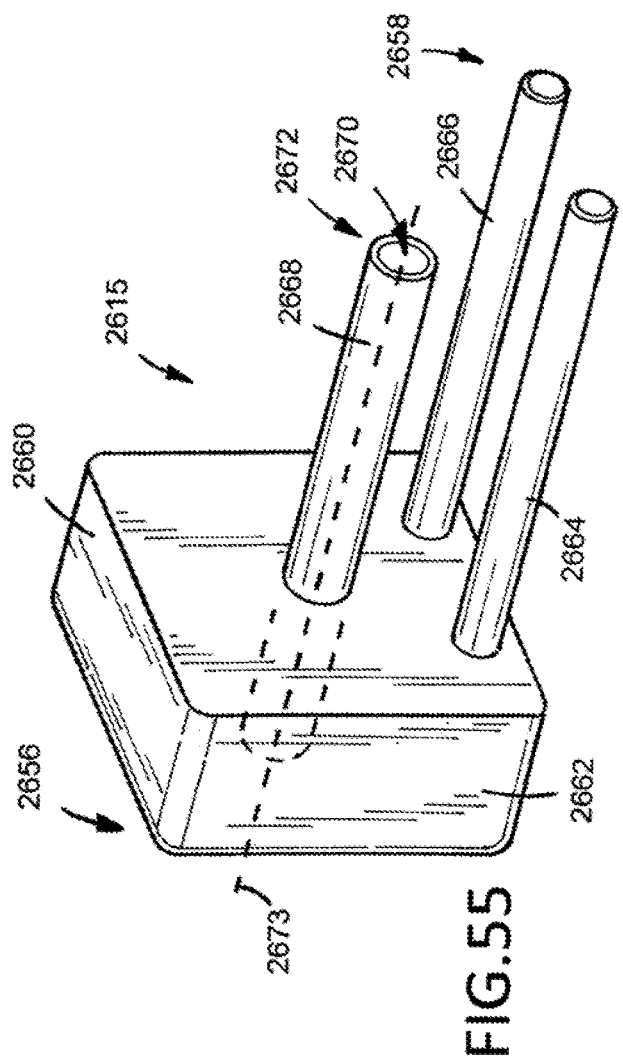
FIG. 55 is a perspective view of an alternative device guard that can be used with a loading member.

FIG. 55 illustrates an alternative device guard 2615 that can be used with a loading member, such as loading member 1614, or any other suitable loading member, as described in more detail herein. The device guard 2615 has a first end 2656, a second end 2658, and a main body 2660 that defines a base 2662, a first projection 2664, a second projection 2666, a third projection 2668, and a passageway 2670. Each of the first projection 2664 and the second projection 2666 extends from the base 2662 to the second end 2658 of the device guard 2615. The third projection 2668 extends from the base 2662 toward the second end 2658 to an end 2672 and has a lengthwise axis 2673. In the illustrated embodiment, the third projection 2668 has a length that is less than the length of each of the first and second projections 2664, 2666. When device guard 2615 is attached to a loading member (e.g., loading member 2814), the lengthwise axis 2673 of the third projection 2668 is coaxial with the axis of the passageway defined by the loading member. Each of the first and second projections 2664, 2666 are disposed on a plane that does not contact the lengthwise axis 2673. However, alternative embodiments can include first and second projections that are disposed on a plane that contains, or contacts, the lengthwise axis of a third projection and/or that have a length that is equal to, or less than, the length of a third projection. The main body 2660 defines the passageway 2670 through the base 2662 and the third projection 2668. The passageway 2670 is sized and configured to receive a portion of a delivery system (e.g., elongate member, tip), as described in more detail herein. Any suitable structure can be included on a device guard, such as device guard 2615, to accomplish releasable attachment to the device guard, such as snap fit connections, and any other structure considered suitable for a particular embodiment, such as those described herein.

FIGS. 56 and 57 illustrate an example loading assister 2710. The loading assister 2710 has a first end 2712, a second end 2714, a shaft 2716, and a hook 2718.

The shaft 2716 has a first end 2720, a second end 2722, and a main body 2724 that defines a first portion 2726 and a second portion 2728. The first portion 2726 has a width 2727, a length 2729, and a thickness 2731. The second portion 2728 has a width 2733, a length 2735, and a thickness 2737. The thickness 2737 of the second portion 2728 is equal to the thickness 2731 of the first portion 2726. The width 2733 of the second portion 2728 is less than the width 2727 of the first portion 2726 and is sized and configured to be received by a passageway defined by a loading member and/or first and second tracks defined by a loading member (e.g., first and second tracks 1090, 1092, first and second tracks 1658, 1662, first and second tracks 2858, 2862). The length 2733 of the second portion 2728 is greater than the length 2729 of the first portion 2726 and greater than the length of the passageway defined by a loading member (e.g., passageway 1032, passageway 1656, passageway 2856). In the illustrated embodiment, the width 2731 of the second portion 2728 is less than the width 1671 of the fourth portion of a passageway defined by a loading member (e.g., fourth portion 1040 of the passageway 1032, fourth portion 1670 of the passageway 1656, fourth portion 2870 of the passageway 2856) and less than the distance between the base of a first track and the base of a third track along the third portion of a passageway of a loading member (e.g., base 1651 of the first track 1658 and the base 1651 of the third track 1662 along the third portion 1668 of the passageway 1656). The thickness 2737 of the second portion 2728 is less than the thickness of each of the first and third tracks of a loading member (e.g., first and third tracks 1658, 1662) defined by the loading member 1614. This structural arrangement provides a mechanism for the loading assister to be advanced through, and withdrawn from, the passageway defined by a loading member.

The hook 2718 is a separate component attached to the second end 2722 of the shaft 2716 and has a first end 2740, a second end 2742, and a main body 2744 that defines a curve 2746 and a recess 2748. The curve 2746 is defined between the first and second ends 2740, 2742. The recess 2748 extends from the second end 2742 and away from the first end 2740 and is sized and configured to receive a portion of a loading puller (e.g., portion between third bend 668 and fourth bend 670 of loading puller 652, curve 2768), such as those described herein.

While the loading assister 2710 has been illustrated as having a particular structural arrangement, and as having a hook attached to a shaft, a loading assister can have any suitable structural arrangement. Selection of a suitable structural arrangement can be based on various considerations, such as the structural arrangement of a loading member through which a loading assister is intended to be passed.

For example, a loading assister can define a shaft that has a first portion and second portion that have the same, or different, lengths, width, and/or thicknesses, a hook attached to any suitable portion of a shaft, and/or a hook that is formed from the material that forms the shaft (e.g., such that a shaft and hook are formed as a single, unitary component).

Figure 60:
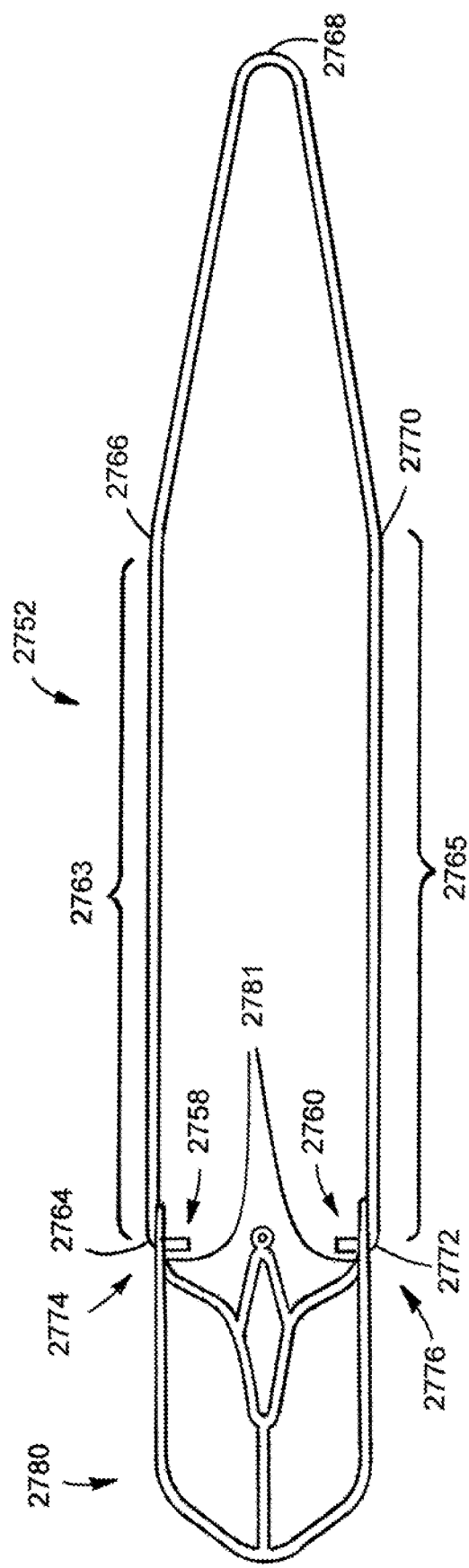
FIG. 60 is a top view of the loading puller illustrated in FIG. 58 attached to an implantable medical device.
Figure 61:
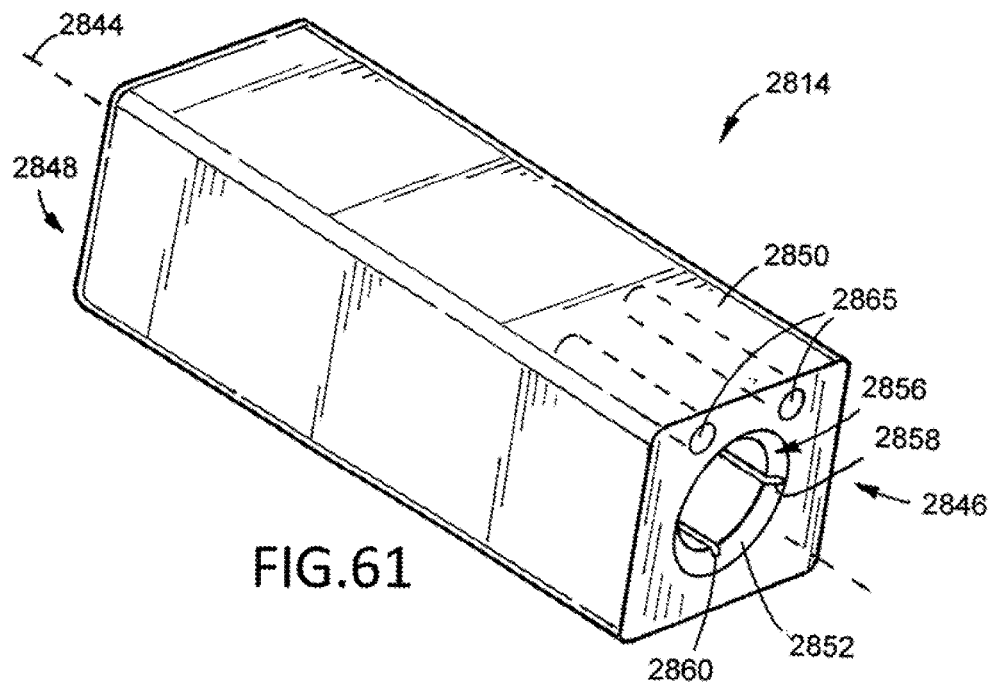
FIG. 61 is a perspective view of another example loading member.
Figure 62:
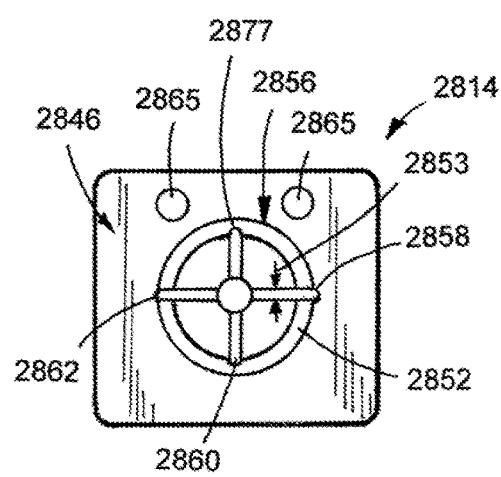
FIG. 62 is an end view of the loading member illustrated in FIG. 61.
Figure 63:
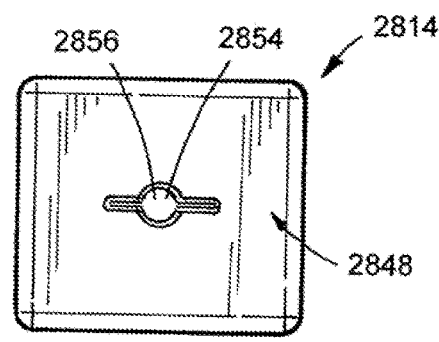
FIG. 63 is another end view of the loading member illustrated in FIG. 61.
Figure 64:
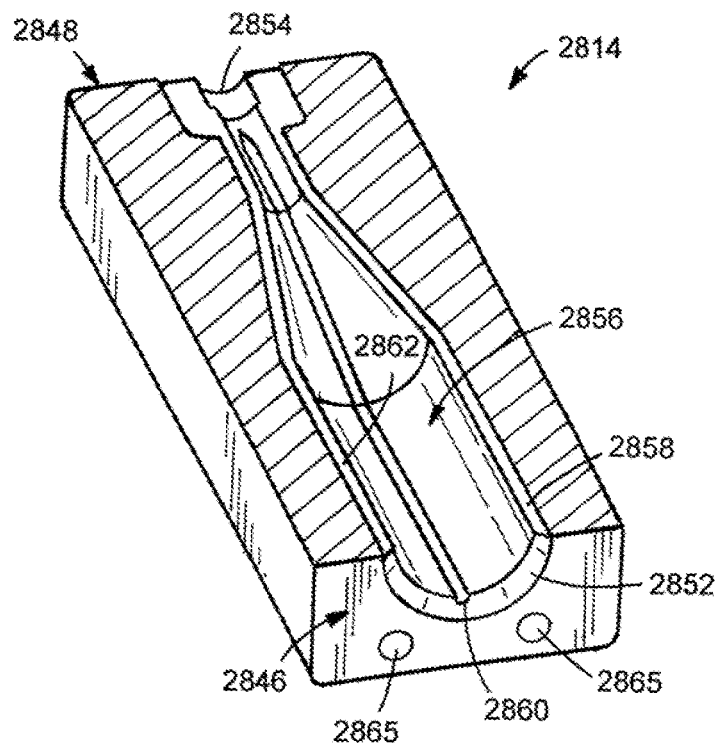
FIG. 64 is a cross-sectional view of the loading member illustrated in FIG. 61 taken along the lengthwise axis of the loading member.
Figure 65:
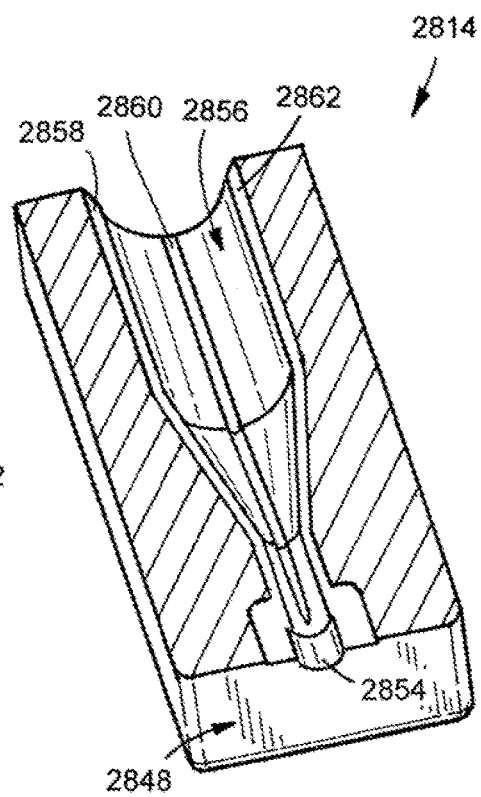
FIG. 65 is another cross-sectional view of the loading member illustrated in FIG. 61 taken along the lengthwise axis of the loading member.
Figure 66:
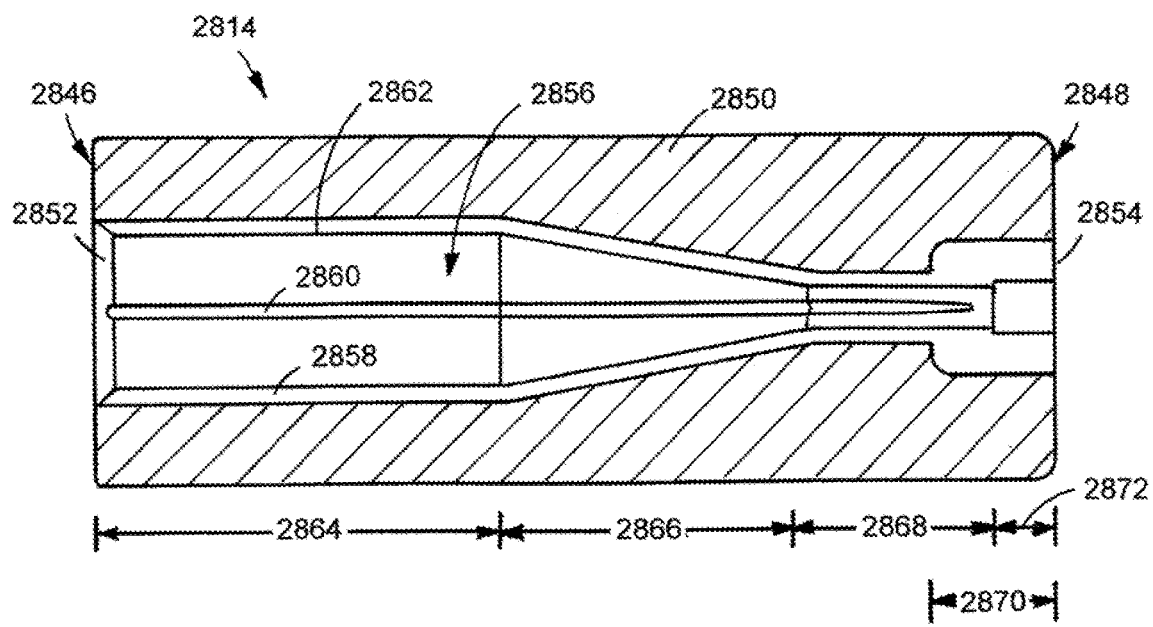
FIG. 66 is another cross-sectional view of the loading member illustrated in FIG. 61 taken along the lengthwise axis of the loading member.

FIGS. 58, 59, and 60 illustrated another example loading puller 2752. The loading puller 2752 is similar to the loading puller 652 illustrated in FIGS. 16, and 16A and described above, except as detailed below.

In the illustrated embodiment, The loading puller 2752 has a lengthwise axis 2757, a first end 2758, a second end 2760, a length 2761, a first portion 2763, a second portion 2765, and main body 2762 that defines a first bend 2764, a second bend 2766, a curve 2768, a third bend 2770, and a fourth bend 2772. The first bend 2764 is positioned near the first end 2758 between the first end 2758 and the second bend 2766 and the fourth bend 2772 is positioned near the second end 2760 between the second end 2760 and the third bend 2770 such that the loading puller defines two hooked ends 2774, 2776 that are adapted to partially surround a portion of a frame of an implantable medical device when the loading puller 2752 is releasably attached to the implantable medical device. The second bend 2766 is disposed between the first bend 2764 and the curve 2768 and the third bend 2770 is disposed between the curve 2768 and the fourth bend 2772 such that the loading puller 2752 defines a u-shaped member 2778 that include portions crossing one another.

The loading puller 2752 is adapted to be disposed within a loading member and is moveable between a first, closed configuration, as shown in FIGS. 58 and 59, and a second, open configuration, as shown in FIG. 60. The loading puller 2752 is biased to the closed configuration. In the closed configuration, the first portion 2763 overlaps the second portion 2765 such that the hooked end 2772, 2774 are directed away from one another. In the open configuration, the first portion 2763 does not overlap with the second portion 2765 and the hooked end 2772, 2774 are directed toward one another such that the first hooked end 2774 is opposably positioned from the second hooked end 2776 relative to the lengthwise axis 2757 of the loading puller 2752. Movement of the loading puller 2752 from the closed to open configuration can be accomplished by applying an axial force on each of the first and second portions directed initially toward the lengthwise axis 2757 of the loading puller 2752 and, once the first and second portions pass the lengthwise axis 2757, directed away from the lengthwise axis 2757. To attach the loading puller 2752 to an implantable medical device 2780, as shown in FIG. 60, the loading puller 2752 is moved to the open configuration such that the loading puller 2752 has a width disposed between the hooked ends 2772, 2774 that is greater than the outside diameter of the implantable medical device 2780. The loading puller 2752 is then advanced toward the implantable medical device and the axial forces are removed from the first and second portions 2763, 2765 such that the loading puller 2752 is releasably attached to the implantable medical device 2780 and the width disposed between the hooked ends 2772, 2774 that is less than the outside diameter of the implantable medical device 2780. When attached to the implantable medical device 2780, a portion of the loading puller 2752 (e.g., hooked ends 2772, 2774) is disposed within one or more openings 2781 defined by a frame of the implantable medical device 2780, such that the loading puller 2752 is capable of applying axial force on the implantable medical device 2780 when axial force is applied to the loading puller 2752 along its lengthwise axis 2757. Removal of the loading puller 2752 from releasable attachment to the implantable medical device 2780, as shown in FIG. 60, can be accomplished by applying an axial force on each of the first and second portions 2763, 2765 directed away from the lengthwise axis 2757 until the loading puller 2752 becomes free of the implantable medical device 2780. A loading puller, such as those described herein can optionally be pre-attached to an implantable medical device (e.g., sterilized implantable medical device), sterilized, and/or disposed within a liquid material (e.g., holding material) within a sealed package. The loading puller 2752 provides a mechanism for maintaining attachment between the loading puller 2752 and an implantable medical device during use until an external force is applied to the loading puller 2752 and/or the implantable medical device.

Figure 35:
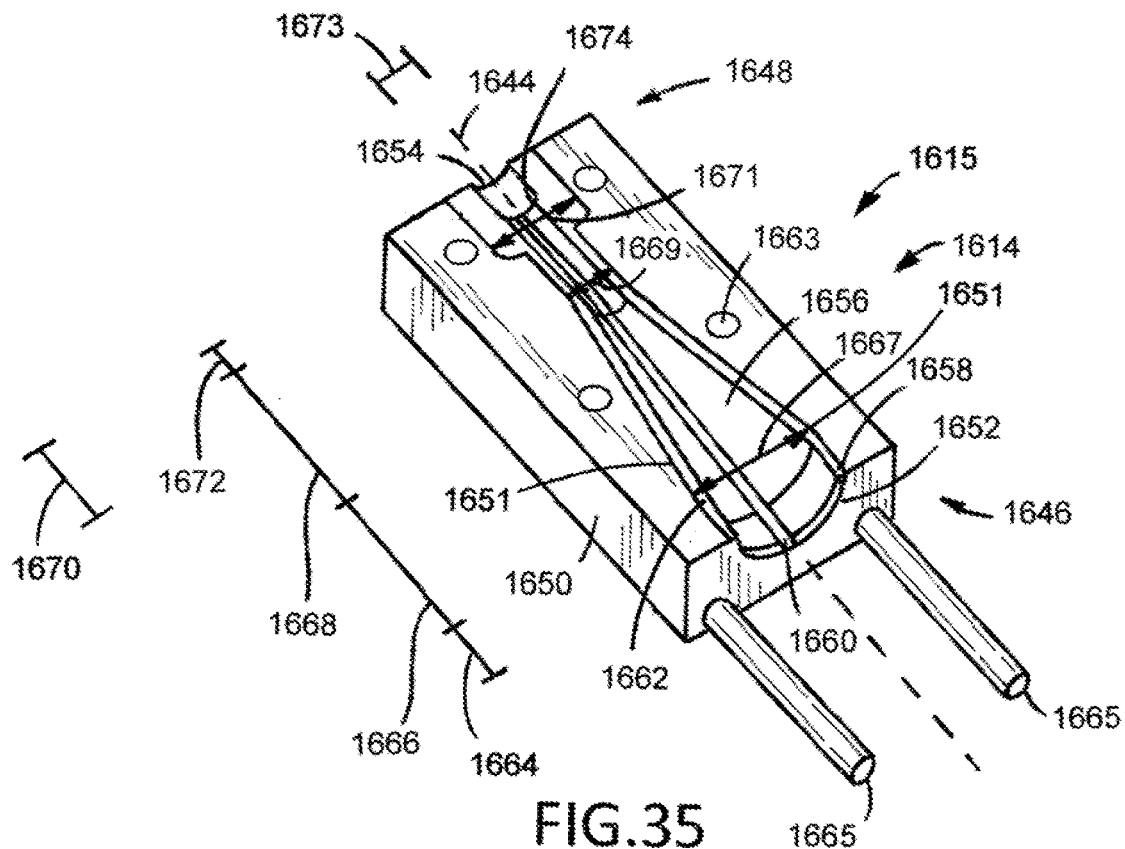
FIG. 35 is a perspective view of a portion of the loading member illustrated in FIG. 33.
Figure 35A:
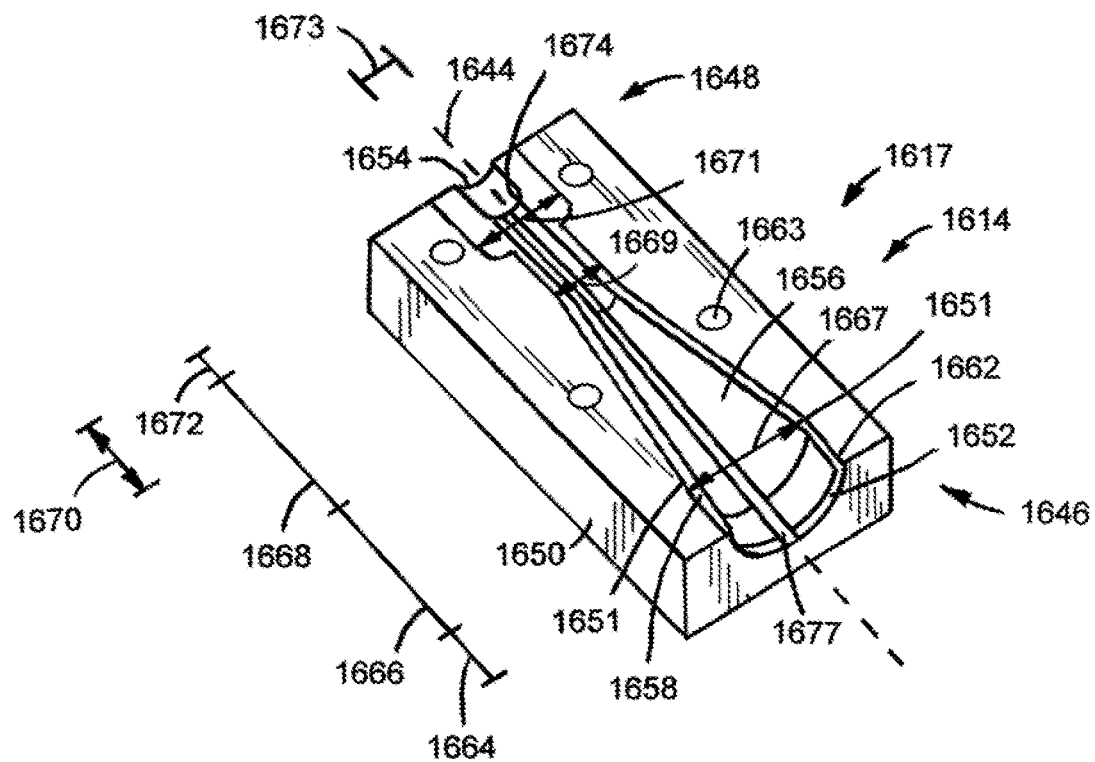
FIG. 35A is a perspective view of another portion of the loading member illustrated in FIG. 33.
Figure 36A:
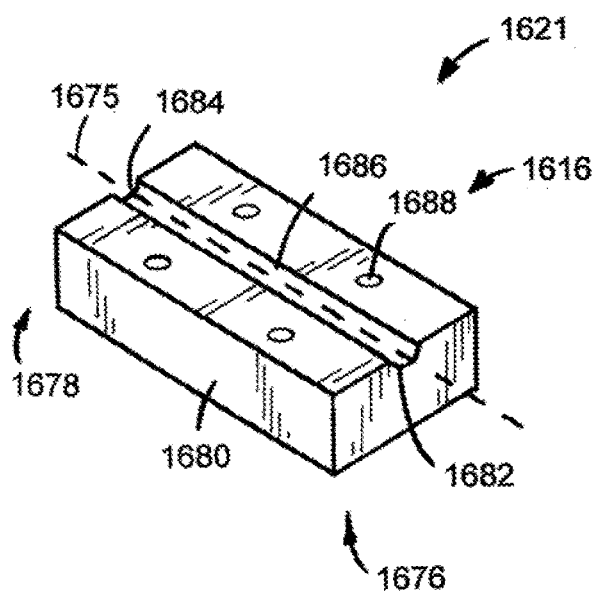
FIG. 36A is a perspective view of another portion of the guide member illustrated in FIG. 33.

FIGS. 61, 62, 63, 64, 65, and 66 illustrate another example loading member 2814. The loading member 2814 is similar to the loading member 1614 illustrated in FIGS. 33, 35, and 35A and described above, except as detailed below.

In the illustrated embodiment, the loading member 2814 is formed as a single, unitary component. The loading member 2814 has a lengthwise axis 2844, a first end 2846, a second end 2848, and a main body 2850 that defines a first opening 2852, a second opening 2854, a passageway 2856, a first track 2858, a second track 2860, a third track 2862, a fourth track 2877, and guide passageways 2865. The passageway 2856 extends from the first opening 2852 to the second opening 2854 and has a first portion 2864, a second portion 2866, a third portion 2868, a fourth portion 2870, and a fifth portion 2872. Each of the first track 2858 and the third track 2862 has a thickness 2853. Each of the second track 2860 and fourth track 2877 extends from the first end 2846 toward the fifth portion 2872 to a location within the third portion 2868. Each of the first track 2858 and third track 2862 is sized and configured to receive a portion of a loading assister and/or loading puller and provides a mechanism to guide the loading assister and/or loading puller through the loading member 2814 during use. Each of the guide passageways 2865 extends from the first end 2846, into the main body 2850, toward the second end 2848, and is sized and configured to receive a projection (e.g., a first projection 2664, a second projection 2666) defined by a device guard (e.g., device guard 2615) to achieve alignment and/or releasable attachment between the loading member 2814 and the device guard.

Figure 67:
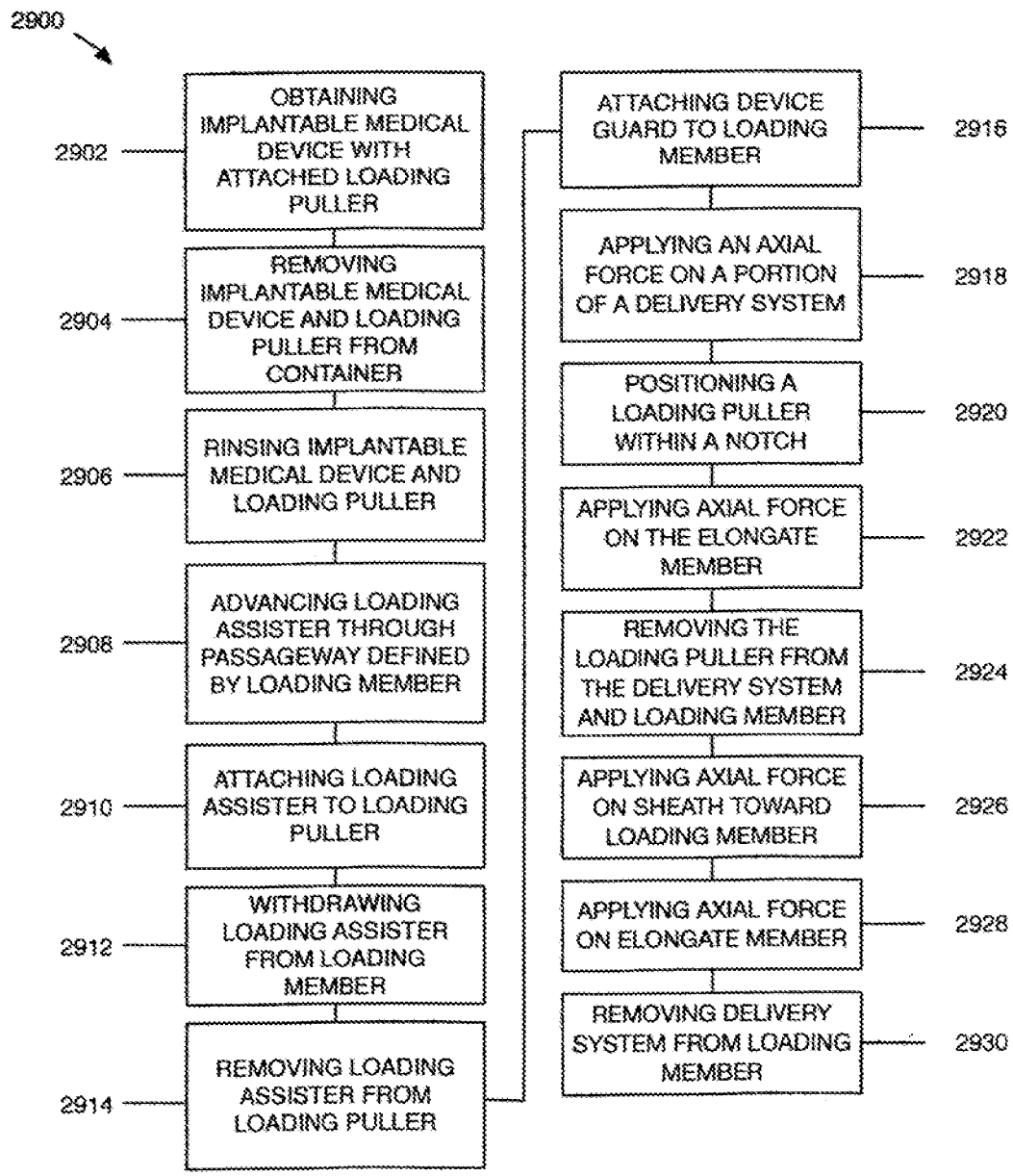
FIG. 67 is a schematic illustration of another example method of loading an implantable medical device onto a delivery system.

FIG. 67 is a schematic illustration of another example method 2900 of loading an implantable medical device onto a delivery system.

A step 2902 comprises obtaining an implantable medical device with an attached loading puller. Another step 2904 comprises removing the implantable medical device and loading puller from the container. Another step 2906 comprises rinsing the implantable medical device and loading puller. Another step 2908 comprises advancing a loading assister through a passageway defined by a loading member. Another step 2910 comprises attaching the loading assister to the loading puller. Another step 2912 comprises withdrawing the loading assister from the loading member. Another step 2914 comprises removing the loading assister from the loading puller. Another step 2916 comprises attaching a device guard to the loading member. Another step 2918 comprises applying an axial force on an elongate member of a delivery system directed toward a loading member such that it is passed through the loading member and partially disposed within the device guard. Another step 2920 comprises positioning a loading puller within a notch defined by an elongate member of the delivery system. Another step 2922 comprises applying an axial force on the elongate member of the delivery system directed away from the loading member until the first and second ends of the loading puller are disposed within the fourth portion of the loading member. Another step 2924 comprises removing the loading puller from the delivery system and loading member. Another step 2926 comprises applying an axial force on a sheath of the delivery system directed toward the loading member while maintaining the position of the elongate member until the sheath contacts the loading member (e.g., is disposed within the loading member and contacts a portion (e.g., shoulder) of the loading member). Another step 2928 comprises applying an axial force on the elongate member directed away from the loading member while maintaining the position of the sheath such that the elongate member is withdrawn from the loading member and the medical device is advanced into the sheath. Another step 2930 comprises removing the delivery system from the loading member.

Step 2902 can be accomplished by obtaining any suitable implantable medical device having any suitable pre-attached loading puller, such as loading puller 2752 and implantable medical device 2780 illustrated in FIG. 60. An implantable medical device and pre-attached loading puller can be disposed within a container filled with a holding material. Alternatively, step 2902 can comprise various separate steps that comprise obtaining an implantable medical device, removing the implantable medical device from container, and attaching a loading puller to the implantable medical device. Alternatively, step 2902 can be omitted from method 2900.

Step 2904 can be accomplished using any suitable method or technique of removing an implantable medical device and a pre-attached loading puller from a container. Alternatively, step 2904 can be omitted from method 2900.

Step 2906 can be accomplished using any method or technique of rinsing an implantable medical device and/or loading puller and any suitable rinsing material, such as those described herein. Alternatively, step 2906 can be omitted from method 2900.

Step 2908 can be accomplished using any suitable loading assister, such as loading assister 2710, and any suitable loading member, such as those described herein (e.g., loading puller 2814). Step 2908 can be accomplished by applying an axial force on the loading assister directed toward the passageway defined by a loading member while maintaining the position of the loading member, or applying and axial force on the loading member directed toward the loading assister, until the second end of the loading assister is passed through the passageway defined by the loading member. Alternatively, step 2908 can be accomplished by maintaining the position of the loading assister while applying an axial force on a loading member toward the loading assister.

Figure 68:
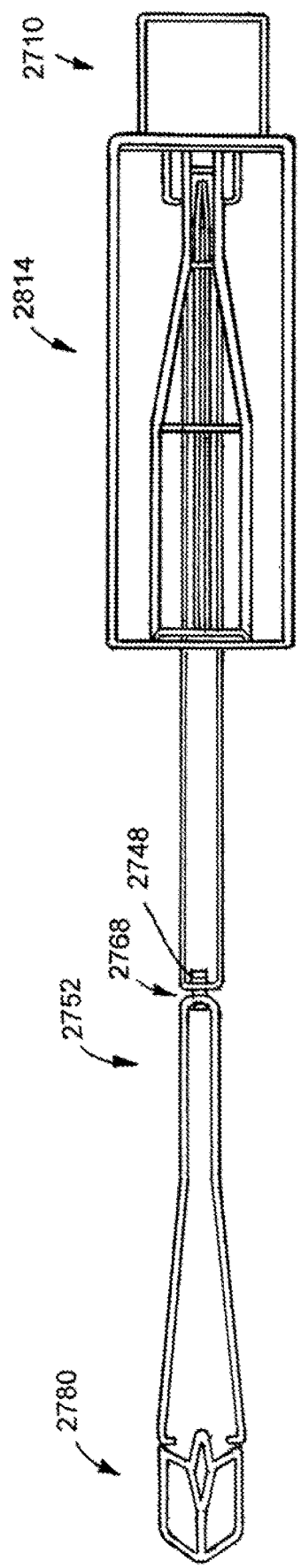
FIG. 68 illustrates a loading assister partially disposed through a loading member and releasably attached to a loading puller that is free of the loading member. An implantable medical device is releasably attached to the loading puller.

Step 2910 can be accomplished by advancing a portion of a loading puller (e.g., portion between second bend 666 and third bend 668 of loading puller 652, curve 2768 of loading puller 2752) into a recess defined by a loading assister (e.g., recess 2748). Optionally, step 2910 can be accomplished such that the loading puller, loading assister, and implantable medical device are positioned vertically. FIG. 68 illustrates the loading assister 2710 illustrated in FIGS. 56 and 57 advanced through the loading member 2814 illustrated in FIGS. 61, 62, 63, 64, 65, and 66, the loading puller 2752 illustrated in FIGS. 58, 59, and 60 releasably attached to the loading assister 2710 (e.g., the curve 2768 disposed within the recess 2748 defined by the loading assister 2710) and free of the loading member 2814, and an implantable medical device 2780 releasably attached to the loading puller 2752. In the illustrated embodiment, the loading member 2814 is formed from a transparent material.

Figure 69:
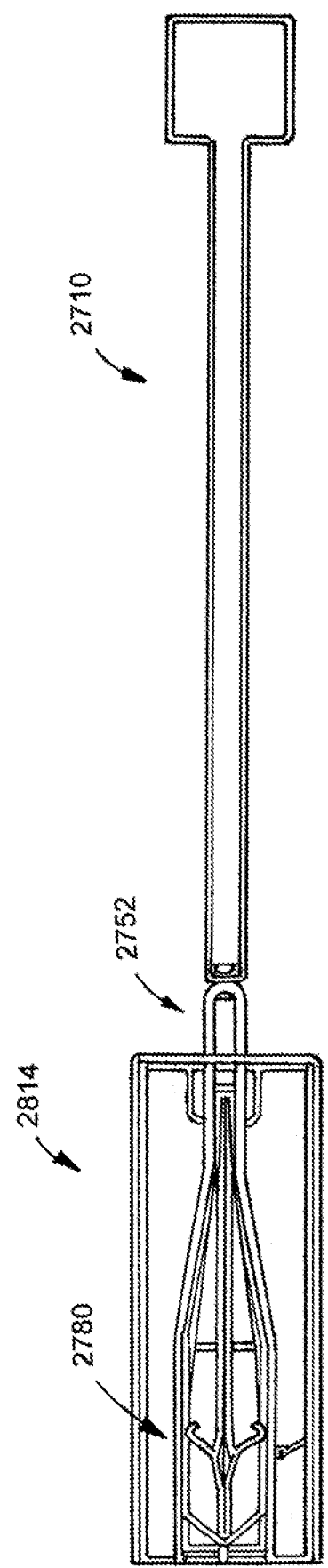
FIG. 69 illustrates a loading assister free of a loading member and releasably attached to a loading puller partially disposed within the loading member. An implantable medical device is releasably attached to the loading puller and is entirely disposed within the loading member.

Step 2912 can be accomplished by applying an axial force on the loading assister directed away from the loading member while maintaining the position of the loading member, or applying and axial force on the loading member directed away from the loading assister, until the second end of the loading assister is passed through the passageway defined by the loading member and the loading assister is free of the loading member. Alternatively, step 2912 can be accomplished by maintaining the position of the loading assister while applying an axial force on a loading member away from the loading assister. Optionally, step 2912 can be accomplished such that the loading puller, loading assister, and implantable medical device are positioned vertically. FIG. 69 illustrates the loading assister 2710 withdrawn from the loading member 2814 such that it is free of the loading member 2814, the loading puller 2752 releasably attached to the loading assister 2710 and partially disposed within the loading member 2814, and an implantable medical device 2780 releasably attached to the loading puller 2752 and entirely disposed within the loading member 2814.

Figure 70:
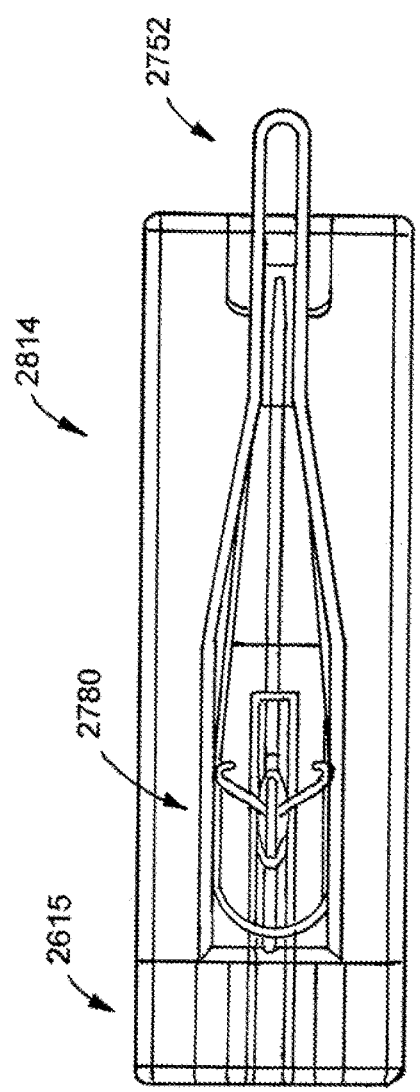
FIG. 70 illustrates a loading puller partially disposed within the loading member. An implantable medical device is releasably attached to the loading puller and is entirely disposed within the loading member. A device guard is releasably attached to the loading member.

Step 2914 can be accomplished by withdrawing the portion of the loading puller (e.g., portion between second bend 666 and third bend 668 of loading puller 652, curve 2768 of loading puller 2752) from the recess defined by a loading assister (e.g., recess 2748). FIG. 70 illustrates the loading puller 2752 free of a loading assister and partially disposed within the loading member 2814 and an implantable medical device 2780 releasably attached to the loading puller 2752 and entirely disposed within the loading member 2814.

Step 2916 can be accomplished using any suitable device guard, such as the device guards described herein (e.g., device guard 2615). Step 2916 can be accomplished by applying an axial force on the device guard directed toward the loading member while maintaining the position of the loading member, or applying and axial force on the loading member directed toward the device guard, until the device guard is releasably attached to the loading member (e.g., the first and second projections 2664, 2666 are disposed within guide passageways 2865). Alternatively, step 2916 can be accomplished by maintaining the position of the device guard while applying an axial force on a loading member toward the device guard. FIG. 70 illustrates the device guard 2615 attached to the loading member 2814.

Step 2918 can be accomplished using any suitable delivery system, such as the delivery systems described herein (e.g., delivery system 2510). Step 2918 can be accomplished by applying an axial force on a portion of the delivery system (e.g., elongate member 2514) directed toward the passageway defined by a loading member while maintaining the position of the remaining portions of the delivery system (e.g., sheath, pushing member) and loading member, or applying and axial force on the loading member directed toward the portion of the delivery system (e.g., elongate member), until the second end of the elongate member is passed through the passageway defined by the loading member. Alternatively, step 2918 can be accomplished by maintaining the position of a portion of the delivery system (e.g., elongate member) while applying an axial force on a loading member toward the loading assister.

Figure 71:
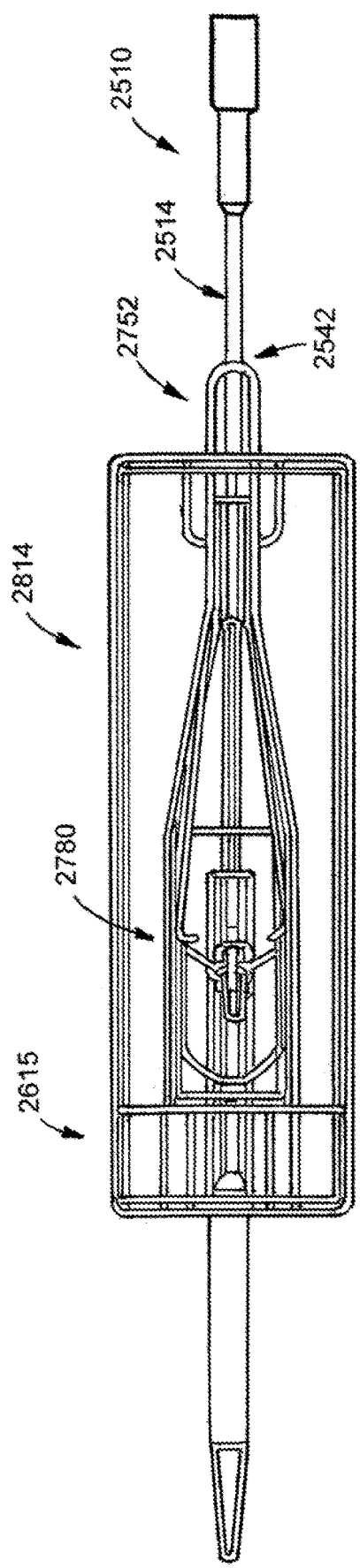
FIG. 71 illustrates a loading puller partially disposed within the loading member and disposed within a notch defined by an elongate member of a delivery system. An implantable medical device is releasably attached to the loading puller and is entirely disposed within the loading member. A device guard is releasably attached to the loading member.

Step 2920 can be accomplished by applying a force on the loading puller directed toward the notch defined by an elongate member of a delivery system until the loading puller (e.g., curve 2768) is disposed within the notch. FIG. 71 illustrates the delivery system 2510 partially disposed within the device guard 2615 and the loading member 2814 and the loading puller 2752 disposed within the notch 2542 defined by the elongate member 2514. In addition, FIG. 71 illustrates the loading puller 2752 partially disposed within the loading member 2814 and an implantable medical device 2780 releasably attached to the loading puller 2752 and entirely disposed within the loading member 2814.

Step 2922 can be accomplished by applying an axial force on the elongate member directed away from the loading member while maintaining the position of the loading member, or applying and axial force on the loading member directed away from the elongate member, until the first and second ends of the loading puller are disposed within the fourth portion of the loading member. Alternatively, step 2922 can be accomplished by maintaining the position of the elongate member while applying an axial force on a loading member away from the elongate member. As the implantable medical device is being compressed in the loading member, a portion, or the entirety, of the implantable medical device is collapsed onto the gripping member providing friction between the gripping member and the implantable medical device.

In embodiments in which loading puller 2752 is being used in method 2900, step 2924 can be accomplished by applying an axial force on each of the first and second portions 2763, 2765 directed away from the lengthwise axis 2757 until the loading puller 2752 becomes free of the implantable medical device 2780 and subsequently applying an axial force on the loading puller directed away from the loading member. In embodiments in which loading puller 652 is being utilized in method 2900, step 2924 can be accomplished by applying an axial force on the loading puller directed away from the loading member.

While various steps, alternative steps, and optional steps have been described above with respect to the example method 2900, these steps, alternative steps, and optional steps can be included in, accomplished concurrently with, and/or accomplished in the alternative to, the method, steps, alternative steps, and/or optional steps described herein with respect to the example method 1900, example method 2000, example method 2100, example method 2200, example method 2300, and/or example method 2400.

The example storage devices, loading devices, guide systems, delivery systems, loading pullers, and methods described herein provide a mechanism for decreasing the complexity of sterilizing, storing, rinsing, and/or loading implantable medical devices and minimizing the risk associated with handling an implantable medical device that is intended for implantation. For example, the example storage devices, loading devices, guide systems, delivery systems, and methods described herein provide a mechanism for sterilizing, storing, rinsing, and/or loading an implantable medical device using a closed system that reduces the interaction with the implantable medical device during sterilization, storing, rinsing, and/or loading.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A method of loading an implantable medical device onto a delivery system comprising:
    positioning an implantable medical device within a loading member;
    positioning a portion of an elongate member of a delivery system within the loading member, the delivery system including the elongate member, a sheath, and a gripping member, the elongate member partially disposed within the sheath and having a first end and a second end, the gripping member attached to the elongate member between the first end of the elongate member and the second end of the elongate member;
    collapsing the implantable medical device onto the gripping member;
    applying a force on the sheath while maintaining the position of the elongate member until the sheath contacts the loading member;
    applying an axial force on the elongate member directed away from the loading member while maintaining the position of the sheath such that the elongate member is withdrawn from the loading member and the implantable medical device is advanced into the sheath; and
    removing the delivery system from the loading member;
    wherein positioning the implantable medical device within the loading member comprises positioning the implantable medical device and a loading puller within the loading member, the loading puller attached to the implantable medical device.

2. The method of claim 1, wherein positioning the implantable medical device and the loading puller within the loading member comprises:
    advancing a loading assister through a passageway defined by the loading member;
    attaching the loading assister to the loading puller;
    withdrawing the loading assister from the loading member such that the loading puller is partially disposed within the loading member and the implantable medical device is entirely disposed within the loading member; and
    removing the loading assister from the loading puller.

3. The method of claim 2, wherein the loading assister has a hook, the hook having a first end, a second end, and a main body defining a curve and a recess; and
    wherein attaching the loading assister to the loading puller is accomplished by advancing a portion of the loading puller into the recess defined by the loading assister.

4. The method of claim 2, wherein withdrawing the loading assister from the loading member such that the loading puller is partially disposed within the loading member and the implantable medical device is entirely disposed within the loading member is accomplished while the loading puller, loading assister, and implantable medical device are positioned vertically.

5. The method of claim 1, wherein the elongate member defines a notch.

6. The method of claim 5, further comprising positioning the loading puller within the notch defined by the elongate member.

7. The method of claim 6, further comprising removing the loading puller from the delivery system, the loading member, and the implantable medical device prior to applying the force on the sheath while maintaining the position of the elongate member until the sheath contacts the loading member.

8. The method of claim 7, wherein the loading puller has a first portion, a second portion, and is moveable between a first, closed configuration and a second, open configuration, in the first, closed configuration the first portion overlaps the second portion.

9. The method of claim 8, wherein the loading puller has a lengthwise axis; and wherein removing the loading puller from the delivery system, the loading member, and the implantable medical device is accomplished by applying an axial force on each of the first and second portions directed away from the lengthwise axis until the loading puller becomes free of the implantable medical device.

10. The method of claim 5, wherein the gripping member is disposed between the notch and the second end of the elongate member.

11. The method of claim 1, wherein the loading puller has a first end, a second end, and a main body that defines a first bend, a second bend, a curve, a third bend, and a fourth bend, the first bend disposed between the first end of the loading puller and the second bend, the second bend disposed between the first bend and the curve, the third bend disposed between the curve and the fourth bend, and the fourth bend disposed between second end of the loading puller and the third bend, the loading puller defining two hooked ends that partially surround a portion of the implantable medical device.

12. The method of claim 1, wherein the implantable medical device includes a frame and a material attached to the frame, the frame defining one or more openings; and wherein the loading puller is disposed within the one or more openings.

13. The method of claim 1, wherein the loading member has a first end, a second end, and a passageway, the passageway having a first portion, a second portion, a third portion, a fourth portion, and a fifth portion, the first portion extending from the first end of the loading member to the second portion and having a constant inside diameter, the second portion extending from the first portion to the third portion and having an inside diameter that tapers from the first portion to the third portion, the third portion extending from the second portion to the fifth portion and having an inside diameter that is less than the inside diameter of the first portion at the first end of the loading member, the fourth portion extending from the third portion to the second end of the loading member and having a width that is greater than the inside diameter of the third portion, the fifth portion extending from the third portion to the second end of the loading member and having an inside diameter that is less than the width of the fourth portion and greater than the inside diameter of the third portion.

14. The method of claim 13, wherein the loading puller has a first end and a second end; and further comprising positioning the first and second ends of the loading puller within the fourth portion of the loading member.

15. The method of claim 1, wherein the delivery system includes a tip disposed on the second end of the elongate member; and wherein the gripping member is attached to the elongate member between the first end of the elongate member and the tip.

16. The method of claim 1, further comprising attaching a device guard to the loading member;

further comprising applying a force on the elongate member of the delivery system such that the delivery system is partially disposed within the loading member and the device guard.

17. The method of claim 1, wherein the implantable medical device includes a frame and a material attached to the frame.

18. The method of claim 17, wherein the implantable medical device is a venous valve.

19. The method of claim 17, wherein the material attached to the frame is a natural material.

20. The method of claim 17, wherein the frame is an expandable frame.

21. The method of claim 1, wherein the gripping member is formed of a polymer.

22. A method of loading an implantable medical device onto a delivery system comprising:

positioning the implantable medical device and a loading puller within a loading member, the loading puller attached to the implantable medical device;

applying an axial force on an elongate member of a delivery system directed toward the loading member such that the delivery system is partially disposed within the loading member, the delivery system including the elongate member, a sheath, and a gripping member, the elongate member partially disposed within the sheath, having a first end and a second end, and defining a notch, the gripping member attached to the elongate member between the notch and the second end of the elongate member;

positioning the loading puller within the notch defined by the elongate member;

applying an axial force on the elongate member directed away from the loading member such that the implantable medical device collapses onto the gripping member;

removing the loading puller from the delivery system, the loading member, and the implantable medical device;

applying an axial force on the sheath directed toward the loading member while maintaining the position of the elongate member until the sheath contacts the loading member;

applying an axial force on the elongate member directed away from the loading member while maintaining the position of the sheath such that the elongate member is withdrawn from the loading member and the implantable medical device is advanced into the sheath; and removing the delivery system from the loading member.

23. A method of loading an implantable medical device onto a delivery system comprising:

positioning the implantable medical device and a loading puller within a loading member, the implantable medical device including an expandable frame and a natural material attached to the frame, the frame defining one or more openings, the loading puller partially disposed within the one or more openings;

applying an axial force on an elongate member of a delivery system directed toward the loading member such that the delivery system is partially disposed within the loading member, the delivery system including the elongate member, a sheath, and a gripping member, the elongate member partially disposed within the sheath, having a first end and a second end, and defining a notch, the gripping member attached to the elongate member between the notch and the second end of the elongate member;

positioning the loading puller within the notch defined by the elongate member;

applying an axial force on the elongate member directed away from the loading member such that the implantable medical device collapses onto the gripping member;

removing the loading puller from the delivery system, the loading member, and the implantable medical device;

applying an axial force on the sheath directed toward the loading member while maintaining the position of the elongate member until the sheath contacts the loading member;

applying an axial force on the elongate member directed away from the loading member while maintaining the position of the sheath such that the elongate member is withdrawn from the loading member and the implantable medical device is advanced into the sheath; and removing the delivery system from the loading member.

* * * * *